United States Patent
Duggal et al.

(10) Patent No.: US 11,001,543 B2
(45) Date of Patent: May 11, 2021

(54) SEPARATION METHODS AND SYSTEMS FOR OXIDATIVE COUPLING OF METHANE

(71) Applicant: Lummus Technology LLC, The Woodlands, TX (US)

(72) Inventors: Suchia Duggal, San Rafael, CA (US); Guido Radaelli, Pleasant Hill, CA (US); Jarod McCormick, San Carlos, CA (US); Andrew Aronson, San Bruno, CA (US); Joel Cizeron, Redwood City, CA (US); Divya Jonnavittula, San Francisco, CA (US)

(73) Assignee: Lummus Technology LLC, The Woodlands, TX (US)

( * ) Notice: Subject to any disclaimer, the term of this patent is extended or adjusted under 35 U.S.C. 154(b) by 0 days.

(21) Appl. No.: 16/357,012

(22) Filed: Mar. 18, 2019

(65) Prior Publication Data
US 2020/0048165 A1 Feb. 13, 2020

Related U.S. Application Data

(63) Continuation of application No. 15/272,205, filed on Sep. 21, 2016, now abandoned.
(Continued)

(51) Int. Cl.
*C07C 2/84* (2006.01)
*C07C 5/32* (2006.01)
(Continued)

(52) U.S. Cl.
CPC .............. *C07C 2/84* (2013.01); *B01D 53/047* (2013.01); *B01D 53/1487* (2013.01);
(Continued)

(58) Field of Classification Search
CPC ................................... C07C 2/82; C07C 2/84
See application file for complete search history.

(56) References Cited

U.S. PATENT DOCUMENTS

| 2,324,172 A | 7/1943 | Parkhurst |
| 2,486,980 A | 11/1949 | Robinson |

(Continued)

FOREIGN PATENT DOCUMENTS

| CA | 2041874 C | 4/1999 |
| CA | 2765769 A1 | 1/2011 |

(Continued)

OTHER PUBLICATIONS

Mokhatab et al. "Handbook of Natural Gas Transmission and Processing: Principles and Practices" 2015. Chapter 7, pp. 237-242. (Year: 2015).*

(Continued)

*Primary Examiner* — Philip Y Louie
*Assistant Examiner* — Alyssa L Cepluch
(74) *Attorney, Agent, or Firm* — Calfee, Halter & Griswold LLP

(57) ABSTRACT

The present disclosure provides a method for generating higher hydrocarbon(s) from a stream comprising compounds with two or more carbon atoms ($C_{2+}$), comprising introducing methane and an oxidant (e.g., $O_2$) into an oxidative coupling of methane (OCM) reactor. The OCM reactor reacts the methane with the oxidant to generate a first product stream comprising the $C_{2+}$ compounds. The first product stream can then be directed to a separations unit that recovers at least a portion of the $C_{2+}$ compounds from the first product stream to yield a second product stream comprising the at least the portion of the $C_{2+}$ compounds.

14 Claims, 33 Drawing Sheets

Related U.S. Application Data

(60) Provisional application No. 62/304,877, filed on Mar. 7, 2016, provisional application No. 62/242,777, filed on Oct. 16, 2015.

(51) Int. Cl.

| | | |
|---|---|---|
| *C07C 7/00* | (2006.01) | |
| *B01D 53/14* | (2006.01) | |
| *B01D 53/22* | (2006.01) | |
| *B01D 53/047* | (2006.01) | |
| *B01D 61/24* | (2006.01) | |
| *C07C 7/144* | (2006.01) | |
| *C07C 7/11* | (2006.01) | |
| *C07C 1/12* | (2006.01) | |

(52) U.S. Cl.
CPC ....... *B01D 53/1493* (2013.01); *B01D 53/228* (2013.01); *B01D 53/229* (2013.01); *B01D 61/246* (2013.01); *C07C 1/12* (2013.01); *C07C 5/32* (2013.01); *C07C 7/005* (2013.01); *C07C 7/11* (2013.01); *C07C 7/144* (2013.01); *B01D 2251/302* (2013.01); *B01D 2251/60* (2013.01); *B01D 2252/10* (2013.01); *B01D 2253/102* (2013.01); *B01D 2253/104* (2013.01); *B01D 2253/106* (2013.01); *B01D 2253/108* (2013.01); *B01D 2253/116* (2013.01); *B01D 2253/1122* (2013.01); *B01D 2253/1124* (2013.01); *B01D 2253/204* (2013.01); *B01D 2253/25* (2013.01); *B01D 2255/104* (2013.01); *B01D 2255/20761* (2013.01); *B01D 2256/24* (2013.01); *B01D 2257/102* (2013.01); *B01D 2257/108* (2013.01); *B01D 2257/502* (2013.01); *B01D 2257/504* (2013.01); *B01D 2257/702* (2013.01)

(56) References Cited

U.S. PATENT DOCUMENTS

| | | |
|---|---|---|
| 2,577,701 A | 12/1951 | Deming et al. |
| 2,579,601 A | 12/1951 | Nelson et al. |
| 2,621,216 A | 12/1952 | White |
| 2,643,216 A | 6/1953 | Findlay |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | De Rosset |
| 3,413,817 A | 12/1968 | Kniel |
| 3,459,678 A | 8/1969 | Hagemeyer, Jr. et al. |
| 3,584,071 A | 6/1971 | McNulty et al. |
| 3,596,473 A | 8/1971 | Streich |
| 3,660,519 A | 5/1972 | Arakawa et al. |
| 3,686,334 A | 8/1972 | Britton |
| 3,686,350 A | 8/1972 | Ono et al. |
| 3,702,886 A | 11/1972 | Argauer et al. |
| 3,709,669 A * | 1/1973 | Marion ................ C07C 1/0485 48/215 |
| 3,751,878 A | 8/1973 | Collins |
| 3,754,052 A | 8/1973 | Hoffman et al. |
| 3,761,540 A | 9/1973 | Carter et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,865,820 A | 9/1989 | Dunster et al. |
| 4,882,400 A | 11/1989 | Dumain et al. |
| 4,891,457 A | 1/1990 | Owen et al. |
| 4,895,823 A | 1/1990 | Kolts et al. |
| 4,900,347 A | 2/1990 | McCue, Jr. et al. |
| 4,935,568 A | 6/1990 | Harandi et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,113,032 A * | 5/1992 | Cameron ................ C07C 2/84 585/500 |
| 5,118,898 A * | 6/1992 | Tyler ........................ B01J 21/16 585/500 |
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |

(56) References Cited

U.S. PATENT DOCUMENTS

| | | |
|---|---|---|
| 5,196,634 A | 3/1993 | Washecheck et al. |
| 5,198,596 A | 3/1993 | Kaminsky et al. |
| 5,240,474 A | 8/1993 | Auvil et al. |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | deVries |
| 5,723,713 A | 3/1998 | Maunders |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Truebenbach et al. |
| 5,935,898 A | 8/1999 | Truebenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hutton et al. |
| 6,342,149 B1 | 1/2002 | Koster et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |

(56) References Cited

U.S. PATENT DOCUMENTS

| | | |
|---|---|---|
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,119,848 B2 | 2/2012 | Cross, Jr. et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Bogild Hansen |
| 8,912,109 B2 | 12/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 8,993,473 B2 | 3/2015 | Melde et al. |
| 9,040,762 B2 | 5/2015 | Cizeron et al. |
| 9,079,815 B2 | 7/2015 | Mukherjee et al. |
| 9,133,079 B2 | 9/2015 | Weinberger et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,334,204 B1 | 5/2016 | Radaelli et al. |
| 9,352,295 B2 | 5/2016 | Rafique et al. |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 9,598,328 B2 | 3/2017 | Nyce et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Ratique et al. |
| 10,407,361 B2 | 9/2019 | Radaelli et al. |
| 10,787,398 B2 | 9/2020 | Nyce et al. |
| 10,787,400 B2 | 9/2020 | Radaelli et al. |
| 10,793,490 B2 | 10/2020 | Radaelli et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1 | 3/2005 | Gattis et al. |
| 2005/0065392 A1 | 3/2005 | Peterson et al. |
| 2005/0107650 A1 | 5/2005 | Sumner |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0112236 A1 | 5/2007 | Bridges et al. |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |
| 2008/0141713 A1 | 6/2008 | Verma |
| 2008/0154078 A1 | 6/2008 | Bozzano et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Lauritzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |

(56) References Cited

U.S. PATENT DOCUMENTS

| | | |
|---|---|---|
| 2010/0000153 A1 | 1/2010 | Kurkjian et al. |
| 2010/0003179 A1 | 1/2010 | Katusic et al. |
| 2010/0028735 A1 | 2/2010 | Basset et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1* | 1/2014 | Iyer .................... C07C 2/84 585/330 |
| 2014/0061540 A1* | 3/2014 | Long .................... B01D 53/02 252/373 |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1* | 3/2015 | Henao .................... B01J 15/005 585/300 |
| 2015/0099914 A1 | 4/2015 | Garza et al. |
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1* | 12/2015 | Xu .................... B01D 53/002 62/620 |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1* | 8/2016 | Mammadov ............. C10G 9/00 |
| 2016/0250618 A1* | 9/2016 | Long .................... B01J 20/226 423/648.1 |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washburn et al. |
| 2016/0368834 A1 | 12/2016 | Nyce et al. |
| 2016/0376148 A1 | 12/2016 | Mamedov et al. |
| 2017/0014807 A1 | 1/2017 | Liang et al. |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1 | 10/2018 | Patel et al. |
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0119182 A1 | 4/2019 | McCormick et al. |
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0389788 A1 | 12/2019 | Mamedov et al. |
| 2020/0031734 A1 | 1/2020 | Cizeron et al. |
| 2020/0031736 A1 | 1/2020 | Weinberger et al. |
| 2020/0055796 A1 | 2/2020 | Nyce et al. |
| 2020/0071242 A1 | 3/2020 | Patel et al. |
| 2020/0131100 A1 | 4/2020 | Schammel et al. |
| 2020/0172452 A1 | 6/2020 | Duggal et al. |
| 2020/0189994 A1 | 6/2020 | Radaelli et al. |
| 2020/0207684 A1 | 7/2020 | Rafique et al. |

(56) References Cited

U.S. PATENT DOCUMENTS

| | | | |
|---|---|---|---|
| 2020/0207685 A1 | 7/2020 | Nyce et al. | |
| 2020/0216370 A1 | 7/2020 | Rafique et al. | |
| 2020/0231519 A1 | 7/2020 | Abudawoud et al. | |

FOREIGN PATENT DOCUMENTS

| | | | |
|---|---|---|---|
| CA | 2800142 C | 6/2018 | |
| CN | 1403375 A | 3/2003 | |
| CN | 101224432 A | 7/2008 | |
| CN | 101387019 A | 3/2009 | |
| CN | 101747927 A | 6/2010 | |
| CN | 102093157 A | 6/2011 | |
| CN | 102125825 A | 7/2011 | |
| DE | 1905517 A1 | 8/1970 | |
| DE | 2540257 A1 | 4/1977 | |
| DE | 3406751 A1 | 8/1985 | |
| DE | 4039960 A1 | 9/1991 | |
| DE | 4338414 C1 | 3/1995 | |
| DE | 4338416 C1 | 4/1995 | |
| DE | 102011080294 A1 | 2/2013 | |
| EP | 106392 A1 | 4/1984 | |
| EP | 177327 A2 | 4/1986 | |
| EP | 253522 A2 | 1/1988 | |
| EP | 303438 A2 | 2/1989 | |
| EP | 336823 A1 | 10/1989 | |
| EP | 608447 A1 | 8/1994 | |
| EP | 634211 A1 | 1/1995 | |
| EP | 722822 A1 | 7/1996 | |
| EP | 761307 A1 | 3/1997 | |
| EP | 764467 A1 | 3/1997 | |
| EP | 716064 B1 | 7/1998 | |
| EP | 1110930 A1 | 6/2001 | |
| EP | 1632467 A1 | 3/2006 | |
| EP | 1749807 A1 | 2/2007 | |
| EP | 1749806 B1 | 10/2008 | |
| EP | 3081292 A1 | 10/2016 | |
| FR | 649429 A | 12/1928 | |
| FR | 2600556 A1 | 12/1987 | |
| GB | 733336 A | 7/1955 | |
| GB | 2191212 A | 12/1987 | |
| JP | 2005161225 A | 6/2005 | |
| RU | 2412147 C2 | 2/2011 | |
| RU | 2447048 C1 | 4/2012 | |
| WO | 8607351 A1 | 12/1986 | |
| WO | 0204119 A1 | 1/2002 | |
| WO | 2004033488 A2 | 4/2004 | |
| WO | 2004056479 A1 | 7/2004 | |
| WO | 2004103936 A1 | 12/2004 | |
| WO | 2005067683 A2 | 7/2005 | |
| WO | 2007125360 A1 | 11/2007 | |
| WO | 2007130515 A2 | 11/2007 | |
| WO | 2008005055 A2 | 1/2008 | |
| WO | 2008014841 A1 | 2/2008 | |
| WO | 2008022147 A1 | 2/2008 | |
| WO | 2008073143 A2 | 6/2008 | |
| WO | 2008150451 A2 | 12/2008 | |
| WO | 2008150451 A3 | 3/2009 | |
| WO | 2009071463 A2 | 6/2009 | |
| WO | 2009074203 A1 | 6/2009 | |
| WO | 2009115805 A1 | 9/2009 | |
| WO | 2010005453 A2 | 1/2010 | |
| WO | 2011008464 A1 | 1/2011 | |
| WO | 2011041184 A2 | 4/2011 | |
| WO | 2011050359 A1 | 4/2011 | |
| WO | 2010069488 A8 | 5/2011 | |
| WO | 2011149996 A2 | 12/2011 | |
| WO | 2012047274 A2 | 4/2012 | |
| WO | 2012047274 A3 | 5/2012 | |
| WO | 2012162526 A2 | 11/2012 | |
| WO | 2013106771 A2 | 7/2013 | |
| WO | 2013169462 A1 | 11/2013 | |
| WO | 2013175204 A1 | 11/2013 | |
| WO | 2013177433 A2 | 11/2013 | |
| WO | 2013177461 A2 | 11/2013 | |
| WO | 2014011646 A1 | 1/2014 | |
| WO | 2014044387 A1 | 3/2014 | |
| WO | 2014049445 A2 | 4/2014 | |
| WO | 2014089479 A1 | 6/2014 | |
| WO | 2013177433 A3 | 8/2014 | |
| WO | 2014131435 A1 | 9/2014 | |
| WO | 2014143880 A1 | 9/2014 | |
| WO | 2015000061 A1 | 1/2015 | |
| WO | 2015003193 A2 | 1/2015 | |
| WO | 2015021177 A1 | 2/2015 | |
| WO | 2015048295 A1 | 4/2015 | |
| WO | 2015066693 A1 | 5/2015 | |
| WO | 2015081122 A2 | 6/2015 | |
| WO | 2015105911 A1 | 7/2015 | |
| WO | 2015106023 A1 | 7/2015 | |
| WO | 2015081122 A3 | 12/2015 | |
| WO | 2016012371 A1 | 1/2016 | |
| WO | 2016149507 A1 | 9/2016 | |
| WO | 2016160563 A1 | 10/2016 | |
| WO | 2016205411 A2 | 12/2016 | |
| WO | 2016210006 A2 | 12/2016 | |
| WO | 2016210006 A3 | 4/2017 | |
| WO | 2017065947 A1 | 4/2017 | |
| WO | 2016205411 A3 | 9/2017 | |
| WO | 2017180910 A1 | 10/2017 | |
| WO | 2018009356 A1 | 1/2018 | |
| WO | 2018085820 A1 | 5/2018 | |
| WO | 2018102601 A1 | 6/2018 | |
| WO | 2018114900 A1 | 6/2018 | |
| WO | 2018118105 A1 | 6/2018 | |
| WO | 2019010498 A1 | 1/2019 | |
| WO | 2019055220 A1 | 3/2019 | |

OTHER PUBLICATIONS

Wikipedia search, Adiabatic Process, Mar. 2011, 10 pages.

Witek-Krowiak, A. et al. Carbon Dioxide Removal in a Membrane Contactor-Selection of Absorptive Liquid/Membrane System. Intl J Chem Eng and Appl. (2012) 3(6):391-395.

Wong, et al. Oxidative coupling of methane over alkali metal oxide promoted La2 03/BaCO3 catalysts. J. Chem. Tech. Biotechnol. 65:351-354, 1996.

Wu, et al., High-Capacity Methane Storage in Metal-Organic Frameworks M2(dhtp): The Important Role of Open Metal Sites, J. Am. Chem. Soc. 131 (13):4995-5000, 2009.

Xu, et al. Maximise ethylene gain and acetylene selective hydrogenation efficiency. Petroleum technology quarterly 18.3 (2013): 39-42.

Xu, G. et al. An Improved CO2 Separation and Purification System Based on Cryogenic Separation and Distillation Theory. Energies (2014) 7:3484-3502.

Yan, D. Modeling and Application of a Thermoelectric Generator. Thesis, Univ. Toronto (2011).

Yang, et al. Anistropic synthesis of boat shaped core shell Au—Ag nanocrystals and nanowires. Nanotechnology 17:2304-2310, 2006.

Yu, et al. Oxidative coupling of methane over acceptor-doped SrTi 03: Correlation between p-type conductivity and C2 selectivity and C2 yield. Journal of Catalysis. 13 (5): 338-344, 1992.

Zhang, Q. Journal of Natural Gas Chem., 12:81, 2003.

Zhao, et al. Technologies and catalysts for catalytic preparation of ethene. Industrial catalysis 12 (Supplement): 285-289, 2004.

Zhou et al. Functionalization of lanthanum hydroxide nanowires by atom transfer radical polymerization. Nanotechnology 18, 2007, 7 pages.

Zhou. BP-UOP Cyclar Process. Handbook of Petroleum Refining Processes, The McGraw-Hill Companies (2004), pp. 2.29-2.38.

Zhou, et al., Enhanced H2 Adsorption in Isostructural Metal-Organic Frameworks with Open Metal Sites: Strong Dependence of the Binding Strength on Metal Ions, J. Am. Chem. Soc., 2008, 130(46):15268-69.

Zimmerman, et al. Ethylene. Ulmann's Encyclopedia of Inudstrial Chemisty, Wiley-VCH Verlag GmbH & Co. KGaA, Weinheim, Germany, 2009, 66 pages.

International search report and written opinion dated Feb. 2, 2017 for PCT Application No. PCT/US2016/052959.

Office Action dated Nov. 30, 2017 for U.S. Appl. No. 15/272,205.

(56) References Cited

OTHER PUBLICATIONS

Office Action dated Sep. 25, 2018 for U.S. Appl. No. 15/272,205.
Extended European Search Reported dated Mar. 6, 2019 for European Patent Application No. 16855929.2.
Communication under Rule 71(3) EPC dated Mar. 10, 2020 for European Patent Application No. 16855929.2.
Chemical Engineering—"Separation Processes: Supercritical CO2: A Green Solvent" Feb. 1, 2010.
Li, et al. Combined Single-Pass Conversion of Methane via Oxidative Coupling and Dehydroaromatization. Catalysis Letters, Sep. 2003, vol. 89, Issue 3-4, pp. 275-279.
Li, et al. Energy and Fuels. 2008, 22: 1897-1901.
Ling, et al. Preparation of Ag core Au shell Nanowires and Their Surface Enhanced Raman Spectroscopic Studies. Acta Chimica Sinica. 65 (9): 779-784, 2007.
Liu, et al. A novel Na2 W04—Mn.SiC monolithic foam catalyst with improved thermal properties for the oxidative coupling of methane. Catalysis Communications 9: 1302-1306, 2008.
Liu, et al. Increasing the Density of Adsorbed Hydrogen with Coordinatively Unsaturated Metal Centers in Metal-Organic Frameworks Langmuir, 2008, 24:4772-77.
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Lunsford, et al. The oxidative coupling of methane on chlorinated Lithium-doped magnesium oxide. J. Chem. Soc., Chem. Commun., 1991, 1430-1432.
Makal, et al., Methane storage in advanced porous materials, Critical Review, Chem. Soc. Rev., 2012, 41 :7761-7779.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands.
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.
Morgan, C.R. et al. Gasoline from Alcohols. Ind Eng Chem Prod Res Dev(1981) 20:185-190.
Natural Gas Spec Sheet, 2003, prepared by Florida Power and Light Company.
Neltner, et al. Production of Hydrogen Using Nanocrystalline Protein-templated catalysts on M12 Phage. ACSNano 4(6):3227-3236, 2010.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.
Niu, et al. Preparation and characterization of La2 O3CO3 nanowires with high surface areas. Jounral of the Chinese Rare Earth Society 23 (Spec. Issue): 33-36, Dec. 2005.
Ogura et al. Formation of Uniform Mesopores in ZSM-5 Zeolite through Treatment in Alkaline Solution, Chemistry Letters, 2000, pp. 882-883.
Ohashi, Y. et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009.
Olah, G. Hydrocarbon Chemistry. 2nd Edition, John Wiley & Sons, 2003.
Olefins Conversion Technology, Website Accessed Aug. 28, 2014, http:www.CBI.com.
Pak, et al. Elementary Reactions in the Oxidative Coupling of Methane over Mn/NA2 W04/Si02 and Mn/NA2 W04/Mg0 Catalysts. Journal of Catalysis 179:222-230, 1998.
Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.
Process Systems; "Steam Tables" Apr. 8, 2017—https://web.archive.org/web/20170408152403/https://valvesonline.com.au/references/steamtables/.
Qiu, et al. Steady-state conversion of methane to aromatics in high yields using an integrated recycle reaction system. Catalysis Letters 48: 11-15, 1997.
Rousseau, Handbook of Separation Process Technology, 1987, p. 682.
Saito, et al. Dehydrogenation of Propane Over a Silica-Supported Gallium Oxide Catalyst. Catalysis Letters, Sep. 2003, vol. 89, Issue 3-4, pp. 213-217.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK—Conference, Hamburg, Germany (2007).
Simons, K. Membrane Technologies for CO2 Capture. Dissertation, U. of Twente (2010).
Smith, et al. Recent developments in solvent absorption technologies at the CO2CRC in Australia. Energy Procedia 1 (2009): 1549-1555.
Somorjai, et al. High technology catalysts towards 100% selectivity Fabrication, characterization and reaction studies. Catalysis today 100:201-215, 2005.
Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.
Suzuki, K. Toshiba's Activity in Clean Coal and Carbon Capture Technology for Thermal Power Plants. APEC Clean Fossil Energy Technical and Policy Seminar (Feb. 22, 2012).
Tabak, S.A. et al. Conversion of Methanol over ZSM-5 to Fuels and Chemicals. Cat Today (1990) 307-327.
Takanabe, et al. Mechanistic Aspects and Reaction Pathways for Oxidative Coupling of Methane on Mn/NA2 W04/Si02 Catalysts. Journal of Physical Chemistry C 113(23):10131-10145, 2009.
Takanabe, et al. Rate and Selectivity Enhancements Mediated by OH Radicals in the Oxidative coupling of Methane Catalyzed by Mn/NA2 W04/Si02 . Angewandte Chemie International Edition 47:7689-7693, 2008.
Tong, et al. Development strategy research of downstream products of ethene in Tianjin. Tianjin Economy, pp. 37-40,1996.
Trautmann, et al. Cryogenic technology for nitrogen rejection from variable content natural gas. Presented at the XIV Convencion Internacional de Gas, Caracas, Venezuela, May 10-12, 2000, 13 pages.
Wang, et al. Autothermal oxidative coupling of methane on the SrCO3/Sm2 03 catalysts. Catalysis communications 10: 807-810, 2009.
Wang, et al. Comparative study on oxidation of methane to ethane and ethylene over NA2 W04—Mn/SiO2 catalysts prepared by different methods. Journal of Molecular Catalysis A: Chemical 245:272-277, 2006.
Wang, et al. Low temperature selective oxidation of methane to ethane and ethylene over BaCO3/La2 03 catalysts prepared by urea combustion method. Catalysis communications 7: 5963, 2006.
Wang, et al., Critical Influence of BaCO3 on Low Temperature Catalytic Activity of BaCO3/Zr02 Catalysts for Oxidative Coupling of Methane, Catalysis Letters (2009), 129:156-162.
Water Electrolysis & Renewable Energy Systems. FuelCellToday (May 2013).

(56) References Cited

OTHER PUBLICATIONS

Agarwal, et al., Aqueous Au—Pd colloids catalyze selective CH4 oxidation to CH3OH with O2 under mild conditions, Science 358, Oct. 13, 2017, 223-27.

Ahari, et al. Effects of operating parameters on oxidative coupling of methane over Na—WMn/SiO2 catalyst at elevated pressures. Journal of Natural Gas Chemistry. vol. 20, Issue 2, Mar. 2011, pp. 204-213.

American Petroleum Institute Publication 534 Heat Recovery Steam Generators Jan. 1995 (51 pages).

Autothermal Partial Oxidative Coupling of Methane. IP.com, Prior Art Database Technical Disclosure, Jul. 29, 2008, 5 pages.

Barrett, et al. The determination of pore volume and area distributions in porous substances—Compuatations from nitrogen isotherms. J. Am. Chem. Soc., 1951, vol. 73, pp. 373-380.

Berstad, D. et al. Low-temperature CO2 removal from natural gas. Energy Procedia (2012) 26:41-48.

Bloch, et al. Hydrocarbon Separations in a Metal-Organic Framework with Open Iron(II) Coordination Sites, Science, 2012, 335:1606-1610.

Bollmann, et al. Ethylene tetramerization: a new route to produce 1-octene in exceptionally high selectivities. J Am Chem Soc. Nov. 17, 2004;126(45):14712-3.

Botella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.

Carter, et al. High activity ethylene trimerisation catalysts based on diphosphine ligands. Chem Commun (Camb). Apr. 21, 2002;(8):858-9.

Caskey, et al., Dramatic Tuning of Carbon Dioxide Uptake via Metal Substitution in a Coordination Polymer with Cylindrical Pores, J. Am. Chem. Soc., (2009), 130(33): 10870-71.

Cavani, et al. Oxidative dehydrogenation of ethane and propane: How far from commercial implementation? Catalysis Today. 2007; 127(1-4):113-131.

Chemsystems PERP Report Ethylene Oxide/Ethylene Glycol 2005.

Chen, et al. M2 Forming—A Process for Aromatization of Light Hydrocarbons. Ind. Eng. Chem. Process. Des. Dev. 1986, 25, 151-155.

Choudhary, et al. Aromatization of dilute ethylene over Ga-modified ZSM-5 type zeolite catalysts. Microporous and Mesoporous Materials 47: 253-267, 2001.

Choudhary, et al. Oxidative conversion of methane/natural gas into higher hydrocarbons. Catalysis Surveys from Asia 8(1): 15-25, Feb. 2004.

Choudhary, et al. Surface Basicity and Acidity of Alkaline Earth-Promoted La2 O3 Catalysts and Their Performance in Oxidative Coupling of Methane. Journal of Chemical Technology and Biotechnology 72:125-130, 1998.

Christopher, et al. Engineering Selectivity in Heterogeneous Catalysis: Ag Nanowires as Selective Ethylene Epoxidation Catalysts. Journal of the American Chemical Society 130: 11264-11265, 2008.

Corma, From Microporous to Mesoporous Molecular Sieve Materials and Their Use in Catalysis, Chern. Rev., 97, 1997, pp. 2373-2419.

Debart, et al. α-MNO2 Nanowires: a catalyst for the 02 Electrode in Rechargeabl Lithium Batteries. Angewandte Chemie International Edition 47: 4521-4524, 2008.

Dietzel, et al., Adsorption properties and structure of CO2 adsorbed on open coordination sites of metal-organic framework Ni2(dhtp) from gas adsorption, IR spectroscopy and X-ray diffraction, Chem. Commun_ (2008), 5125-5127.

Ding, X et al. Effect of acid density of HZSM-5 on the oligomerization of ethylene in FCC dry gas. J Nat Gas Chem (2009) 18:156-160.

Duan, et al. Three-dimensional copper (II) metal-organic framework with open metal sites and anthracene nucleus for highly selective C2H2/CH4 and C2NH2/CO2 gas separation at room temperature. Microporous and Mesoporous Materials. vol. 181, Nov. 15, 2013, pp. 99-104.

enger, et al. A review of catalytic partial oxidation of methane to synthesis gas with emphasis on reaction mechanisms over transition metal catalysts. Applied Catalysis A: General 346 (1-2): 1-27, Aug. 2008.

Fallah, et al., A New Nano-(2Li20/Mg0) Catalyst/Porous Alpha-Alumina Composite for the Oxidative Coupling of Methane Reaction, AIChE Journal, Mar. 2010, 56(3):717-28.

Gao, et al. A study on methanol steam reforming to CO2 and H2 over the La2 C04 nanofiber catalyst. Journal of Solid State Chemistry 181: 7-13, 2008.

Gao, et al. The direct decomposition of NO over the La2 Cu04 nanofiber catalyst. Journal of Solid State Chemistry 181: 2804-2807, 2008.

Geier, et al., Selective adsorption of ethylene over ethane and propylene over propane in the metal-organic frameworks M2(dobdc) (M=Mg, Mn, Fe, Co, Ni, Zn), Chem. Sci., 2013, 4:2054-2061.

Ghosh, et al., Absorption of carbon dioxide into aqueous potassium carbonate promoted by boric acid, Energy Procedia, Feb. 2009, pp. 1075-1081.

Godini, et al. Techno-economic analysis of integrating the methane oxidative coupling and methane reforming processes. Fuel processing technology 2013 v.106 pp. 684-694.

Goto et al, Mesoporous Material from Zeolite, Journal of Poruous Materials, 2002, pp. 43-48.

Graves, C.R. Recycling CO2 into Sustainable Hydrocarbon Fuels: Electrolysis of CO2 and H2O. Dissertation, Columbia University (2010).

Guo, et al. Current Status and Some Perspectives of Rare Earth Catalytic Materials. Journal of the Chinese Rare Earth Society 25(1): 1-15, Feb. 2007.

Guo, X. et al. Direct, Nonoxidative Conversion of Methane to Ethylene, Aromatics, and Hydrogen. Science (2014) 344:616-619.

Gupta, M. Review on Heat Recovery Unit with Thermoelectric Generators. Intl J Eng and Innov Tech (IJEIT) (2014) 4(4):128-131.

Haag, W.O. et al. Aromatics, Light Olefins and Gasoline from Methanol: Mechanistic Pathways with ZSM-5 Zeolite catalyst. J Mol Catalysis (1982) 17:161-169.

He, et al. A microporus metal-organic framework for highly selective separation of acetylene, ethylene, and ethane from methane at room temperature. Chemistry. Jan. 9, 2012; 18(2):613-9. doi 10.1002/chem.201102734. Epub Dec. 8, 2011.

Hsseinpour, Performance of CaX Zeolite for Separation of C2H6, C2H4, and CH4 by Adsorption Process; Capacity, Selectivity, and Dynamic Adsorption Measurements, Separation Science and Technology, 2011, 46:349-355.

Huang, et al. Exploiting shape effects of La2O3 nanocrystals for oxidative coupling of methane reaction. Nanoscale 5(22): 10844-10848, 2013.

Huang, et al. Exploiting shape effects of La2O3 nanocrystals for oxidative coupling of methane reaction. Nanoscale—Electronic Supplementary Material, 2013, 7 pages.

Iwamoto, M. One step formation of propene from ethene or ethanol through metathesis on nickel ion-loaded silica. Molecules. Sep. 13, 2011;16(9):7844-63.

Kaibe, H. et al. Recovery of Plant Waste Heat by a Thermoelectric Generating System. Komatsu Tech Report (2011) 57(164):26-30.

Kaminsky, M.P. et al. Deactivation of Li-Based Catalysts for Methane Oxidative Coupling. Poster ACS Symposium on Natural Gas Upgrading II (Apr. 5-10, 1992).

Kaminsky, M.P. et al. Oxygen X-Ray Absorption Near-Edge Structure Characterization of the Ba-Doped Yttria Oxidative Coupling Catalyst. J Catalysis (1992) 136:16-23.

Keller, Gas-Adsorption Processes: State of the Art, American Chemical Society, 1983,pp. 145-169.

Keller, et al. Synthesis of Ethylene via Oxidative Coupling of Methane. Journal of Catalysis 73: 9-19, 1982.

Knuuttila, et al. Advanced Polyethylene Technologies—Controlled Material Properties. Long Term Properties of olyolefins Advances in Polymer Science vol. 169, 2004, pp. 13-28.

(56) References Cited

OTHER PUBLICATIONS

Kuang, et al. Grafting of PEG onto lanthanum hydroxide nanowires. Materials Letters 62:4078-4080, 2008.
Labinger. Oxidative coupling of methane: an inherent limit to selectivity? Catal. Lett. 1988; 1:371-376.
Li, B. et al. Advances in CO2 capture technology: A patent review. Applied Energy (2013) 102:1439-1447.
Extended European Search Report for EP Application No. 20203394.0 dated Jan. 25, 2021.

* cited by examiner

SEPARATION METHODS AND SYSTEMS FOR OXIDATIVE COUPLING OF METHANE

CROSS-REFERENCE

This application is a continuation of U.S. patent application Ser. No. 15/272,205, filed Sep. 21, 2016, which claims priority to U.S. Provisional Patent Application No. 62/242,777, filed Oct. 16, 2015, and U.S. Provisional Patent Application No. 62/304,877, filed Mar. 7, 2016, each of which is entirely incorporated herein by reference for all purposes.

STATEMENT OF GOVERNMENT SUPPORT

This invention was made with government support under grant numbers DE-EE0005769 awarded by the United States Department of Energy (DOE). The government has certain rights in the invention.

BACKGROUND

The modern refining and petrochemical industry may make extensive use of fractionation technology to produce and separate various desirable compounds from crude oil. The conventional fractionation technology may be energy intensive and costly to install and operate. Cryogenic distillation has been used to separate and recover hydrocarbon products in various refining and petrochemical industries.

SUMMARY

Recognized herein is a need for non-cryogenic separation methods and systems, such as for oxidative coupling of methane (OCM) processes.

Aspects of the present disclosure provide processes for recovering olefins from a stream containing mix of hydrocarbons by utilizing techniques based the use of adsorbents. In some embodiments, systems and methods enable the separation, pre-separation, purification and/or recovery of hydrocarbons, including, but not limited to, olefins, ethylene, propylene, methane, and ethane, and $CO_2$, from a multicomponent hydrocarbon stream such as an effluent stream from an oxidative coupling of methane (OCM) reactor or an ethylene-to-liquids (ETL) reactor. The hydrocarbon stream can also be the feed to the OCM or ETL reactor in certain cases. In certain cases, the feed to the ETL reactor is the effluent from OCM reactor. In some cases, a separation process utilizing adsorbents can be used to purify and pre-treat existing hydrocarbon streams (such as refinery off-gases, cracker off-gas, streams from NGL plants, and others), followed by use of the resulting olefin rich stream (e.g., pressure swing adsorption tail gas) as the ETL feed.

The present disclosure provides various improvements in OCM and ETL processes, such as, without limitation, a separation and pre-separation process to recover desired or predetermined components from an OCM reactor effluent, $CO_2$ recovery and capture techniques, enhanced heat recovery methods to utilize the OCM reaction heat more efficiently, and techniques and technologies to further reduce the carbon footprint of the OCM process.

An aspect of the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) carbon dioxide ($CO_2$); and (b) directing the product stream from the OCM reactor into a separations unit that employs a $CO_2$ separation unit to separate the $CO_2$ from the product stream and enrich the $C_{2+}$ compounds in the product stream, which $CO_2$ separation unit employs (i) sorbent or solvent separation of $CO_2$, (ii) membrane separation of $CO_2$, (iii) cryogenic or low temperature separation of $CO_2$ having an operating temperature greater than a boiling point of methane and less than a boiling point of $CO_2$, (iv) metal-organic framework-based separation, or (v) antisublimation separation of $CO_2$.

In some embodiments of aspects provided herein, the product stream is directed into the separations unit through one or more additional units. In some embodiments of aspects provided herein, the sorbent or solvent separation of $CO_2$ employs an amine based absorption unit. In some embodiments of aspects provided herein, the sorbent or solvent separation of $CO_2$ employs a Benfield process. In some embodiments of aspects provided herein, the sorbent or solvent separation of $CO_2$ employs diethanolamine. In some embodiments of aspects provided herein, the sorbent or solvent separation of $CO_2$ employs glycol dimethylether. In some embodiments of aspects provided herein, the sorbent or solvent separation of $CO_2$ employs propylene carbonate. In some embodiments of aspects provided herein, the sorbent or solvent separation of $CO_2$ employs Sulfinol. In some embodiments of aspects provided herein, the sorbent or solvent separation of $CO_2$ employs a zeolite. In some embodiments of aspects provided herein, the sorbent or solvent separation of $CO_2$ employs active carbon. In some embodiments of aspects provided herein, the $CO_2$ separation unit comprises a membrane $CO_2$ separation unit. In some embodiments of aspects provided herein, the membrane separation of $CO_2$ employs a polymeric membrane. In some embodiments of aspects provided herein, the membrane separation of $CO_2$ employs a metallic membrane. In some embodiments of aspects provided herein, the membrane separation of $CO_2$ employs a ceramic membrane. In some embodiments of aspects provided herein, the membrane separation of $CO_2$ employs a hybrid membrane comprising a membrane supporting a solvent or sorbent. In some embodiments of aspects provided herein, the membrane separation of $CO_2$ employs a poly ionic liquid membrane. In some embodiments of aspects provided herein, the membrane separation of $CO_2$ employs a supported ionic liquid membrane. In some embodiments of aspects provided herein, the membrane separation of $CO_2$ employs a polyetherimide membrane. In some embodiments of aspects provided herein, the membrane separation of $CO_2$ employs an amorphous fluoropolymer based membrane. In some embodiments of aspects provided herein, the method further comprises directing the $CO_2$ from the product stream to a methanation reactor that reacts the $CO_2$ to yield a methanation product stream comprising methane. In some embodiments of aspects provided herein, the method further comprises directing the methane in the methanation product stream to the OCM reactor. In some embodiments of aspects provided herein, the method further comprises separating the product stream into (i) an ethylene product stream comprising ethylene and (ii) a $C_{3+}$ product stream comprising compounds with three or more carbon atoms ($C_{3+}$ compounds). In some embodiments of aspects provided herein, the method further comprises directing ethane from the product stream to the OCM reactor. In some embodiments of aspects provided herein, the method further comprises, prior to directing the product stream into the separations unit, compressing the product stream. In some embodiments of aspects provided herein, the $CO_2$ separation unit employs the sorbent or solvent separation of $CO_2$. In some embodiments of aspects provided herein, the $CO_2$ separation unit employs the membrane separation of $CO_2$. In some embodiments of aspects provided herein, the $CO_2$ separation unit employs the cryogenic or low temperature separation of $CO_2$ having an operating temperature greater than a boiling point of methane and less than a boiling point of $CO_2$. In some embodiments of aspects provided herein, the $CO_2$ separation unit employs the metal-organic framework-based separation. In some embodiments of aspects provided herein, the $CO_2$ separation unit employs the anti-sublimation separation of $CO_2$.

Another aspect of the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) carbon dioxide ($CO_2$); (b) directing the product stream from the OCM reactor into a first $CO_2$ separation unit that separates at least some of the $CO_2$ from the product stream to produce an enriched stream comprising (i) the $C_{2+}$ compounds and (ii) at least some of the $CO_2$; (c) directing the enriched stream to a cryogenic separations unit that separates the $C_2H_4$ from the $C_{2+}$ compounds to produce an ethylene stream comprising (i) the $C_2H_4$ and (ii) the $CO_2$; and (d) directing the ethylene stream to a second $CO_2$ separation unit that separates the $CO_2$ from the ethylene stream to produce an ethylene product stream.

In some embodiments of aspects provided herein, the enriched stream contains at most about 2.0 mol % $CO_2$. In some embodiments of aspects provided herein, the enriched stream contains at most about 1.0 mol % $CO_2$. In some embodiments of aspects provided herein, the enriched stream contains at most about 0.5 mol % $CO_2$. In some embodiments of aspects provided herein, the first $CO_2$ separation unit comprises a membrane, a pressure swing absorption (PSA) unit, an amine unit, or any combination thereof. In some embodiments of aspects provided herein, the second $CO_2$ separation unit comprises a membrane, a pressure swing absorption (PSA) unit, an amine unit, or any combination thereof. In some embodiments of aspects provided herein, the cryogenic separations unit comprises a de-methanizer.

Another aspect of the present disclosure provides a method for generating compounds with two or more Carbon atoms (C2+ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) carbon monoxide (CO) and/or carbon dioxide ($CO_2$); and (b) directing the product stream from the OCM reactor into a separations unit that selectively separates olefins from the paraffins.

In some embodiments of aspects provided herein, the separations unit selectively separates ethylene from paraffins. In some embodiments of aspects provided herein, the separations unit comprises an absorber stripper unit employing pi-complexation. In some embodiments of aspects provided herein, the separations unit comprises a membrane unit including a membrane contactor employing pi-complexation. In some embodiments of aspects provided herein, the separations unit comprises a pressure swing adsorption (PSA) unit comprising a sorbent having dispersed metal ions that are capable of complexing with the olefins. In some embodiments of aspects provided herein, the PSA unit comprises a sorbent selected from a zeolite, a molecular sieve sorbent, a carbon molecular sieve, an activated carbon, a carbon nanotube, and a polymeric resin. In some embodiments of aspects provided herein, the method further comprises using an oxidizing agent to regenerate stabilize the pi-complex. In some embodiments of aspects provided herein, the oxidizing agent comprises $HNO_3$ or $KMnO_4$. In some embodiments of aspects provided herein, the separations unit comprises (i) a pressure swing adsorption (PSA) unit, (ii) a temperature swing adsorption (TSA) unit, or (iii) a membrane unit employing a metal-organic framework (MOF), and the olefins separated in (b) comprise ethylene.

Another aspect of the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) $C_1$ compounds including un-reacted $CH_4$; and (b) directing the product stream into a separations unit that separates the $C_{2+}$ compounds from the $C_1$ compounds, which separations unit does not contain a de-methanizer.

In some embodiments of aspects provided herein, the separations unit contains a distillation column and an oil absorber. In some embodiments of aspects provided herein, the distillation column does not condense methane.

Another aspect of the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) $C_1$ compounds including un-reacted $CH_4$; (b) directing the product stream into a pre-separations unit that produces (i) a bottoms stream comprising the $C_{2+}$ compounds and (ii) an overhead stream comprising the $C_1$ compounds and at least some of the $C_{2+}$ compounds; and (c) directing the overhead stream into an oil absorber that removes the at least some of the $C_{2+}$ compounds to produce a $C_1$ stream.

In some embodiments of aspects provided herein, the OCM process is integrated with a methanol to olefins (MTO) unit, a steam cracker, or a metathesis process. In some embodiments of aspects provided herein, the pre-separation unit does not include a de-methanizer. In some embodiments of aspects provided herein, the pre-separation unit does not condense methane. In some embodiments of aspects provided herein, the overhead stream comprises at least about 10% $C_{2+}$ compounds. In some embodiments of aspects provided herein, the overhead stream comprises at least about 5% $C_{2+}$ compounds. In some embodiments of aspects provided herein, the overhead stream comprises at least about 1% $C_{2+}$ compounds. In some embodiments of aspects provided herein, the overhead stream comprises at least about 0.1% $C_{2+}$ compounds.

Another aspect of the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) $C_1$ compounds including un-reacted $CH_4$; and (b) directing the product stream into a separations unit containing a metal organic framework (MOF) that produces (i) a bottoms stream comprising the $C_{2+}$ compounds and (ii) an overhead stream comprising the $C_1$ compounds.

In some embodiments of aspects provided herein, the method further comprises (c) directing the overhead stream to a methanation unit for converting carbon dioxide ($CO_2$) and/or carbon monoxide (CO) into methane ($CH_4$); and (d) directing the $CH_4$ into the OCM reactor. In some embodiments of aspects provided herein, the method further comprises (e) directing the bottoms stream to a second separations unit containing a metal organic framework (MOF) that separates olefins from paraffins. In some embodiments of aspects provided herein, the separations unit comprises a pressure swing absorber (PSA) that contains the MOF. In some embodiments of aspects provided herein, the separations unit comprises a temperature swing absorber (TSA) that contains the MOF. In some embodiments of aspects provided herein, the $C_1$ compounds include hydrogen ($H_2$).

Another aspect of the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor having a catalytic section and a cracking section to produce an OCM product stream, which catalytic section reacts the $O_2$ and $CH_4$ to yield ethylene ($C_2H_4$), ethane ($C_2H_6$) and heat, which cracking section uses the heat to convert $C_2H_6$ into $C_2H_4$, and which product stream comprises (i) $C_{2+}$ compounds including ethylene ($C_2H_4$) and ethane ($C_2H_6$) and (ii) $C_1$ compounds including un-reacted $CH_4$; (b) directing the product stream into a separations unit containing a metal organic framework (MOF) that produces (i) a first stream comprising the $C_2H_4$, (ii) a second stream comprising the $C_2H_6$ and (iii) a third stream comprising the $C_1$ compounds; (c) directing the second stream into the cracking section; and (d) directing the third stream into the catalytic section.

In some embodiments of aspects provided herein, the third stream is directed to a methanation unit prior to directing to the catalytic section, which methanation unit converts carbon dioxide ($CO_2$) and/or carbon monoxide (CO) into methane ($CH_4$). In some embodiments of aspects provided herein, the separations unit comprises a pressure swing absorber (PSA) that contains the MOF. In some embodiments of aspects provided herein, the separations unit comprises a temperature swing absorber (TSA) that contains the MOF. In some embodiments of aspects provided herein, the $C_1$ compounds include hydrogen ($H_2$).

Another aspect of the present disclosure provides a system for generating compounds with two or more carbon atoms ($C_{2+}$ compounds), comprising: (a) an oxidative coupling of methane (OCM) reactor configured to receive oxygen ($O_2$) and methane ($CH_4$) and react the $O_2$ and $CH_4$ in an OCM process to yield a product stream comprising (i) $C_{2+}$ compounds including ethylene ($C_2H_4$) and (ii) carbon dioxide ($CO_2$); and (b) a separations unit fluidically coupled to the OCM reactor and configured to receive the product stream from the OCM reactor, wherein the separations unit comprises a $CO_2$ separation unit to separate the $CO_2$ from the product stream, and to enrich the $C_{2+}$ compounds in the product stream, which $CO_2$ separation unit employs (i) sorbent or solvent separation of $CO_2$, (ii) membrane separation of $CO_2$, (iii) cryogenic or low temperature separation of $CO_2$ having an operating temperature greater than a boiling point of methane and less than a boiling point of $CO_2$, (iv) metal-organic framework-based separation, or (v) antisublimation separation of $CO_2$.

In some embodiments of aspects provided herein, the separations unit comprises one or more additional units, and the product stream is directed into the separations unit through the one or more additional units. In some embodiments of aspects provided herein, the sorbent or solvent separation of $CO_2$ employs an amine based absorption unit. In some embodiments of aspects provided herein, the sorbent or solvent separation of $CO_2$ employs a Benfield process. In some embodiments of aspects provided herein, the sorbent or solvent separation of $CO_2$ employs diethanolamine. In some embodiments of aspects provided herein, the sorbent or solvent separation of $CO_2$ employs glycol dimethylether. In some embodiments of aspects provided herein, the sorbent or solvent separation of $CO_2$ employs propylene carbonate. In some embodiments of aspects provided herein, the sorbent or solvent separation of $CO_2$ employs Sulfinol. In some embodiments of aspects provided herein, the sorbent or solvent separation of $CO_2$ employs a zeolite. In some embodiments of aspects provided herein, the sorbent or solvent separation of $CO_2$ employs active carbon. In some embodiments of aspects provided herein, the $CO_2$ separation unit comprises a membrane $CO_2$ separation unit. In some embodiments of aspects provided herein, the membrane separation of $CO_2$ employs a polymeric membrane. In some embodiments of aspects provided herein, the membrane separation of $CO_2$ employs a metallic membrane. In some embodiments of aspects provided herein, the membrane separation of $CO_2$ employs a ceramic membrane. In some embodiments of aspects provided herein, the membrane separation of $CO_2$ employs a hybrid membrane comprising a membrane supporting a solvent or sorbent. In some embodiments of aspects provided herein, the membrane separation of $CO_2$ employs a poly ionic liquid membrane. In some embodiments of aspects provided herein, the membrane separation of $CO_2$ employs a supported ionic liquid membrane. In some embodiments of aspects provided herein, the membrane separation of $CO_2$ employs a polyetherimide membrane. In some embodiments of aspects provided herein, the membrane separation of $CO_2$ employs an amorphous fluoropolymer based membrane. In some embodiments of aspects provided herein, the system further comprises a methanation reactor that is configured to receive the $CO_2$ from the product stream and react the $CO_2$ to yield a methanation product stream comprising methane. In some embodiments of aspects provided herein, the methane in the methanation product stream is directed to the OCM reactor. In some embodiments of aspects provided herein, the product stream is further separated into (i) an ethylene product stream comprising ethylene and (ii) a $C_{3+}$ product stream comprising compounds with three or more carbon atoms ($C_{3+}$ compounds). In some embodiments of aspects provided herein, ethane is directed from the product stream to the OCM reactor. In some embodiments of aspects provided herein, the product stream is compressed, prior to being directed into the separations unit. In some embodiments of aspects provided herein, the $CO_2$ separation unit employs the sorbent or solvent separation of $CO_2$. In some embodiments of aspects provided herein, the $CO_2$ separation unit employs the membrane separation of $CO_2$. In some embodiments of aspects provided herein, the $CO_2$ separation unit employs the cryogenic or low temperature separation of $CO_2$ having an operating temperature greater than a boiling point of methane and less than a boiling point of $CO_2$. In some embodiments of aspects provided herein, the $CO_2$ separation unit employs the metal-organic framework-based separation. In some embodiments of aspects provided herein, the $CO_2$ separation unit employs the antisublimation separation of $CO_2$.

Another aspect of the present disclosure provides a system for generating compounds with two or more carbon atoms ($C_{2+}$ compounds), comprising: an oxidative coupling of methane (OCM) reactor configured to receive oxygen ($O_2$) and methane ($CH_4$) and react the $O_2$ and $CH_4$ in an OCM process to yield a product stream comprising (i) $C_{2+}$ compounds including ethylene ($C_2H_4$) and (ii) carbon dioxide ($CO_2$); a first $CO_2$ separation unit fluidically coupled to the OCM reactor and configured to receive the product steam from the OCM reactor, wherein the first $CO_2$ separation unit separates at least some of the $CO_2$ from the product stream to produce an enriched stream comprising (i) the $C_{2+}$ compounds and (ii) at least some of the $CO_2$; a cryogenic separations unit fluidically coupled to the first $CO_2$ separation unit and configured to receive the enriched stream from the first $CO_2$ separation unit, wherein the cryogenic separations unit separates the $C_2H_4$ from the $C_{2+}$ compounds to produce an ethylene stream comprising (i) the $C_2H_4$ and (ii) the $CO_2$; and a second $CO_2$ separation unit fluidically coupled to the cryogenic separations unit and configured to receive the ethylene stream from the cryogenic separations unit, wherein the second $CO_2$ separation unit separates the $CO_2$ from the ethylene stream to produce an ethylene product stream.

In some embodiments of aspects provided herein, the enriched stream contains at most about 2.0 mol % $CO_2$. In some embodiments of aspects provided herein, the enriched stream contains at most about 1.0 mol % $CO_2$. In some embodiments of aspects provided herein, the enriched stream contains at most about 0.5 mol % $CO_2$. In some embodiments of aspects provided herein, the first $CO_2$ separation unit comprises a membrane, a pressure swing absorption (PSA) unit, an amine unit, or any combination thereof. In some embodiments of aspects provided herein, the second $CO_2$ separation unit comprises a membrane, a pressure swing absorption (PSA) unit, an amine unit, or any combination thereof. In some embodiments of aspects provided herein, the cryogenic separations unit comprises a de-methanizer.

Another aspect of the present disclosure provides a system for generating compounds with two or more Carbon atoms (C2+ compounds), comprising: an oxidative coupling of methane (OCM) reactor configured to receive oxygen ($O_2$) and methane ($CH_4$) and react the $O_2$ and $CH_4$ in an OCM process to yield a product stream comprising (i) $C_{2+}$ compounds including ethylene ($C_2H_4$) and (ii) carbon monoxide (CO) and/or carbon dioxide ($CO_2$); and a separations unit fluidically coupled to the OCM reactor and configured to receive the product stream from the OCM reactor, wherein the separations unit selectively separates olefins from the paraffins.

In some embodiments of aspects provided herein, the separations unit selectively separates ethylene from paraffins. In some embodiments of aspects provided herein, the separations unit comprises an absorber unit employing pi-complexation. In some embodiments of aspects provided herein, the separations unit comprises a membrane unit including a membrane contactor employing pi-complexation. In some embodiments of aspects provided herein, the separations unit comprises a pressure swing adsorption (PSA) unit comprising a sorbent having dispersed metal ions that are capable of complexing with the olefins. In some embodiments of aspects provided herein, the PSA unit comprises a sorbent selected from a zeolite, a molecular sieve sorbent, a carbon molecular sieve, an activated carbon, a carbon nanotube, and a polymeric resin. In some embodiments of aspects provided herein, the system further comprises an oxidizing agent used to regenerate and/or stabilize the pi-complex. In some embodiments of aspects provided herein, the oxidizing agent comprises $HNO_3$ or $KMnO_4$. In some embodiments of aspects provided herein, the separations unit comprises (i) a pressure swing adsorption (PSA) unit, (ii) a temperature swing adsorption (TSA) unit, or (iii) a membrane system employing a metal-organic framework (MOF), and the olefins separated comprise ethylene.

Another aspect of the present disclosure provides a system for generating compounds with two or more carbon atoms ($C_{2+}$ compounds), comprising: an oxidative coupling of methane (OCM) reactor configured to receive oxygen ($O_2$) and methane ($CH_4$) and react the $O_2$ and $CH_4$ in an OCM process to yield a product stream comprising (i) $C_{2+}$ compounds including ethylene ($C_2H_4$) and (ii) $C_1$ compounds including un-reacted $CH_4$; and a separations unit fluidically coupled to the OCM reactor and configured to receive the product stream from the OCM reactor, wherein the separations unit separates the $C_{2+}$ compounds from the $C_1$ compounds, and wherein the separations unit does not contain a de-methanizer.

In some embodiments of aspects provided herein, the separations unit contains a distillation column and an oil absorber. In some embodiments of aspects provided herein, the distillation column does not condense methane.

Another aspect of the present disclosure provides a system for generating compounds with two or more carbon atoms ($C_{2+}$ compounds), comprising: an oxidative coupling of methane (OCM) reactor configured to receive oxygen ($O_2$) and methane ($CH_4$) and react the $O_2$ and $CH_4$ in an OCM process to yield a product stream comprising (i) $C_{2+}$ compounds including ethylene ($C_2H_4$) and (ii) $C_1$ compounds including un-reacted $CH_4$; a pre-separations unit fluidically coupled to the OCM reactor and configured to receive the product stream from the OCM reactor, wherein the pre-separations unit produces (i) a bottoms stream comprising the $C_{2+}$ compounds and (ii) an overhead stream comprising the $C_1$ compounds and at least some of the $C_{2+}$ compounds; and an oil absorber fluidically coupled to the pre-separations unit and configured to receive the overhead stream from the pre-separations unit, wherein the oil absorber removes the at least some of the $C_{2+}$ compounds to produce a $C_1$ stream.

In some embodiments of aspects provided herein, the OCM process is integrated with a methanol to olefins (MTO) unit, a steam cracker, or a metathesis process. In some embodiments of aspects provided herein, the pre-separation unit does not include a de-methanizer. In some embodiments of aspects provided herein, the pre-separation unit does not condense methane. In some embodiments of aspects provided herein, the overhead stream comprises at least about 10% $C_{2+}$ compounds. In some embodiments of aspects provided herein, the overhead stream comprises at least about 5% $C_{2+}$ compounds. In some embodiments of aspects provided herein, the overhead stream comprises at least about 1% $C_{2+}$ compounds. In some embodiments of aspects provided herein, the overhead stream comprises at least about 0.1% $C_{2+}$ compounds.

Another aspect of the present disclosure provides a system for generating compounds with two or more carbon atoms ($C_{2+}$ compounds), comprising: an oxidative coupling of methane (OCM) reactor configured to receive oxygen ($O_2$) and methane ($CH_4$) and react the $O_2$ and $CH_4$ in an OCM process to yield a product stream comprising (i) $C_{2+}$ compounds including ethylene ($C_2H_4$) and (ii) $C_1$ compounds including un-reacted $CH_4$; and a separations unit fluidically coupled to the OCM reactor and configured to receive the product stream from the OCM reactor, wherein the separations unit contains a metal organic framework (MOF) that produces (i) a bottoms stream comprising the $C_{2+}$ compounds and (ii) an overhead stream comprising the $C_1$ compounds.

In some embodiments of aspects provided herein, the system further comprises a methanation unit fluidically coupled to the separations unit and configured receive the overhead stream from the separations unit, wherein the methanation unit converts carbon dioxide ($CO_2$) and/or carbon monoxide (CO) into methane ($CH_4$), and wherein the $CH_4$ is directed into the OCM reactor. In some embodiments of aspects provided herein, the system further comprises a second separations unit fluidically coupled to the separations unit and configured receive the bottoms stream from the separations unit, wherein the second separations unit contains a metal organic framework (MOF) that separates olefins from paraffins. In some embodiments of aspects provided herein, the separations unit comprises a pressure swing absorber (PSA) that contains the MOF. In some embodiments of aspects provided herein, the separations unit comprises a temperature swing absorber (TSA) that contains the MOF. In some embodiments of aspects provided herein, the $C_1$ compounds include hydrogen ($H_2$).

Another aspect of the present disclosure provides a system for generating compounds with two or more carbon atoms ($C_{2+}$ compounds), comprising: an oxidative coupling of methane (OCM) reactor configured to receive oxygen ($O_2$) and methane ($CH_4$) and react the $O_2$ and $CH_4$ to produce an OCM product stream, the OCM reactor having a catalytic section and a cracking section, which catalytic section reacts the $O_2$ and $CH_4$ to yield ethylene ($C_2H_4$), ethane ($C_2H_6$) and heat, which cracking section uses the heat to convert $C_2H_6$ into $C_2H_4$, and which product stream comprises (i) $C_{2+}$ compounds including ethylene ($C_2H_4$) and ethane ($C_2H_6$) and (ii) $C_1$ compounds including un-reacted $CH_4$; and a separations unit fluidically coupled to the OCM reactor and configured to receive the product stream from the OCM reactor, wherein the separations unit contains a metal organic framework (MOF) that produces (i) a first stream comprising the $C_2H_4$, (ii) a second stream comprising the $C_2H_6$ and (iii) a third stream comprising the $C_1$ compounds, and wherein the second stream and the third stream are directed into the cracking section and the catalytic section respectively.

In some embodiments of aspects provided herein, the third stream is directed to a methanation unit prior to directing to the catalytic section, which methanation unit converts carbon dioxide ($CO_2$) and/or carbon monoxide (CO) into methane ($CH_4$). In some embodiments of aspects provided herein, the separations unit comprises a pressure swing absorber (PSA) that contains the MOF. In some embodiments of aspects provided herein, the separations unit comprises a temperature swing absorber (TSA) that contains the MOF. In some embodiments of aspects provided herein, the $C_1$ compounds include hydrogen ($H_2$).

Another aspect of the present disclosure provides a non-transitory computer-readable medium comprising machine-executable code that, upon execution by one or more computer processors, implements any of the methods above or elsewhere herein.

Another aspect of the present disclosure provides a system comprising one or more computer processors and a non-transitory computer-readable medium coupled thereto. The non-transitory computer-readable medium comprises machine-executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

DETAILED DESCRIPTION

Figure 1:
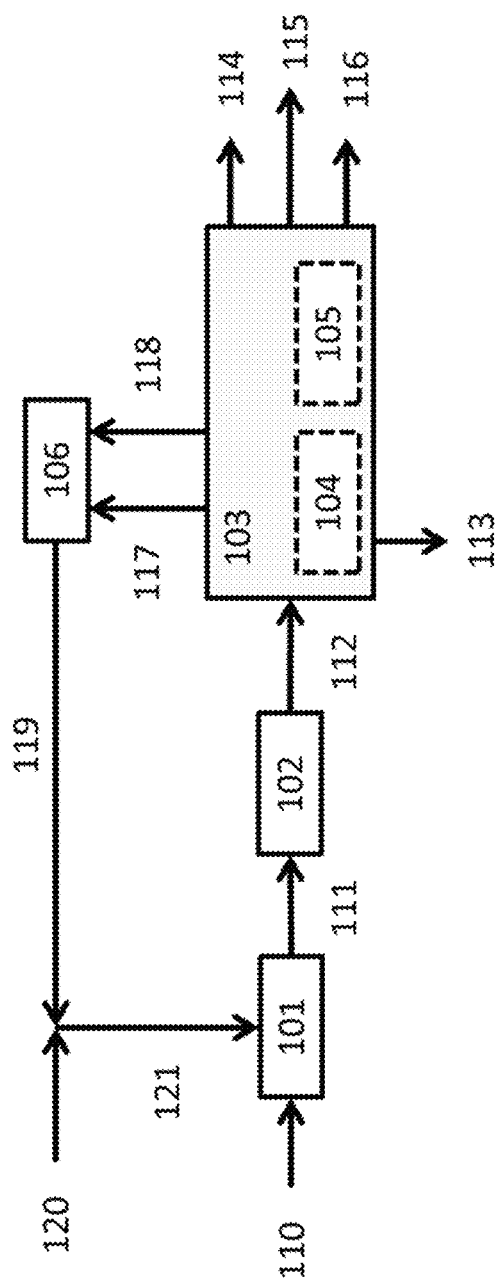
FIG. 1 shows an example oxidative coupling of methane (OCM) system with advanced separation.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "higher hydrocarbon," as used herein, generally refers to a higher molecular weight and/or higher chain hydrocarbon. A higher hydrocarbon can have a higher molecular weight and/or carbon content that is higher or larger relative to starting material in a given process (e.g., OCM or ETL). A higher hydrocarbon can be a higher molecular weight and/or chain hydrocarbon product that is generated in an OCM or ETL process. For example, ethylene is a higher hydrocarbon product relative to methane in an OCM process. As another example, a $C_{3+}$ hydrocarbon is a higher hydrocarbon relative to ethylene in an ETL process. As another example, a $C_{5+}$ hydrocarbon is a higher hydrocarbon relative to ethylene in an ETL process. In some cases, a higher hydrocarbon is a higher molecular weight hydrocarbon.

The term "OCM process," as used herein, generally refers to a process that employs or substantially employs an oxidative coupling of methane (OCM) reaction. An OCM reaction can include the oxidation of methane to a higher hydrocarbon and water, and involves an exothermic reaction. In an OCM reaction, methane can be partially oxidized and coupled to form one or more $C_{2+}$ compounds, such as ethylene. In an example, an OCM reaction is $2CH_4 + O_2 \rightarrow C_2H_4 + 2H_2O$. An OCM reaction can yield $C_{2+}$ compounds. An OCM reaction can be facilitated by a catalyst, such as a heterogeneous catalyst. Additional by-products of OCM reactions can include CO, $CO_2$, $H_2$, as well as hydrocarbons, such as, for example, ethane, propane, propene, butane, butene, and the like.

The term "non-OCM process," as used herein, generally refers to a process that does not employ or substantially employ an oxidative coupling of methane reaction. Examples of processes that may be non-OCM processes include non-OCM hydrocarbon processes, such as, for example, non-OCM processes employed in hydrocarbon processing in oil refineries, a natural gas liquids separations processes, steam cracking of ethane, steam cracking or naphtha, Fischer-Tropsch processes, and the like.

The terms "$C_{2+}$" and "$C_{2+}$ compound," as used herein, generally refer to a compound comprising two or more carbon atoms. For example, $C_{2+}$ compounds include, without limitation, alkanes, alkenes, alkynes and aromatics containing two or more carbon atoms. $C_{2+}$ compounds can include aldehydes, ketones, esters and carboxylic acids. Examples of $C_{2+}$ compounds include ethane, ethene, acetylene, propane, propene, butane, and butene.

The term "non-$C_{2+}$ impurities," as used herein, generally refers to material that does not include $C_{2+}$ compounds. Examples of non-$C_{2+}$ impurities, which may be found in certain OCM reaction product streams, include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "small scale," as used herein, generally refers to a system that generates less than or equal to about 250 kilotons per annum (KTA) of a given product, such as an olefin (e.g., ethylene).

The term "world scale," as used herein, generally refers to a system that generates greater than about 250 KTA of a given product, such as an olefin (e.g., ethylene). In some examples, a world scale olefin system generates at least about 1000, 1100, 1200, 1300, 1400, 1500, or 1600 KTA of an olefin.

The term "item of value," as used herein, generally refers to money, credit, a good or commodity (e.g., hydrocarbon). An item of value can be traded for another item of value.

The term "carbon efficiency," as used herein, generally refers to the ratio of the number of moles of carbon present in all process input streams (in some cases including all hydrocarbon feedstocks, such as, e.g., natural gas and ethane and fuel streams) to the number of moles of carbon present in all commercially (or industrially) usable or marketable products of the process. Such products can include hydrocarbons that can be employed for various downstream uses, such as petrochemical or for use as commodity chemicals. Such products can exclude CO and $CO_2$. The products of the process can be marketable products, such as $C_{2+}$ hydrocarbon products containing at least about 99% $C_{2+}$ hydrocarbons and all sales gas or pipeline gas products containing at least about 90% methane. Process input streams can include input streams providing power for the operation of the process. In some cases, power for the operation of the process can be provided by heat liberated by an OCM reaction. In some cases, the systems or methods of the present disclosure have a carbon efficiency of at least about 50%, at least about 55%, at least about 60%, at least about 65%, at least about 70%, at least about 75%, at least about 80%, at least about 85%, or at least about 90%. In some cases, the systems or methods of the present disclosure have a carbon efficiency of between about 50% and about 85%, between about 55% and about 80%, between about 60% and about 80%, between about 65% and about 85%, between about 65% and about 80%, or between about 70% and about 80%.

The term "$C_{2+}$ selectivity," as used herein, generally refers to the percentage of the moles of methane that are converted into $C_{2+}$ compounds.

The term "specific oxygen consumption," as used herein, generally refers to the mass (or weight) of oxygen consumed by a process divided by the mass of $C_{2+}$ compounds produced by the process.

The term "specific $CO_2$ emission," as used herein, generally refers to the mass of $CO_2$ emitted from the process divided by the mass of $C_{2+}$ compounds produced by the process.

The term "unit," as used herein, generally refers to a unit operation. A unit operation may be one or more basic steps in a process. A unit may have one or more sub-units (or sub-systems). Unit operations may involve a physical change or chemical transformation, such as separation, crystallization, evaporation, filtration, polymerization, isomerization, and other reactions. A unit may include one or more individual components. For example, a separations unit may include one or more separations columns or an amine unit may include one or more amine columns.

Separations

Various non-cryogenic separation techniques have been increasingly employed for gas separations, purifications and recovery of hydrocarbons. Membrane based processes and adsorbents have been intensively studied for large scale applications for olefins recovery. Since the development of synthetic adsorbents and pressure swing adsorption (PSA) cycles, adsorption has been playing an increasingly important role in gas separation and purification.

PSA technology can be used in a large variety of applications: hydrogen purification, air separation, $CO_2$ removal, noble gases purification, methane upgrading, n-iso paraffin separation and so forth. While new applications for gas separations by adsorption are continually being developed, the most important applications have been air separation (for production of $O_2$ and $N_2$) and hydrogen separation (from fuel gas). Approximately 20% of $O_2$ and $N_2$ are currently produced by PSA. The increasing industrial applications for adsorption have stimulated a growing interest in research and new applications.

Processes of the present disclosure can employ a variety of different separations techniques, alone or in combination. For example, OCM processes can employ amine and caustic systems for $CO_2$ removal, molecular sieve guard beds for water removal, and cryogenic distillation or other separation techniques for recovery and purification of hydrocarbon components. Cryogenic separation can refer to separations using temperature levels below 120 K or about −153° C. Other techniques include Selexol™ and Rectisol™ processes for $CO_2$ removal.

OCM product effluent can comprise a mixture of hydrocarbons including but not limited to methane, ethane, ethylene, propane, propylene, butanes, butenes, and higher hydrocarbons. OCM product effluent can also comprise varying amounts of other components such as $H_2$, $N_2$, CO, $CO_2$ and $H_2O$. The product of an OCM reaction can include ethylene. The ethylene product can be polymer grade, refinery grade or chemical grade. Depending on the purity level required, different separation and/or purification techniques can be employed with the OCM process. To recover high purity ethylene, separation methods such as those discussed herein can be used to remove a wide range of components.

Advantages of the advanced OCM processes described herein can include reducing the cost, reducing the number of unit operations ("units") used, and hence improving the overall process for producing high purity polymer grade ethylene. Overall conversion and carbon efficiency can also be improved. The separation methods disclosed herein can also improve the overall conversion and carbon efficiency.

The different separation and purification techniques discussed herein can be used to separate the OCM product effluent (e.g., process gas) into a plurality of streams, including but not limited to a first stream comprising methane, hydrogen, carbon monoxide and other lighter inerts and a second stream comprising ethane, ethylene, propylene, and higher hydrocarbons. Separation systems or subsystems employed can include those discussed herein, such as a cryogenic demethanizer, a membrane separation system, or a PSA based system.

The separation techniques discussed herein can be employed to remove $CO_2$, such as from an OCM product effluent stream. One or more separations techniques can be used to remove $CO_2$ including but not limited to absorption, adsorption, $CO_2$ distillation, and membrane separation. The separation technique can be non-cryogenic.

FIG. 1 shows a block flow diagram for an exemplary OCM process. Oxygen 110 and methane 121 can be fed into an OCM reactor 101 for conversion into higher hydrocarbon compounds including ethylene. The OCM product stream 111 can be directed to a compressor 102, and the compressed product stream 112 can be fed into a separations system 103. The separations system can include pretreatment units 104, such as impurity and $CO_2$ removal units, as well as separations units 105, such as cryogenic, non-cryogenic, complexation, membrane, and other separations units. The separations system can be a combination of more than one separation techniques, such as those discussed in this application. The separation system can replace $CO_2$ removal, moisture removal, and cryogenic separation systems of existing OCM process systems. The compressor system may not be required for some types of separation processes. From the separations system, $CO_2$ can be vented 113, ethane 114 can be recovered, for example for recycling to the OCM reactor, ethylene product 115 can be recovered, and $C_{3+}$ products 116 can be recovered. Additionally, $CO_2$ 117 and methane 118 can be directed from the separations system into a methanation unit 106. The methanation unit can produce methane from the $CO_2$, for recycling 119 back to the OCM reactor. Additional methane 120 can be added to the OCM reactor supply stream 121.

Auto Refrigeration

OCM process systems can use refrigeration subsystems to condense overhead vapors, for example from a demethanizer, a deethanizer, and/or a $C_2$ splitter. The temperatures employed can be in the range from about 12° C. to about −100° C. These low temperatures can be achieved through the use of multiple refrigeration systems, such as ethylene refrigeration and propylene refrigeration systems, to provide different levels of refrigeration. These can be similar to those employed in existing steam crackers.

Figure 2:
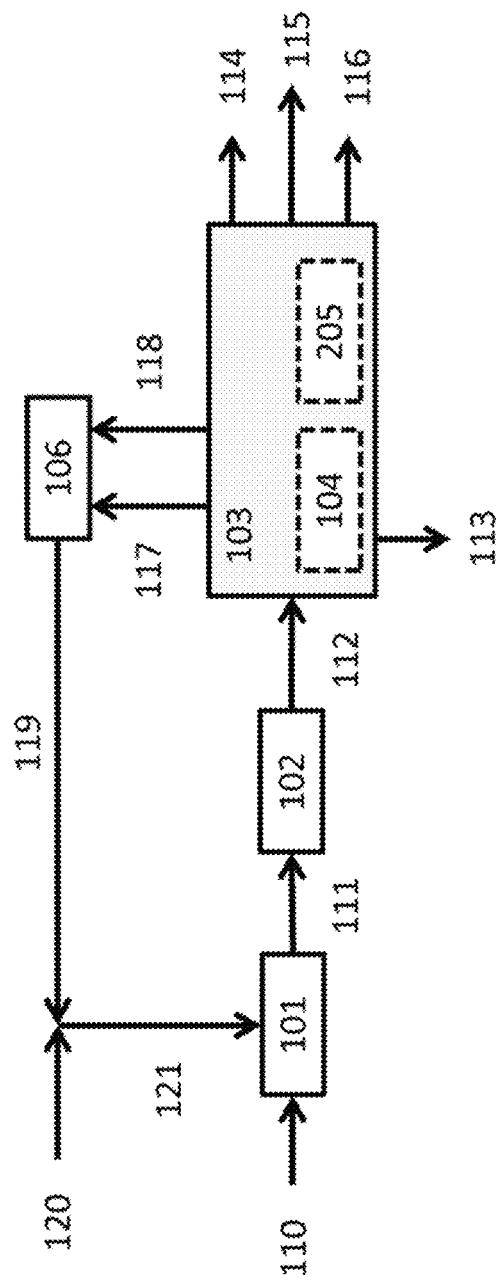
FIG. 2 shows an example OCM system with auto refrigeration (e.g., methane refrigeration)

Alternatively, an open loop methane refrigeration system can be employed to provide refrigeration for a demethanizer. OCM product effluent can comprise methane as the major component, for example at a concentration of at least about 50 mol %, 60 mol %, 70 mol %, 80 mol %, 90 mol %, or more. The demethanizer can have the lowest temperature requirements in the entire separations unit. Use of methane refrigeration (e.g., auto-refrigeration) can provide benefits such as elimination of the need for an additional refrigeration system (e.g., new) for any added capacity. For grass-roots or greenfield OCM applications, this can considerably reduce refrigeration compressor sizes needed. In some cases, an entire refrigeration system can be eliminated. FIG. 2 shows a block flow diagram for an exemplary open loop methane refrigeration system, such as can be used in gas processing plants and steam crackers to produce chilling for condensing overhead vapors from a demethanizer. Most elements of FIG. 2 correspond to the description in FIG. 1; the separations unit 205 can include an open loop methane refrigeration system to provide cooling for the separations. The system can be combined with a single or multiple stage (e.g., two-stage) expansion system (e.g., Joule Thompson) to chill the incoming feed. In certain cases, multiple separate lighter products are recovered, such as a light $H_2$-rich stream, a low pressure methane rich stream, and a high pressure methane rich stream.

Mixed Refrigeration

Another alternative to ethylene and propylene refrigeration subsystems is the use of a mixed refrigeration system. The mixed refrigerant can be, for example, a mix of methane, ethylene and propylene. The mixed refrigerant can be a mix of ethane and propane. A wide range of possible mixed refrigerants can be employed, and can be selected based on, for example, the availability of certain components and the degree of refrigeration required. A mixed refrigerant system can provide advantages for use with an OCM reactor system, including the use of only one refrigeration sub system. Rather than two refrigeration systems each comprising multiple stages of refrigerant compressor, associated vessels, exchangers, and other components, the process can use a single refrigeration system. This can substantially reduce capital cost. This can also reduce equipment count, which can be a benefit especially for OCM retrofits at places where plot space may be a concern.

Pi Complexation

Pi complexation techniques can be used to separate alkenes from alkanes. Some metal ions complex selectively with unsaturated organic compounds. Some of these complexes are reversible while others are irreversible. For example, aqueous silver salt in solution forms reversible complexes with olefins, and forms irreversible complexes with acetylenes. This property can be employed in an OCM process to recover ethylene and propylene from OCM reactor effluent.

Figure 3A:
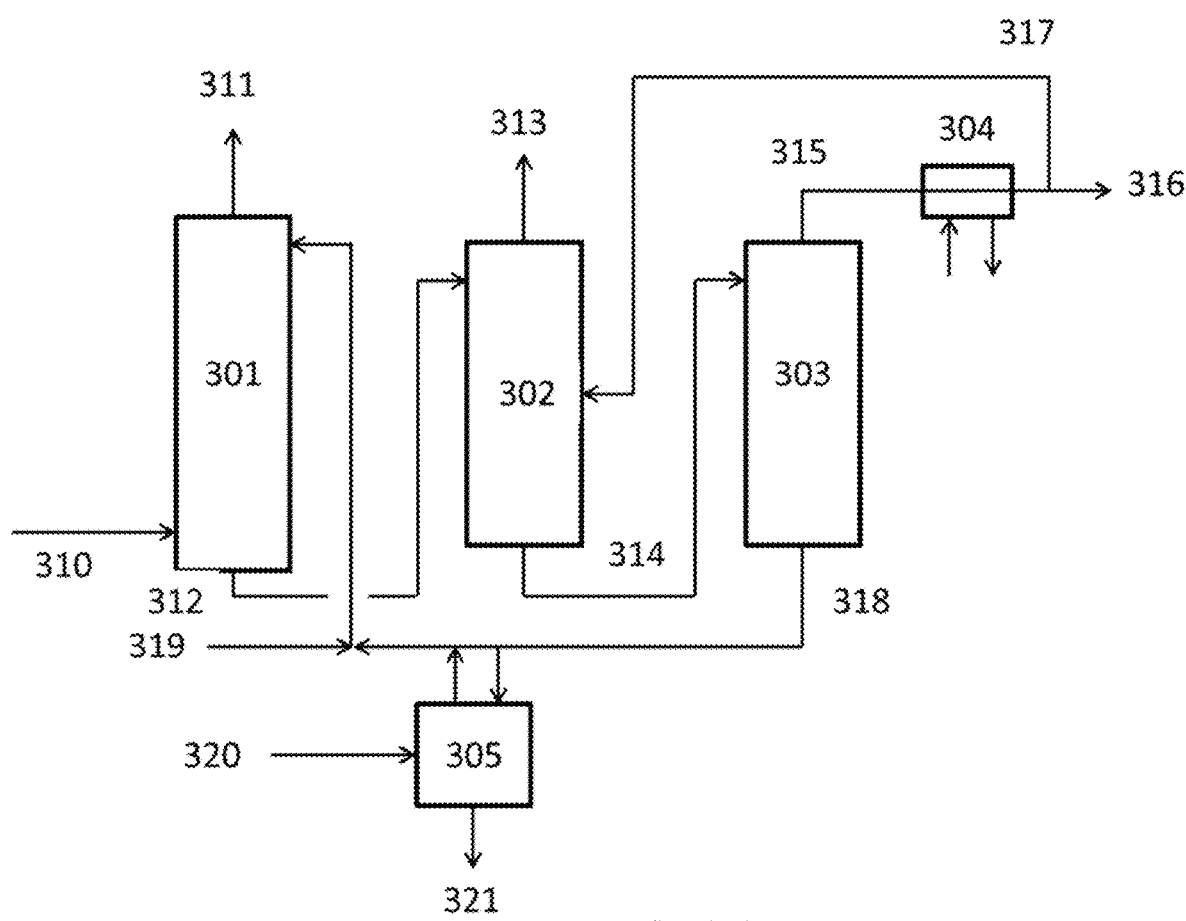
FIG. 3A shows an exemplary OCM system with a silver complexation ethylene recovery subsystem.

As shown in FIG. 3A, separation of ethylene and/or propylene by metal complexation can be divided into three major sections: absorption, purification or venting of impurities, and desorption. An exemplary process is provided for separation of ethylene and/or propylene from a purified multi-component gas stream from the OCM reactor. FIG. 3A shows a process for purifying a stream containing ethylene using an aqueous silver nitrate solution. Metal complexation (e.g., silver or cuprous ion complexation) can be used to separate ethylene and/or propylene from a purified multi-component gas stream produced via OCM comprising $C_2$ compounds, $C_3$ compounds, and lighter components such as hydrogen and nitrogen. First, the multi-component gas stream 310 can be introduced into an absorber 301 with aqueous silver salt solution, such that the ethylene and/or propylene undergo absorption or complexing with the silver metal ions, and such that trace acetylenes react with the silver metal ions. Vent gas 311 can be removed from the absorber. Then, the silver salt solution stream 312 can be vented 313 in a vent column 302 at reduced pressure to remove any dissolved low molecular weight components. Then, the resulting silver salt solution stream 314 can be treated in a stripper 303 to separate the absorbed or complexed ethylene and/or propylene from the silver salt solution 315, and further treated in a treatment unit 304 to release the trace acetylenes. Purified ethylene 316 can be recovered, and some product can be recycled 317. The aqueous silver salt stream 318 can then be recycled to the first step, in some cases after regeneration in a regeneration unit 305 with $AgMnO_4$ 320. $MnO_2$ 321 can be removed from the regeneration unit. $H_2O_2$ 319 can be added to the solvent stream being returned to the absorber.

Useful adsorbents include but are not limited to metal compounds, such as silver or copper, supported on high surface area carriers with a plurality of pores. These adsorbents can be used in pressure swing adsorption or temperature swing adsorption processes. When operating pressure and/or temperature is changed, the silver or copper compound can release the alkene-rich component from the adsorbent. These adsorbents can be very effective for selective adsorption of alkenes such as ethylene, propylene, and mixtures of these from gaseous mixtures.

When a gaseous component solubilizes in a liquid and complexes with its ions, the loading of the gas can be affected by its partial pressure and the temperature and the concentration of the complexing ions in the solution. Therefore, by changing the physical conditions separately or collectively, the active gaseous component can either be formed into or out of the solution. Adjusting or swinging one or more physical parameters can be used to carry out an ethylene or propylene separation using an aqueous silver nitrate solution. Purification or venting of impurities can result in a product stream that is free or substantially free of impurities including but not limited to $CO_2$, sulfur compounds, acetylenes, and hydrogen. Acetylene and hydrogen can cause operational problems and so the process gas can be treated to bring the concentration of such impurities to within an acceptable limit.

Metal complexation can be used in combination with other processes, such as membrane-based processes, or a PSA system with metal ions dispersed on the sorbent. For good adsorption, the cations can be spread (e.g., with high dispersion) on solid substrates with a high surface area. There are at least three types of metal complexation sorbents that can be used in the methods and systems described herein (i.e., monolayer or near monolayer salts supported on porous substrates, ion-exchange zeolites, and ion-exchange resins). For bulk separation, the monolayer salts on porous substrates and ion-exchange resins can be more suitable in some cases. Ion-exchange zeolites are usually more suitable for olefin recovery or purification. Substrates for supporting salts may include Y-Alumina (porous), silica gel, activated carbon, $TiO_2$, and a number of zeolites. The metal ion can be $Ag^+$ or $Cu^+$ ion.

Membrane contactors using a silver nitrate solution or a copper salt solution can be used to separate the olefins from the OCM effluent stream. The contactor can include the salt solution in a membrane module or unit. Many such modules or units can be put together in a contactor system where the salt solution is circulated. Such membrane contactors can result in substantial olefin recovery from a feed containing a mixture of olefins and paraffins (e.g., propane and/or propylene). The process described herein can be used to separate ethylene from the OCM effluent containing methane and ethane, resulting in elimination of whole, or part of the cryogenic recovery system in a typical OCM system.

As described herein, OCM process can be integrated with a Permylene membrane system to recover or separate the bulk of ethylene. In some cases, Permylene membranes can be used to separate olefins from paraffins. The Permylene process can use a flat sheet composite structure based on chitosan material and silver cations as facilitating agents. Chitosan can be produced by the deacetylation of chitin, which is the structural element in the exoskeleton of crustaceans. Chitosan can act as the active layer of the Permylene membrane. In contact with an aqueous solution containing silver ions, a hydrogel can be formed and the silver ions can form metal complexes with the olefins. The olefin molecules can be transported across the membrane under the influence of the olefin partial pressure differential between the feed and permeate sides of the membrane and can be released on the low pressure permeate side. Gases without a carbon-carbon double bond are rejected.

In some instances, an oxidizing agent can be used to either stabilize or improve the formation of the desired metal complex with olefin, and/or to regenerate or destabilize the undesired complexes formed. For example, in a copper based system, adding nitric acid can improve the stability of formation of the metal-olefin complex.

Figure 3B:
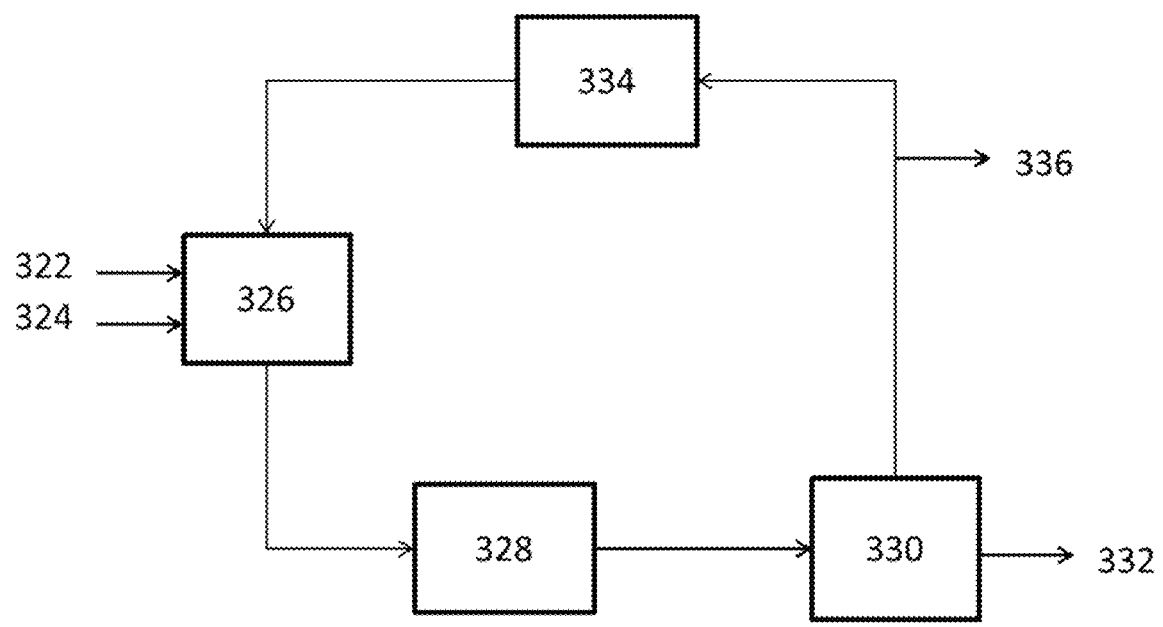
FIG. 3B shows an example of an OCM process with an integrated membrane contactor subsystem.
Figure 3C:
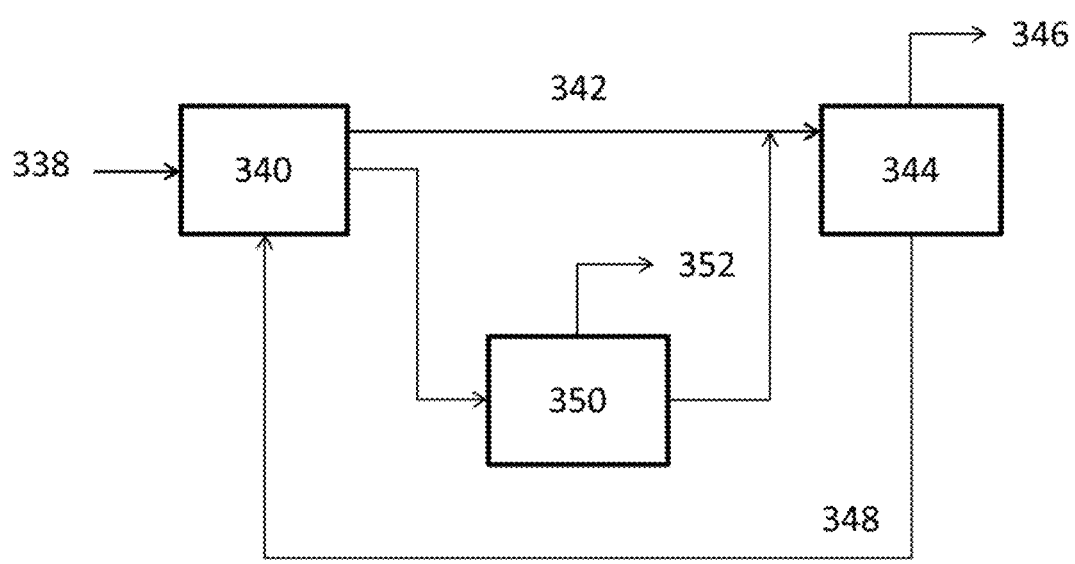
FIG. 3C shows an example of a membrane contactor.

FIG. 3B shows an example of a membrane contactor module (or unit) with an OCM system. The membrane contactor module separates the incoming feed into an olefin rich product stream and a lighter reject stream. The lighter stream can contain predominantly methane, CO, $CO_2$ and some ethane, and is recycled to the OCM loop (e.g., to methanation and back to OCM reactor). The pretreatment comprises acetylene and diene removal, since those are more active in forming metal-complexes than olefins. The lean (olefin depleted) solution can be recycled back to the membrane contactor, as shown in FIG. 3C. The metal complex can be subjected to a low pressure and/or a high temperature in order to break the olefin-metal complex and recover the olefin and metal solution.

FIG. 3B shows an example of an OCM process with an integrated membrane contactor module. The OCM feedstock 322 (e.g., comprising methane) and oxygen feed 324 (e.g., air) can be mixed and reacted in an OCM module 326. The OCM product can be pre-treated 328 and sent to a membrane contactor module 330. The membrane contactor module can provide an olefin-rich stream 332 and send some of the remaining material back to a methanation module 334. Some of the material can be purged 336. The methanation module 334 can produce methane and recycled to the OCM module 326.

FIG. 3C shows an example of a membrane contactor module. The feed 338 (e.g., from a pre-treatment unit 328) can go into a membrane unit 340. The olefin rich stream 342 can be sent to a first flash vessel 344, which produces an olefin product 346. The lean solution 348 (e.g., depleted in olefin) can be recycled to the membrane unit 340. In some cases, the membrane contactor module contains a second stage, in this example a second flash vessel 350 can produce a $C_1$ recycle stream 352.

Membranes

Membranes can be used to perform a variety of separations, such as separations of olefins and paraffins, or separations of $CO_2$. A membrane can be essentially a barrier that separates two phases and restricts transport of various chemicals in a selective manner. Polymer membranes can be used to separate mixtures such as propylene/propane mixtures and ethylene/butene mixtures. Separations in polymeric membranes are dependent on the solubility and diffusion of the species through the membrane. While zeolite-based separations are predominantly depended on molecular size differences, the differing permeation of olefins through a polymeric membrane can be largely attributed to differences in solubility, which can depend on the critical temperature and the kinetic diameter. Membrane separations can be employed even when there are small molecular size differences.

The OCM process can utilize a membrane based separation process to further enhance the efficiency and energy consumption of the process. Cryogenic distillation can be used for the separation of alkenes, but is highly energy intensive. Membrane based separations can be used for a variety of purposes in the context of an OCM process, such as to separate and purify ethylene product from OCM reactor effluent, to separate a stream rich in $CO_2$, to separate a stream containing lighter hydrocarbons and inerts, or to separate $C_2$ compounds from $C_1$ and lighter compounds.

Membranes can include but are not limited to isotropic membranes, anisotropic membranes, and electrically charged membranes. A membrane can be a ceramic membrane, a metal membrane, or a liquid membrane. An isotropic membrane can be a microporous membrane or a nonporous dense membrane. Membranes can be used for separations including but not limited to $CO_2$ separation, paraffin-olefin separation, or selective recovery of pure ethylene from the OCM reactor effluent. Polymer derived carbon molecular sieve membranes can be used to separate paraffins from olefins. These membranes can be used, for example, to separate ethylene from a mix of methane and ethane.

Membrane separations can be used in combination with other types of separation and purification subsystems to remove other impurities such as acid gases, hydrogen, and nitrogen.

Transport through a membrane can take place when a driving force is applied to the components in the feed. A driving force can be a pressure differential or a concentration (activity) gradient across the membrane. Membrane based separation techniques can be used in an OCM process by applying either of the above mentioned driving forces. A membrane based separation can also be a component of a hybrid separation set-up, such as a membrane and an absorption system (e.g., a membrane contactor) or a membrane in a pressure swing adsorption (PSA) or a temperature swing adsorption (TSA) system.

An OCM reactor can employ membranes as a part of the reactor system to effectively separate the ethylene product within the reactor system itself. A section of the reactor can include membranes that aid in recovering the ethylene product, with a methane rich stream being recycled to a methanation system and eventually to the OCM reactor. Such a system can also use advanced heat recovery or quench methods so as to facilitate the use of membranes.

Pressure Swing Adsorption (PSA) and Adsorption Technology

Cryogenic separation (e.g., distillation) can be used for the recovery of ethylene, propylene, and other components from olefin plants, refinery gas streams, and other sources. These separations can be difficult to accomplish because of the close relative volatilities, and can have significant temperature and pressure requirements for operation. The ethane/ethylene distillation can be performed at about −25° C. and 320 pounds per square inch gauge (psig) in a column containing over 100 trays. Distillation of propane and propylene can be performed at about −30° C. and 30 psig. These can be some of the most energy intensive distillations in the chemical and petrochemical industry. In general, the use of distillation towers to separate recover and purify components is an energy intensive process.

The present disclosure provides the use of adsorbents that can achieve separation and purification of olefin rich streams. In particular, the present disclosure applies the use of PSA-based adsorbent systems to separate, purify, and recover olefins like ethylene and propylene from streams containing one or more impurities such as methane, hydrogen, carbon monoxide, carbon dioxide, ethane, or others. The streams, or parts of the streams, can be generated via an OCM process, an ETL process, or combinations thereof. The streams can be final product streams where PSA is used to recover and purify the final product. The streams can be intermediate streams which are purified prior to use as a feed in a subsequent process, such as an ETL process, an ethylene cracker (steam cracker), a refining unit, a fuel gas system, a natural gas recovery plant or any other product fractionation or product treatment unit.

Pressure Swing Adsorption (PSA)

A pressure swing adsorption (PSA) process cycle is one in which desorption takes place at a different (e.g., lower) pressure than the adsorption pressure. Reduction of pressure can be used to shift the adsorption equilibrium and affect regeneration of the adsorbent. Low pressure may not be as effective as temperature elevation in totally reversing adsorption, unless very high feed to purge pressure ratios are applied. Therefore, most PSA cycles are characterized by high residual loadings and thus low operating loadings. These low capacities at high concentration require that cycle times be short for reasonably sized beds (e.g., seconds to minutes). These short cycle times are attainable because particles of adsorbent respond quickly to changes in pressure. Major uses for PSA processes include purification as well as applications where contaminants are present at high concentrations.

Figure 4:
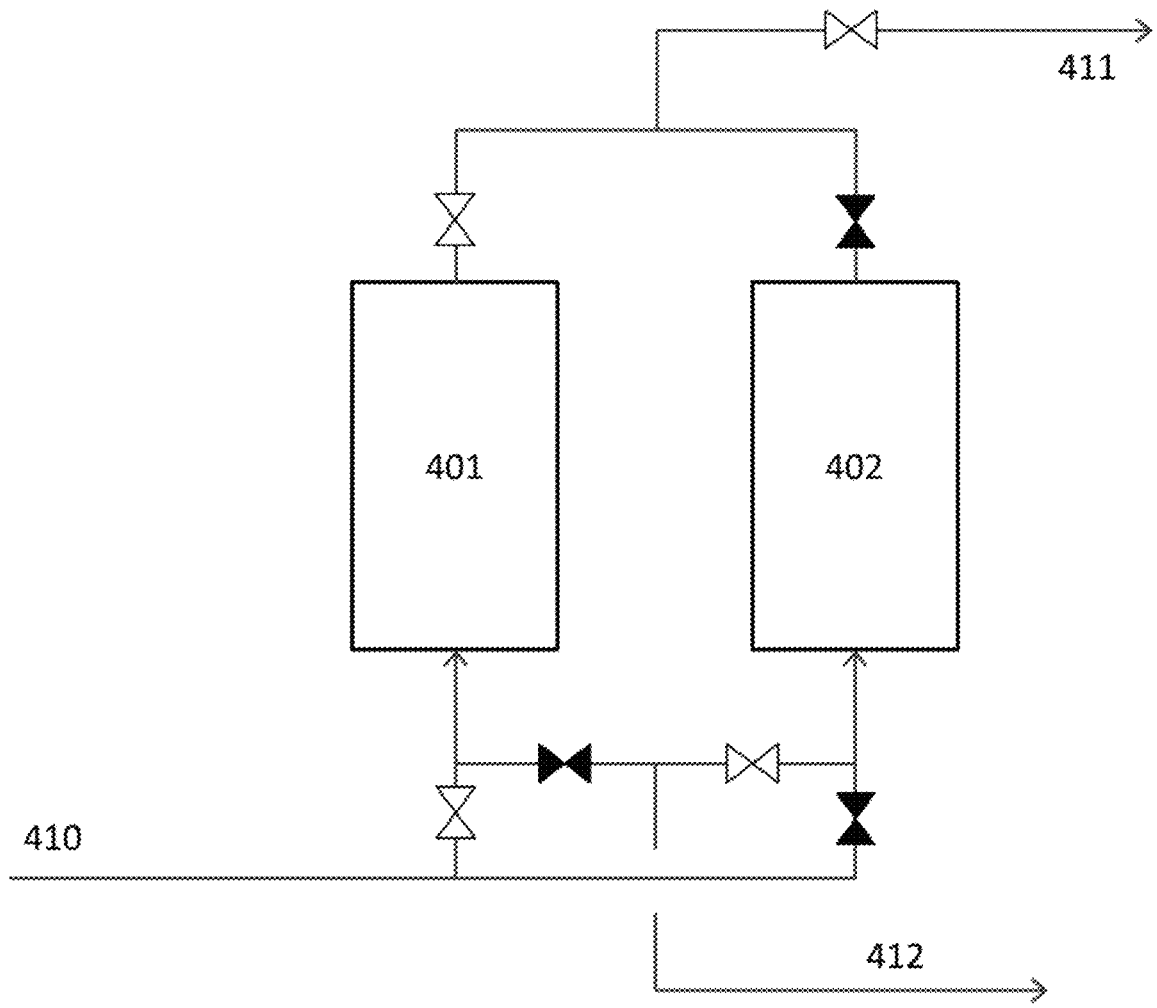
FIG. 4 shows an exemplary pressure swing adsorption (PSA) system.

As shown in FIG. 4, the PSA system can comprise two fixed bed adsorbers 401 and 402 undergoing a cyclic operation of four steps—adsorption, blowdown, purge, and pressurization. The PSA system can receive a feed 410 and produce a product stream 411, with a PSA off gas stream 412. For improving the performance of the basic Skarstrom™ cycle (FIG. 4), additional operation steps can be employed such as pressure equalization, product pressurization, and co-current depressurization. Besides these steps, the number of beds can be modified to achieve the optimal operation and multi-bed processes can be used in commercial applications like hydrogen recovery. Similarly, a TSA system can be used where a swing in temperature causes the sorption and desorption.

PSA cycles are used primarily for purification of wet gases and of hydrogen. High pressure hydrogen employed in processes such as hydrogenation, hydrocracking, and ammonia and methanol production can be produced by PSA beds compounded of activated carbon, zeolites and carbon molecular sieves. Other exemplary applications include: air separation, methane enrichment, iso/normal separations, and recovery of CO and $CO_2$.

Adsorbents

Adsorbents can be natural or synthetic materials, such as those having amorphous or microcrystalline structure. Exemplary adsorbents useful for large scale operation include but are not limited to activated carbon, molecular sieves, silica gels, and activated alumina. Other useful adsorbents include pi complexation sorbents, silver and copper complexation adsorbents, zeolites, synthetic zeolites, mesoporous materials, activated carbons, high surface area coordination polymers, molecular sieves, carbon molecular sieves (CMS), silica gels, MCM, activated alumina, carbon nanotubes, pillared clays, and polymeric resins.

For systems where the incoming stream is a multi-component mixture of gases and the number of compounds to be separated cannot be removed by a single adsorbent, different layers of adsorbents can be used. For example, hydrogen purification from a methane stream in a reforming operation, where $H_2$ is contaminated with $H_2O$, $CO_2$, CO, and unconverted $CH_4$, can employ activated carbon to remove $H_2O$ and $CO_2$ in combination with additional layers of different adsorbents used to increase the loading of CO.

Zeolites, molecular sieves, and carbon molecular sieves (CMS) can be used for most industrial separations employing PSA. Inorganic materials, like special kinds of titano-silicates, can be used for kinetic separations.

For systems specifically configured to separate ethane/ethylene and propane/propylene, exemplary types of adsorbents include zeolites/molecular sieves and pi complexation sorbents. Zeolites/molecular sieves can be used for kinetic separation, such as separation based on higher diffusivity of olefins over that of paraffins. The use of 4A zeolite is one such example. For example, a three-bed system can be used to recover olefins from a stream containing 80-85% olefins and 10-15% paraffins, using a 4A type zeolite at elevated temperatures (e.g., the Petrofin process). Pi complexation sorbents, such as $AgNO_3/SiO_2$, can give excellent results as compared to 4A zeolite. PSA units as discussed herein can employ a range of different sorbents, including but not limited to a zeolite/molecular sieve sorbent, a pi complexation based sorbent, a carbon molecular sieve sorbent or any other form of activated carbon, carbon nanotubes, polymeric resin based sorbents, or other sorbents.

Adsorbents can be selected based on a number of different criteria. Adsorbent selection criteria can include capacity for the target components (e.g., affinity for the desired components to be separated from the multi-component feed stream), selectivity between components competing for same adsorption sites, regenerability of the adsorbent, (e.g., the ability of the adsorbent to release the adsorbed target components at a reasonable pressure rate of gas diffusion into the adsorbent—this can also affect the size of the bead that is chosen and consequently the pressure drop across the bed; an insufficient diffusion rate can require smaller diameter beads that can result in higher pressure drop and hence increased operating costs), and chemical compatibility (e.g., selecting an adsorbent resistant to chemical attack that may poison or destroy the adsorbent, such as liquid hydrocarbons causing physical breakdown of the adsorbent resulting in loss of efficiency and back pressure).

Separations, such as of ethylene and propylene, can be conducted using an amorphous fluoropolymer based membrane. Facilitated transport using silver ions can selectively transport ethylene and/or propylene. The membrane can be a part of a membrane contactor system. The feed to the system can be of a low to moderate olefin concentration. The feed to the system can contain other hydrocarbons, including, but not limited to, methane, ethane, propane, butane, butenes, $C_5$ components and higher hydrocarbons. The feed can also contain $CO_2$, CO, $H_2$, and inert components, such as nitrogen.

$CO_2$ Separation

There are many technologies available for $CO_2$ capture, such as from flue gases, natural gas, or from any process gas rich in $CO_2$. Various processes for post-combustion or pre-combustion capture can be used reduce $CO_2$ emissions. FIG. 5A, FIG. 5B, FIG. 5C, and FIG. 5D show exemplary schematics of different separation methods available to separate $CO_2$ from a process gas or a flue gas.

Figure 5A:
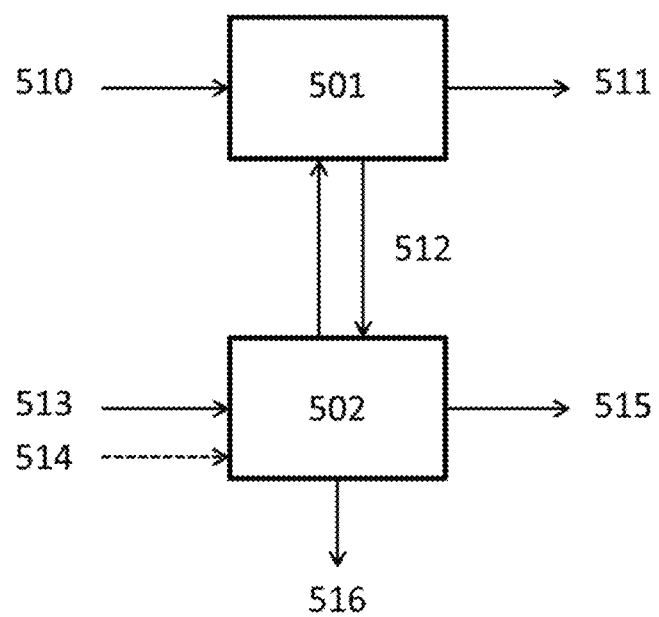
FIG. 5A shows a schematic of $CO_2$ separation methods.

OCM processes can utilize an amine based absorption system for $CO_2$ removal, which can be followed by use of a caustic scrubber to obtain high degree of separation. The amine system is prone to corrosion, solvent degradation, and above all, has high energy requirements. Separations with sorbents and/or solvents can involve placing the $CO_2$ containing gas in intimate contact with a liquid absorbent or a solid sorbent that is capable of capturing the $CO_2$. As shown in FIG. 5A, a stream with $CO_2$ 510 can be directed into a capture vessel 501, where it contacts sorbent which captures $CO_2$ from the stream. The stream, with reduced or removed $CO_2$, can then exit 511 the vessel. Sorbent 512 loaded with captured $CO_2$ can be transferred to a sorbent regeneration vessel 502 where it releases the $CO_2$ after being heated (e.g., with the use of energy 513), after a pressure decrease, or after any other change in the conditions around the sorbent, thereby regenerating the sorbent. Spent sorbent 515 and $CO_2$ 516 can be removed from the vessel, and make up sorbent 514 can be added. After the regeneration step the sorbent can be sent back to capture more $CO_2$ in a cyclic process. The sorbent can be a solid. Solid sorbent can remain in a single vessel rather than being cycled between vessels; sorption and regeneration can be achieved by cyclic changes (e.g., in pressure or temperature) in the vessel where the sorbent is contained. A make-up flow of fresh sorbent can be used to compensate for natural loss of activity and/or sorbent losses.

Amine scrubbing technology can be used to remove acid gases from process gases. Primary amines (e.g., MEA, DGA), secondary amines (e.g., DEA, DIPA), tertiary (e.g., MDEA, TEA), sterically hindered amines, chilled ammonia, potassium carbonate, and other compounds can be used to remove $CO_2$ from process gases. Traditional amine based systems can be characterized by high energy requirements and solvent degradation. Improved solvents, which can require less energy for regeneration of the solution, include the Benfield process and two stage diethanolamine. Combination with an OCM process can reduce the energy consumption of amine scrubbing processes. Improved solvents can reduce the energy requirements by as much as 40% compared to the traditional MEA solvents. This has the potential of reducing the energy, and hence steam, consumption of the OCM process, thereby increasing the amount of steam available for export from the OCM, or making alternative waste heat recovery methods feasible.

Physical absorption solvents used can include but are not limited to glycol dimethylethers (e.g., Selexol) and propylene carbonate (e.g., IPTS/EC). Regeneration of the solution can be performed by vacuum flashing and air stripping; this approach can consume significantly less energy than in chemical absorption. In using physical solvents $CO_2$ can be released mainly by depressurization, thereby avoiding the high heat of consumption of amine scrubbing processes.

Mixed or hybrid solvents can include but are not limited to Sulfinol (sulfolane, water, and amine), such as Sulfinol-M and Sulfinol-X.

Solid adsorbents, such as zeolites and activated carbon, can be used to separate $CO_2$ from gas mixtures. In pressure swing adsorption (PSA), a gas mixture can flow through a packed bed of adsorbent at elevated pressure until the concentration of the desired gas approaches equilibrium. The bed can be regenerated by reducing the pressure. In temperature swing adsorption (TSA), the adsorbent can be regenerated by raising its temperature. In general usage, adsorption is not yet considered attractive for large scale separation of $CO_2$ because the capacity and $CO_2$ selectivity of available adsorbents are low. However, when the OCM process is a recycle process, an adsorbent based separation method can be used to separate bulk $CO_2$ followed by consuming the remaining $CO_2$ in a methanation reactor system, or by using a caustic scrubber to treat the remaining $CO_2$.

Figure 5B:
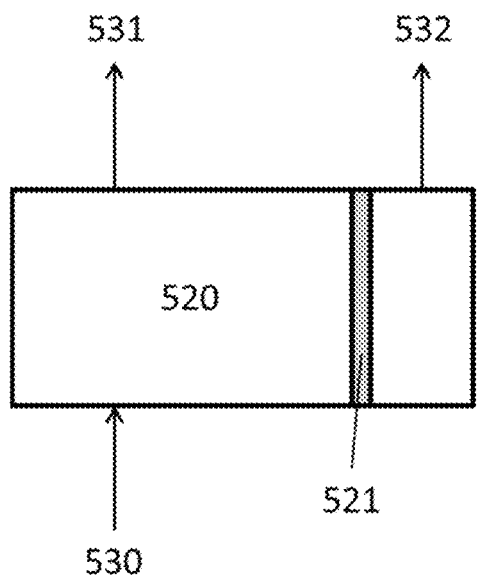
FIG. 5B shows a schematic of $CO_2$ separation methods.

Many different types of membrane materials (e.g., polymeric, metallic, ceramic) can be used for $CO_2$ capture to preferentially separate $CO_2$ from a range of process streams. FIG. 5B shows an exemplary schematic of separation of $CO_2$ from a gas stream 530 in a separation vessel 520 using a membrane 521. $CO_2$ can be removed from the stream via the membrane, and $CO_2$ and other gases can exit the vessel in separate streams 531 and 532. The main limitation of currently existing membranes is the occurrence of severe plasticization of the membrane in the presence of high pressure $CO_2$. Due to excessive swelling of the polymer membrane upon exposure to $CO_2$, the performance (e.g., selectivity) can decrease significantly, thus reducing the purity of the $CO_2$ and consequently reducing the possibilities for reuse of the gas. Energy requirements can be significantly lower for membrane based technologies; for example, membrane technology can use 70-75 kWh per ton of recovered $CO_2$ compared to significantly higher values for pressure swing adsorption (e.g., 160-180 kWh), cryogenic distillation (e.g., 600-800 kWh), or amine absorption (e.g., 330-340 kWh), making membrane technology an attractive option for integration with OCM for $CO_2$ separation.

Membrane and amine technologies can be combined to form a hybrid process to capture $CO_2$. Micro-porous hollow fiber membranes can be used for $CO_2$ separation using amine-based chemical absorption processes. Micro-porous membranes can be used in a gas-liquid unit where the amine solution is contacted with $CO_2$ containing gas. Using the membrane can lead to a reduction in the physical size and weight of the gas-liquid contacting unit. The separation is based on reversible chemical reaction, and mass transfer occurs by diffusion of the gas through the gas/liquid interface as in traditional contacting columns. Such a hybrid membrane contactor can provide a high contact area between gas and liquid, reduce or essentially eliminate foaming and flooding problems, and give better operational flexibility while reducing solvent degradation problems.

A membrane contactor can combine the advantages of membrane technology and solvent absorption for $CO_2$ separation. A membrane contactor is a combination of advanced membrane techniques with an effective absorption process. A membrane contactor is a hybrid mass exchanger where a porous membrane separates two phases. The selective sorbent performs the separation while the membrane facilitates the mass exchange process by expanding the phase contact surface area. The modified surface properties can improve the selectivity of the process by selectively inhibiting the transport of one of the mixture constituents. Compared to a conventional column device, membranes can allow for up to five times increase in yield per unit volume. Since the sorptive liquid flows within capillaries and both phases are not directly contacting each other, membrane absorbers can operate in any spatial configuration (horizontal or vertical) and at any flux rations between both phases. Also, there is no flooding or uneven packing moisturization. Since the system operates with unchanging yields, independent of the diameter and height; scaling up is fairly simple. Membranes used can be micromembranes or ultrafiltration membranes made a variety of different polymer and ceramic materials. Polypropylene fiber membranes can be used to separate $CO_2$ from $CH_4$, for example by using amines like MEA as absorption liquid. Hollow fiber membranes, such as porous polypropylene, perfluoroalkoxy (PFS), and asymmetric poly (phenylene oxide) hollow fiber membranes with a dense ultrathin skin at the outside of the membrane can also be used. Besides amines as absorption liquid, other absorption liquids may be used, such as aqueous sarcosine salt solutions, for example in a gas-liquid membrane contactor system. A membrane contactor can be used to separate the $CO_2$ from the OCM effluent in which $CH_4$ is the major component. Membrane contactors can also be used for separation of olefins and paraffins, and the separation of $CO_2$ from light gases.

An activator, such as piperazine, diethanolamine, and arsenic trioxide, can be used to further enhance the effectiveness of $CO_2$ capture. DGA and tertiary amines may provide more improvement than primary or secondary amines.

Gas selective poly ionic liquid membranes, which are polymerized room temperature ionic liquids (RTIL), can be used to be highly selectively separate $CO_2$. RTILs can be synthesized as a monomer and subsequently polymerized to obtain gas selective membranes. The ionic nature of the polymers can result in tight arrangements between the oppositely charged ionic domains in the poly RTIL, which can eventually prevent the membrane from excessive swelling and deterioration of its performance at increased pressure and/or temperature. This intrinsic property of poly RTIL can be used to increase the resistance against plasticization and to restrict strong swelling of the polymer membrane to maintain its permeation properties in the presence of a strong plasticizing agent such as $CO_2$ at higher pressures. For example, an imidazolium-based poly RTIL can be used as base material and the length of the alkyl chain can serves to strengthen or weaken the ionic interactions within the poly RTIL. High pressure mixed $CO_2/CH_4$ gas separation measurements at different temperatures.

Gas components like $CO_2$, from $N_2$ or $CH_4$ can be separated with supported ionic liquid membranes. Ionic liquids are molten salts with a very low melting point (many are liquids at room temperature). Many ionic liquids show a high solubility for carbon dioxide and hence can be highly suitable for use with an OCM process. For example, ionic liquids can include but are not limited to imidazolium, pyrollidinium, pyridinium, cuanidinium, phosphonium, morpholinium, piperidinium, sulfonium, ammonium, hexafluorophosphate, tetraflouroborate, alkylsulphate, triflate, dicyanamide, bis(trifluoromethylsulfonyl)imide, and combinations thereof. Specific advantages of ionic liquids include very low to negligible vapor pressure, good dissolution characteristics for many substances, and lack of flammability or toxicity. Ionic liquids can have good thermal, mechanical and chemical stability as well as favorable densities and viscosities. The required specifications can be adjusted easily by the large number of possible combinations of anions and cations when formulating an ionic liquid. Ionic liquids can be used as chemical solvents, catalysts, electrolytes in fuel cells as well as for gas-separation and storage by absorption. Ionic liquid membrane systems can comprise an adequate porous support material, e.g. a polymer film, coated by ionic liquids. The system can separate $CO_2$ and sulfur compounds from different gas mixtures. Competitive selectivity and permeability are obtained for the separations.

Novel membrane materials, such as polyetherimides, can be used as membrane material with improved plasticization resistance for $CO_2$ removal, for example with an OCM process. Other membrane materials that can be used include, but are not limited to, polymeric membranes based on or comprising polyamides, poly semicarbazides, polycarbonates, polyarylates, polyaniline, poly(phenylen oxide), polysulfones, polypyrrolones, or combinations thereof. In some cases, the polymeric membrane is solvent resistant and can reduce the plasticization effects of hydrocarbons in the feed stream, e.g., polyketone, polyether ketone, polyarylene ether ketone, polyimide, polyetherimide, and/or polyphenylene sulphide, which have intrinsic solvent inertness and can therefore withstand organic rich operation conditions.

An adequate porous support material, e.g. a polymer film, coated by ionic liquids can be used in continuous separation of $CO_2$ and sulfur compounds from different gas mixtures, including a methane rich stream. This separation can improve the efficiency of OCM processes. The OCM reactor effluent can enter the supported ionic liquid separation subsystem, and $CO_2$ and other contaminants can be removed from the process gas. Other contaminants can include but are not limited to traces of sulfur compounds, inerts, CO, $SO_2$, $H_2S$, and tetrahydrothiophene (THT).

Figure 5C:
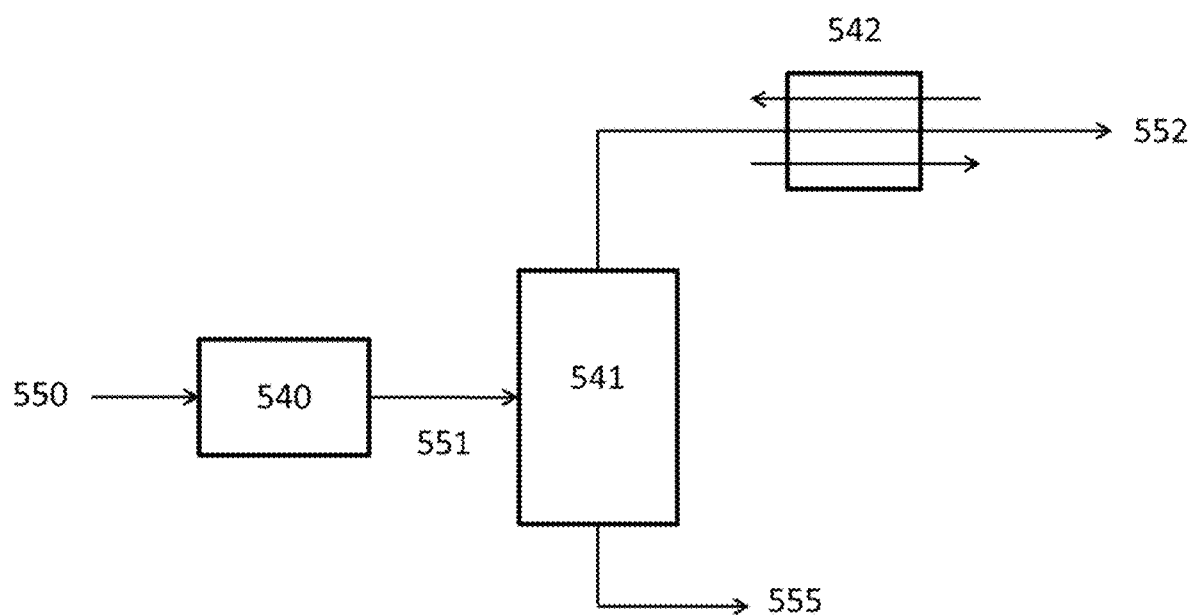
FIG. 5C shows a schematic of $CO_2$ separation methods.

$CO_2$ can be separated from other gases by cooling and condensation, for example as shown in FIG. 5C. A stream containing $CO_2$ 550 can be compressed in a compressor 540, and the compressed stream 551 can be directed to a distillation column 541. Some components can be recovered from the overhead stream 552, with heat recovered in a heat exchanger 542. Other components can be recovered from the bottoms 555. Cryogenic separation is widely used commercially for streams that already have a high concentration of $CO_2$ (typically greater than 90%). Cryogenic separation of $CO_2$ has the advantage that it enables direct production of high purity liquid $CO_2$ that can be used as a feedstock to convert the carbon to higher value hydrocarbons, or otherwise be captured. The amount of energy required can be high, and water may need to be removed before the feed gas is cooled.

Low temperature distillation can give better results when there is a high concentration of $CO_2$ in the feed gas. For the OCM process gas, the $CO_2$ concentration can be increased by, for example, having a recycle stream, or by using a modified OCM reactor where excess $CO_2$ is used as a quench medium for the reaction heat. Low temperature separation can refer to separations using temperature levels above $-90°$ C.

Figure 5D:
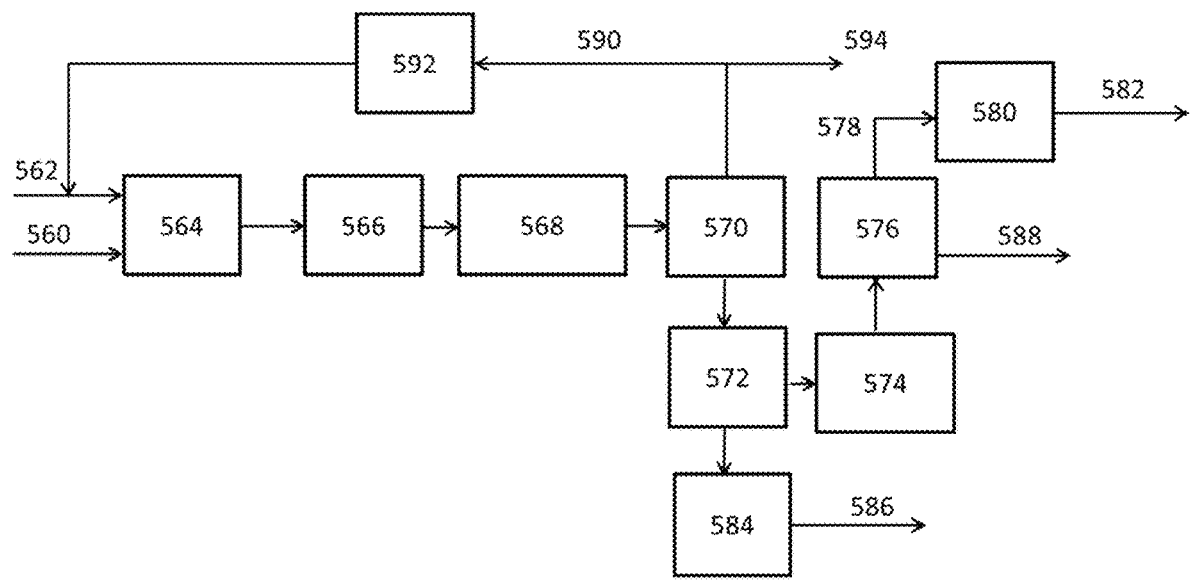
FIG. 5D shows a schematic of $CO_2$ separation methods.

As shown in FIG. 5D, another method of the present disclosure for removing $CO_2$ from the OCM system involves a two-step $CO_2$ removal. The first step can be a bulk $CO_2$ removal, followed by the recovery section (e.g., cryogenic fractionation system), and then a second polishing step to remove the $CO_2$ from the purified ethylene product to meet the polymer grade ethylene specifications.

As shown in FIG. 5D, oxygen 560 can be fed with methane 562 into an OCM reactor 564. The effluent can be compressed 566. The first (bulk) $CO_2$ removal 568 can be carried out before the cryogenic section. The first $CO_2$ removal lowers the $CO_2$ content to a level tolerable in the cryogenic de-methanizer 570. The demethanizer is operated at conditions that ensure that no $CO_2$ freezes and all of the residual $CO_2$ that is not removed in the bulk separation 568 is separated with the heavy $C_{2+}$ stream at the bottom and sent to the de-ethanizer 572. An acetylene hydrogenation system 574 and a $C_2$ splitter 576 can follow the de-ethanizer 572 to produce high purity ethylene 578. The high purity ethylene can contain the residual $CO_2$ that is not removed by the first $CO_2$ removal unit 568. This residual $CO_2$ can be removed by a second $CO_2$ removal step 580 to produce polymer grade ethylene 582. In some cases, a depropanizer 584 can be used to produce a $C_{3+}$ product 586, ethane 588 can be recycled to (the cracking section of) the OCM reactor 564, and $C_1$ compounds 590 can be methanated 592 and returned to the OCM reactor 564 or purged 594. In some cases $CO_2$ from the first 568 or second 580 $CO_2$ removal units can be send to the methanation reactor 592 (not shown).

The first (bulk) $CO_2$ separations system can be a membrane or a PSA system, an amine removal system, or any other solvent based $CO_2$ removal system as described herein. The final $CO_2$ removal step can be a caustic tower, a membrane based system, a PSA based system, or any other $CO_2$ removal system as described herein. The ethylene product $CO_2$ removal system 580 can be followed by further drying and/or purification steps.

One advantage of the two step process described herein can be energy saving that arise from decreasing the gas volumes being processed for the final $CO_2$ removal step. If $CO_2$ removal is done entirely upstream of the demethanizer, the energy consumption is much greater than described in FIG. 5D because the entire methane rich recycle stream dilutes the $CO_2$. When final $CO_2$ removal is performed at the back-end, the ethylene product has a far lower flow rate and hence the final $CO_2$ removal step is more energy efficient.

The concentration of $CO_2$ going into the de-methanizer (following the first $CO_2$ removal unit) can be any suitable amount (i.e., such that $CO_2$ doesn't freeze in the de-methanizer). In some embodiments, the concentration of $CO_2$ going into the de-methanizer is about 0.1 mol %, about 0.2 mol %, about 0.3 mol %, about 0.4 mol %, about 0.5 mol %, about 0.6 mol %, about 0.7 mol %, about 0.8 mol %, about 0.9 mol %, about 1.0 mol %, about 1.2 mol %, about 1.4 mol %, about 1.6 mol %, about 1.8 mol %, about 2.0 mol %, about 2.2 mol %, about 2.4 mol %, about 2.6 mol %, about 2.8 mol %, about 3.0 mol %, about 3.5 mol %, about 4.0 mol %, or about 5.0 mol %. In some cases, the concentration of $CO_2$ going into the de-methanizer is at least about 0.1 mol %, at least about 0.2 mol %, at least about 0.3 mol %, at least about 0.4 mol %, at least about 0.5 mol %, at least about 0.6 mol %, at least about 0.7 mol %, at least about 0.8 mol %, at least about 0.9 mol %, at least about 1.0 mol %, at least about 1.2 mol %, at least about 1.4 mol %, at least about 1.6 mol %, at least about 1.8 mol %, at least about 2.0 mol %, at least about 2.2 mol %, at least about 2.4 mol %, at least about 2.6 mol %, at least about 2.8 mol %, at least about 3.0 mol %, at least about 3.5 mol %, at least about 4.0 mol %, or at least about 5.0 mol %. In some cases, the concentration of $CO_2$ going into the de-methanizer is at most about 0.1 mol %, at most about 0.2 mol %, at most about 0.3 mol %, at most about 0.4 mol %, at most about 0.5 mol %, at most about 0.6 mol %, at most about 0.7 mol %, at most about 0.8 mol %, at most about 0.9 mol %, at most about 1.0 mol %, at most about 1.2 mol %, at most about 1.4 mol %, at most about 1.6 mol %, at most about 1.8 mol %, at most about 2.0 mol %, at most about 2.2 mol %, at most about 2.4 mol %, at most about 2.6 mol %, at most about 2.8 mol %, at most about 3.0 mol %, at most about 3.5 mol %, at most about 4.0 mol %, or at most about 5.0 mol %. In some cases, the concentration of $CO_2$ going into the de-methanizer is between any of the two values described above, for example, between about 0.5 mol % and about 2.0 mol %.

Figure 6:
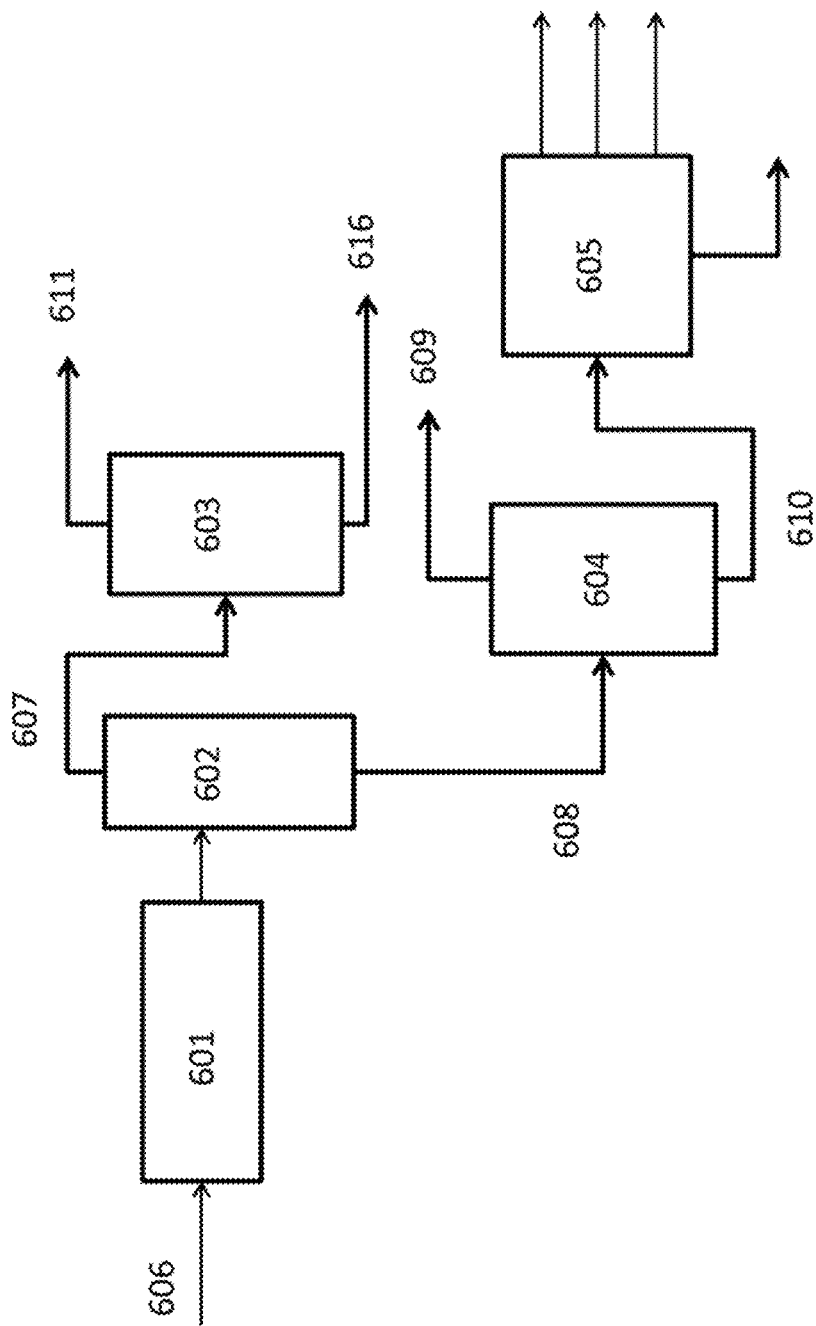
FIG. 6 shows an example $CO_2$ distillation system.

FIG. 6 shows a schematic of $CO_2$ separation using distillation. OCM reactor effluent 606 can be fed to a treatment unit 601, such as a molecular sieve dryer, a sulfur removal bed, or an acetylene removal bed. The treated gas is fed to the first distillation column 602 that separates the bulk of the methane from the $CO_2$ and other heavier hydrocarbons. Depending on the $CO_2$ concentration in the stream 606, the bottom stream 608 may contain at least about 50%, 60%, 70%, 80%, 90%, or more (or any value in between) of the incoming $CO_2$. The overhead from 607 contains majority of the methane and other light gases and is fed to the column 603. Column 603 further recovers methane rich gas 611, which can be the feed to a methanation system. The bottoms product 616 may be recycled or sent as a purge to the fuel gas system. The $CO_2$ rich gas 608 is distilled in the $CO_2$ column 604 to recover pure $CO_2$ 609 in the overhead. The bottoms product 610 can contain some methane along with ethane, ethylene, and other heavier hydrocarbons, and can be sent to recover the ethylene product in a separator 605. The $CO_2$ product can be sent to methanation unit, and a part of the $CO_2$ can be recycled to achieve the desired concentration of $CO_2$ in the feed stream 606. Such a $CO_2$ distillation sub system can offer many benefits, including but not limited to reducing the loop size of the OCM process considerably, as the function of the existing cryogenic demethanizer can be reduced by a large extent. Additionally, amine and caustic systems can be replaced by cryogenic or low temperature distillation systems.

Alkaline salt-based processes can be used for carbon dioxide removal. These processes can utilize the alkali salts of various weak acids, such as sodium carbonate and potassium carbonate. These processes can provide advantages such as low cost and minimal solvent degradation. Processes that can be used for $H_2S$ and $CO_2$ absorption include those using aqueous solutions of sodium or potassium compounds. For example, potassium carbonate can absorb $CO_2$ at high temperatures, an advantage over amine-based solvents.

Hot potassium carbonate ($K_2CO_3$) solutions can be used for the removal of $CO_2$ from high-pressure gas streams, among other applications. Potassium carbonate has a low rate of reaction. To improve $CO_2$ absorption, mass transfer promoters such as piperazine, diethanolamine, and arsenic trioxide can be used. Less toxic promoters such as borate can also be used, for example with flue gas streams (see, e.g., Ghosh et al., "Absorption of carbon dioxide into aqueous potassium carbonate promoted by boric acid", Energy Procedia, pages 1075-1081, February 2009, which is hereby incorporated by reference in its entirety). To limit corrosion, inhibitors can be added. These systems can be known as activated hot potassium carbonate systems. Licensed hot activated potassium carbonate systems include the Benfield and the Catacarb process. The processes can be used for bulk $CO_2$ removal from high-pressure streams, but can also produce high-purity $CO_2$.

Flue gas impurities such as SOx and NOx can reduce the operational efficiency of the potassium carbonate as a solvent. $SO_2$ and $NO_2$ may not able to be released from the solvent under industrial conditions. Selective precipitation of the impurity salts formed by SOx and NOx can be used to remove such compounds (see, e.g., Smith et al., "Recent developments in solvent absorption technologies at the CO2CRC in Australia" Energy Procedia, pages 1549-1555, February 2009, which is hereby incorporated by reference in its entirety).

A variety of materials can be used as $CO_2$ sorbents through chemical reactions and physical absorptions, including but not limited to soda-lime, active carbon, zeolites, molecular sieves, alkali metal oxides, silver oxide, lithium oxide, lithium silicate, carbonates, silica gel, alumina, amine solid sorbents, metal organic frameworks and others.

Physical impregnation of $CO_2$-reactive polymers, such as tetraethylene pentamine or polyethyleneimine, inside a porous support, such as alumina, pumice, clay or activated carbon, can be used for $CO_2$ removal. Amine based sorbents can be easily regenerated. Alternatively, a mixture of an amine compound with a polyol compound can be impregnated in a porous support. The polyol compound can be used to increase the $CO_2$ desorption rate of the amine. The supported amine-polyol sorbent can comprise at least about 1 wt %, 5 wt %, 10 wt %, 15 wt %, 20 wt %, 25 wt %, 30 wt %, 35 wt %, or more amine and/or polyol. In some cases, the supported amine-polyol sorbent can comprise from about 1 wt % to about 25 wt % amine and from about 1 wt % to about 25 wt % polyol, with the balance being the support. Solid sorbent can adsorb and desorb $CO_2$ a relatively high rates at ambient temperatures. Enhanced $CO_2$ cyclic removal capacities in either dry or humid air flows can further be achieved by using a solid sorbent at an increased amine concentration of amines from about 35 wt % to about 75 wt %.

Solid sorbents that can selectively remove multiple gases can be used to remove $CO_2$, $H_2O$, nitrogen oxides, and hydrocarbons. This can be achieved by using composite adsorbents, for example by using a mixed adsorbent of alumina and zeolite to remove $CO_2$ and $H_2O$ simultaneously.

$CO_2$ can be separated from flue gas using an ion pump method instead of relying on large temperature and pressure changes to remove $CO_2$ from a solvent. Ion pump methods can dramatically increase the overlying vapor pressure of $CO_2$. As a result, the $CO_2$ can be removed from the downstream side of the ion pump as a pure gas. The ion pumping can be obtained from techniques including but not limited to reverse osmosis, electro dialysis, thermal desalination methods, or an ion pump system having an oscillation flow in synchronization with an induced electric field.

By making use of energy such as renewable or nuclear energy, carbon dioxide and water can be recycled into sustainable hydrocarbon fuels in a non-biological process. Various pathways can enable such a conversion, for example by $H_2O$ and $CO_2$ dissociation followed by fuel synthesis. The methods of dissociation can include heat, electricity, and solar driven methods such as thermolysis, thermochemical loops, electrolysis, and photoelectrolysis. High temperature electrolysis can make efficient use of electricity and heat, provide high reaction rates, and integrate well with fuel synthesis.

Synthetic analogues of enzymes as a polymer thin film supported on micro-porous substrates can be used to separate $CO_2$ from gas mixtures. For example, a polymer thin film containing carbonic anhydrase mimicking sites can supported on a porous substrate and can separate $CO_2$ from a stream containing $O_2$ and $N_2$. The system can be, for example, about 30% lower in cost compared to amine-based systems.

$CO_2$ Anti-Sublimation

Carbon capture (e.g., $CO_2$ capture) can be used to reduce greenhouse gas (GHG) emissions. For example, carbon can be captured from stationary fired sources (e.g., flue gas emissions from fired equipment in power plants and industry). $CO_2$ capture technologies may be cost prohibitive. The cost of disposing $CO_2$ can be divided into: separation (for example, the cost range for $CO_2$ separation from flue gas using amine absorption is $30-$50 per ton of $CO_2$); compression (for example, $CO_2$ is compressed typically to 2000 psi for pipeline delivery and compression costs can range from $8-$10 per ton of $CO_2$); pipelines (for example, $CO_2$ pipelining costs can range from $0.7 to $4 per ton $CO_2$ per 100 km); and injection (for example, compressed $CO_2$ injection to geological reservoirs on land can cost from $2-$8 per ton $CO_2$.

The separation of process $CO_2$ from the OCM process can be simpler and less expensive than a $CO_2$ capture from a flue gas system. Flue gas $CO_2$ capture may have inherent challenges, which are absent from the OCM system $CO_2$: low pressure (for example, the typical flue gas pressures are at or about atmospheric pressure, and therefore involve high volumes that can need to be compressed and treated, resulting in bigger and hence more expensive equipment); high temperature (for example, flue gases can exit a furnace or heater at a high temperature); oxygen content (for example, oxygen can cause corrosion problems); NOx and fly ash content (for example, this can cause degradation in certain systems); and $CO_2$ concentration (for example, in flue gases $CO_2$ concentration can range from 10%-15%; in OCM $CO_2$ concentrations can be 95% and higher post amine system or 4-6% at OCM outlet).

To integrate well with OCM, a $CO_2$ separation process can be: less energy and capital intensive than current designs (e.g., amine system); scalable downwards and upwards; capable of reliable and continuous operation; able to take advantage of high $CO_2$ concentrations and convert to high purity $CO_2$, which can be used as a feedstock for other operations.

$CO_2$ anti-sublimation can be used to remove $CO_2$ (e.g., from flue gas). $CO_2$ anti-sublimation can use an $SO_2$ removal unit followed by a water cooling step. The water can be eventually removed, for example first as liquid then below the triple point as ice. Dry flue gas can be further cooled until $CO_2$ precipitates. The process can employ anti-sublimating $CO_2$ on a low temperature surface, thus transforming the carbon dioxide from its gaseous phase to a solid phase frosted on a cold surface. Anti-sublimation can allow $CO_2$ capture at a pressure slightly higher than atmospheric. $CO_2$ anti-sublimation can be used with a flue gas system (flue gas composition, e.g., in mol %: $CO_2$ 15%, $H_2O$ 13%, $N_2$ 70% and $O_2$ 3%) at various temperatures (e.g., about 51° C.).

The triple point of $CO_2$ is −56.4° C. and 5.11 atm. For 100% pure $CO_2$ at a pressure P' (where P' is less than 5.11 atm) the frosting temperature can be given by T'=(P'−15.6)*(22.1/4.11). Accordingly, for a pressure of 4.5 atm, T=−59.6° C.

The sublimation temperature of a substance within a gas mixture can depend on its partial pressure (its corresponding concentration within the mixture). Table 1 shows frosting temperatures at different exemplary $CO_2$ concentrations.

TABLE 1

Frosting temperature versus concentration.

| Concentration (% v/v) | 100 | 10 | 1 | 0.1 |
|---|---|---|---|---|
| Frosting temperature (° C.) | −78.5 | −103.1 | −121.9 | −136.7 |

For use in an OCM process, a $CO_2$ anti-sublimation unit may encounter higher pressure of OCM effluent (e.g., feed to $CO_2$ capture system), lower $CO_2$ concentration, and higher hydrocarbon content (e.g., methane, ethane, ethylene). Lower $CO_2$ concentration can be addressed by a recycle.

Process Configurations

Electrolysis to Generate Oxygen and Hydrogen for OCM Process

Electrolysis can be used to produce industrial hydrogen. OCM processes can have a lot of synergistic benefit from deploying a water electrolysis subsystem with the OCM process. The water electrolysis unit can replace an air separation unit (ASU) to supply the oxygen required for the OCM process. The products from the electrolytic unit can be consumed within the OCM process: oxygen can be consumed within the OCM reactor and hydrogen can be used in a methanation reactor. Availability of more hydrogen in the methanation unit has the potential to increase the carbon efficiency to about 100%, by converting the $CO_2$ produced in the OCM reaction to methane, which can be recycled back to the OCM reactor. The OCM unit can be a net exporter of high purity excess hydrogen, after consuming the entirety of the $CO_2$ produced in the OCM Process.

The water electrolysis subsystem can be an electrolytic cell employing alkaline water electrolysis, a proton exchange membrane electrolysis system, or a steam electrolysis system. The electricity source to the electrolytic sub system can be renewable, such as photo voltaic/solar power, which can make the entire system 100% carbon efficient with a zero carbon footprint. A storage system for oxygen, or a backup power supply, may be used to ensure the continuous supply of oxygen and hydrogen.

With steam electrolysis, a substantial part of the energy needed for the electrolysis process can be added as heat, which can be much cheaper than electric energy, and which the OCM reactor can produce in abundance. Therefore, integration of steam electrolysis can take advantage of the extra heat from the OCM reactor to provide energy for the steam electrolysis. This can be of particular benefit to OCM deployments where no additional steam or power is required.

Figure 7:
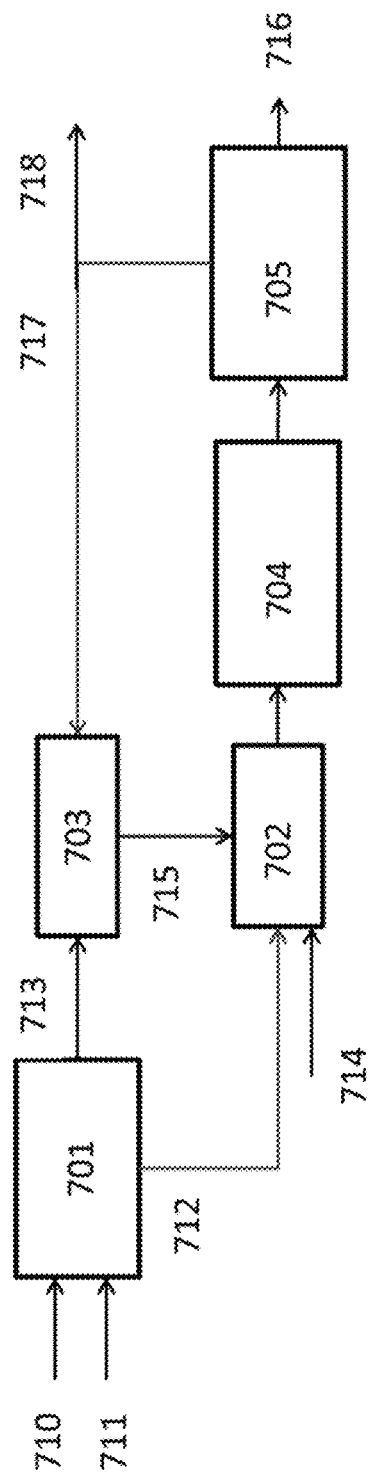
FIG. 7 shows an example water electrolysis sub system.

FIG. 7 depicts an exemplary electrolysis subsystem combined with an OCM system. The electrolysis subsystem 701 can take water 710 and electric power 711 as inputs and generate pure oxygen 712 and hydrogen 713 as products. The oxygen can be fed into an OCM reactor 702 with a methane feed 714, for conversion to higher hydrocarbon products including ethylene. The OCM product stream can be compressed in a compressor 704 and separated in a separations unit 705. Higher hydrocarbon products 716 can be recovered from the separations unit, and other compounds such as methane and $CO_2$ can be recycled 717 and/or purged 718. The recycle stream can be directed to a methanation unit 703, which can generate methane 715 using the hydrogen from the electrolysis subsystem. The extra hydrogen that is now available to the methanation unit can enable the conversion of most or all of the $CO_2$ produced in the OCM process to methane, which can drive the process to a higher efficiency. The process can also be almost 100% emission free. The $CO_2$ produced in the process that may be discarded as waste may be converted to methane and hence to ethylene in the OCM reactor.

Different Quench Media for the OCM Reaction

Figure 8:
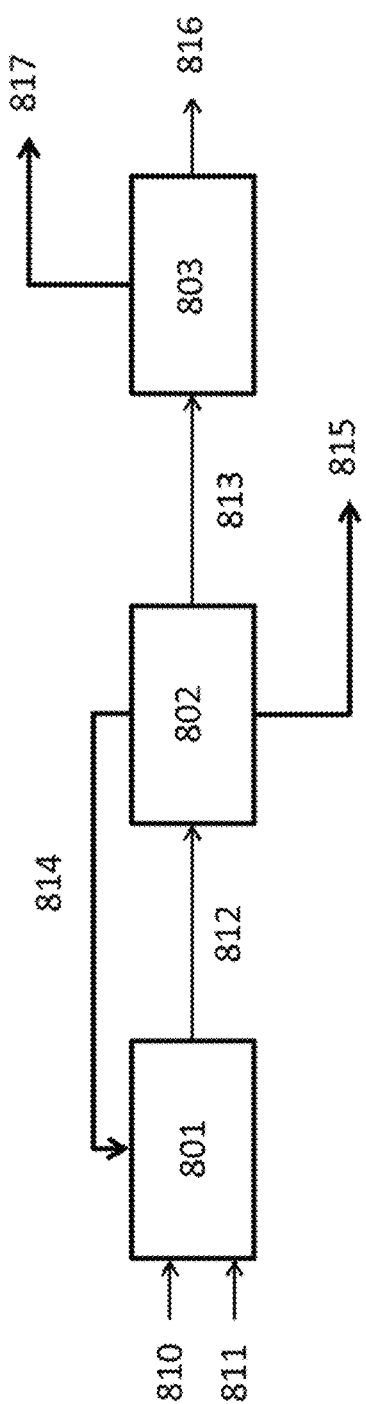
FIG. 8 shows an example OCM system with $CO_2$ as a quench medium.

The OCM reaction is highly exothermic. Various quenching media can be used to extract the OCM reaction heat. For example, $CO_2$ can be injected to extract the heat, which results in the OCM effluent containing excess $CO_2$, such effluent can be suitable for the advanced $CO_2$ recovery methods described herein. FIG. 8 shows an exemplary system where $CO_2$ 814 is removed from an OCM product stream 812 (generated in an OCM unit 801 from an oxygen stream 810 and a methane stream 811) in a $CO_2$ separation unit 802 and recycled from back to the OCM reactor 801. A waste gas or purge stream 815 can also be removed from the $CO_2$ separation unit. The OCM product stream 813 can then be separated in a separations unit 803 into a product stream 816 comprising ethylene and a purge and/or recycle stream 817. Separation methods can include low temperature separation, membrane separation, or other separation methods discussed herein. The OCM loop can be decreased to just a $CO_2$ recycle stream. The system can also comprise a methanation unit (not shown).

Such an approach can provide advantages including a smaller recycle loop and more efficient $CO_2$ removal methods, resulting in lower capital expenditure (CAPEX). This can also result in the feasibility of small distributed scale OCM units, since after the removal of excess $CO_2$, the relatively richer ethylene stream needs fewer treatment and recovery steps.

Heat Recovery

Waste heat from the OCM process can be used to generate superheated high pressure steam that can be used in the process, exported to other users on site, or can be used to generate power. Excess process heat can also be used to preheat the feed streams. Other uses for excess heat can be less capital intensive, and offer a greater operational flexibility and low maintenance. Thermoelectric energy conversion can be used to convert waste heat to power. Example uses for waste heat include single fluid rankine cycles (e.g., steam cycle, hydrocarbons, and ammonia), binary/mixed fluid cycles (e.g., ammonia/water or mixed hydrocarbon cycle).

Organic Rankine Cycle

The organic Rankine cycle (ORC) can be used to generate power from heat. In ORC, an organic component is used instead of water. The organic compound can be a refrigerant, a hydrocarbon (e.g., butane, pentane, hexane), silicon oil, or a perfluorocarbon. The boiling point of the organic fluid can be lower than that of water, which can allow recovering heat at a lower temperature than in the traditional steam Rankine cycle.

Owing to the exothermicity of the OCM reaction, the ORC system can be deployed as a waste heat recovery method for use with OCM. Waste heat at relatively low temperature can be recovered by an intermediate heat transfer loop and used to evaporate the working fluid of the ORC.

Figure 9:
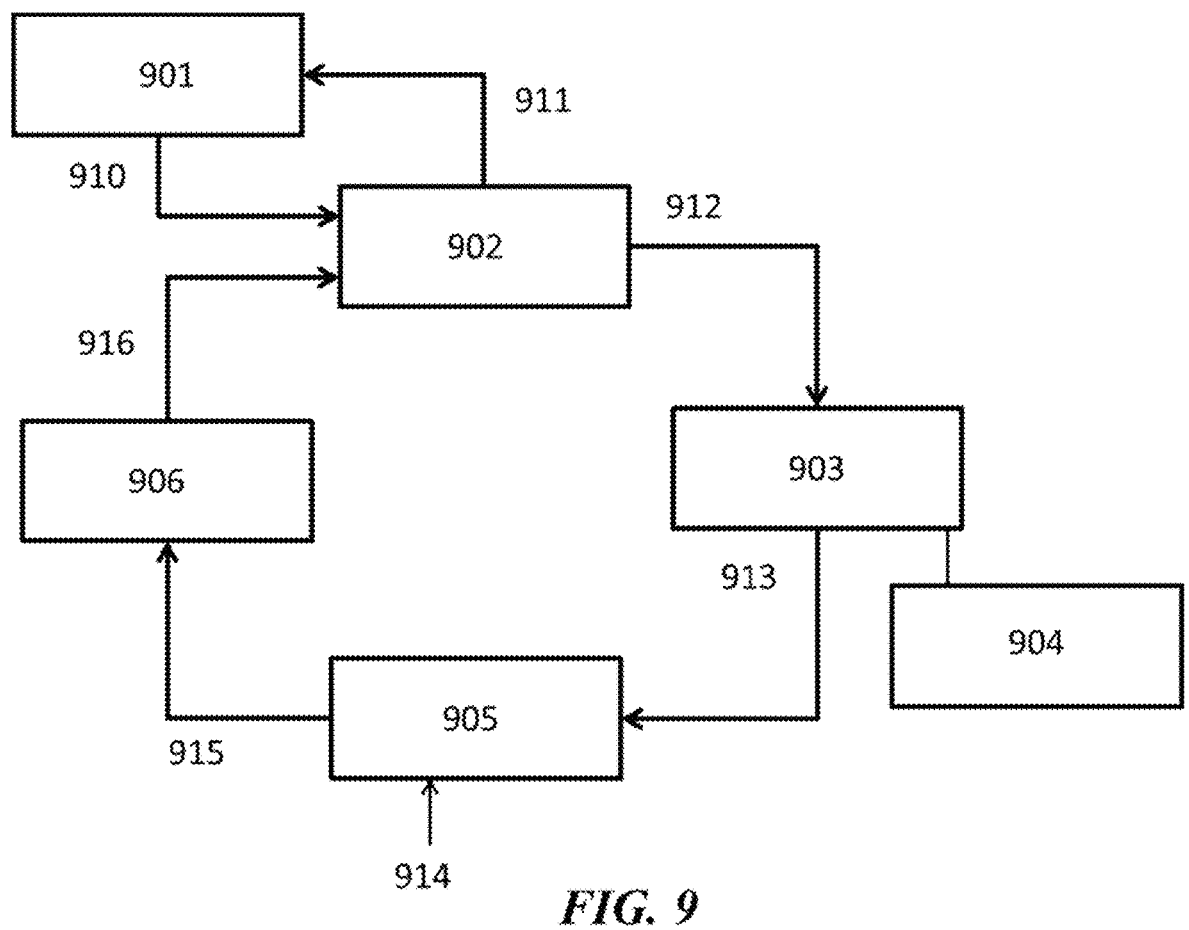
FIG. 9 shows an example organic Rankine cycle (ORC) subsystem.

FIG. 9 shows an exemplary OCM system with an ORC subsystem. The working fluid can be chosen which can be condensed with cooling water or air at normal atmospheric pressure. FIG. 9 shows the heat source as the OCM reaction heat from an OCM unit 901. Heat can be recovered from the OCM product stream 910 in an evaporator 902, and the product stream 911 can then be directed for downstream processing from the OCM unit. The heat recovered in the evaporator can be used to evaporate a working fluid stream 912, which can then be directed to a turbine 903 to generate power in a generator 904. From the turbine, the working fluid 913 can be directed to a condenser 905 and cooled using a cooling medium 914. The cooled working fluid 915 can then be pumped by a pump 906 in a stream 916 back to the evaporator.

Thermoelectric Power Generation

The OCM process can make use of a heat exchanger with thermoelectric (TE) generators for heat recovery. A Thermoelectric Power Generator (TPG) can have four basic components: Heat source, P and N type semiconductor stack (or a TE module), heat sink (cold side), and an electrical load (output voltage). The TE module can include two or more of P-type and N-type semiconductor pellets connected in series or parallel depending on the served load.

The TE devices can be solid state engines that do not require any working fluid. Thermoelectric materials can provide efficiencies of up to 15% or greater. Thermoelectric generators coupled with heat exchangers can produce electricity even at temperatures as low as 350 K with low maintenance. TE modules can be used with OCM including large bulk TE modules and thin film or micro TE modules.

For high temperatures, micro TE modules can be used. Micro TE modules can also have low equipment weights. TE devices can be very reliable, scalable, and modular. Some TE modules can give best results at small scales. The OCM process can generate medium level waste heat that is highly suitable for a TE device to generate power.

OCM and ETL Systems with Advanced Separations Sub-Systems

PSA technology can be applied to processes including those involving a hydrocarbon stream containing a mix of the following hydrogen, carbon dioxide, carbon monoxide, methane, ethane, ethylene, propane, propylene, butanes, butenes and/or other higher hydrocarbons needing to be purified or separated into desirable products (e.g., ethylene, methane, hydrogen, or propylene).

Hydrocarbon streams can be produced via traditional refining and petrochemical processes. Hydrocarbon streams can be produced from OCM or ETL reactor systems.

The present disclosure provides the use of PSA in processes and systems for oxidative coupling of methane (OCM) and ethylene-to-liquids (ETL) operations, and the application of adsorbent based processes used in conjunction with OCM and ETL processes to generate significant process improvements and enhance the economic value of the processes. OCM systems are described in, for example, U.S. Patent Publication No. US 2015/0210610, which is entirely incorporated herein by reference. ETL systems are described in, for example, U.S. Patent Publication No. 2015/0232395, which is entirely incorporated herein by reference.

Figure 10:
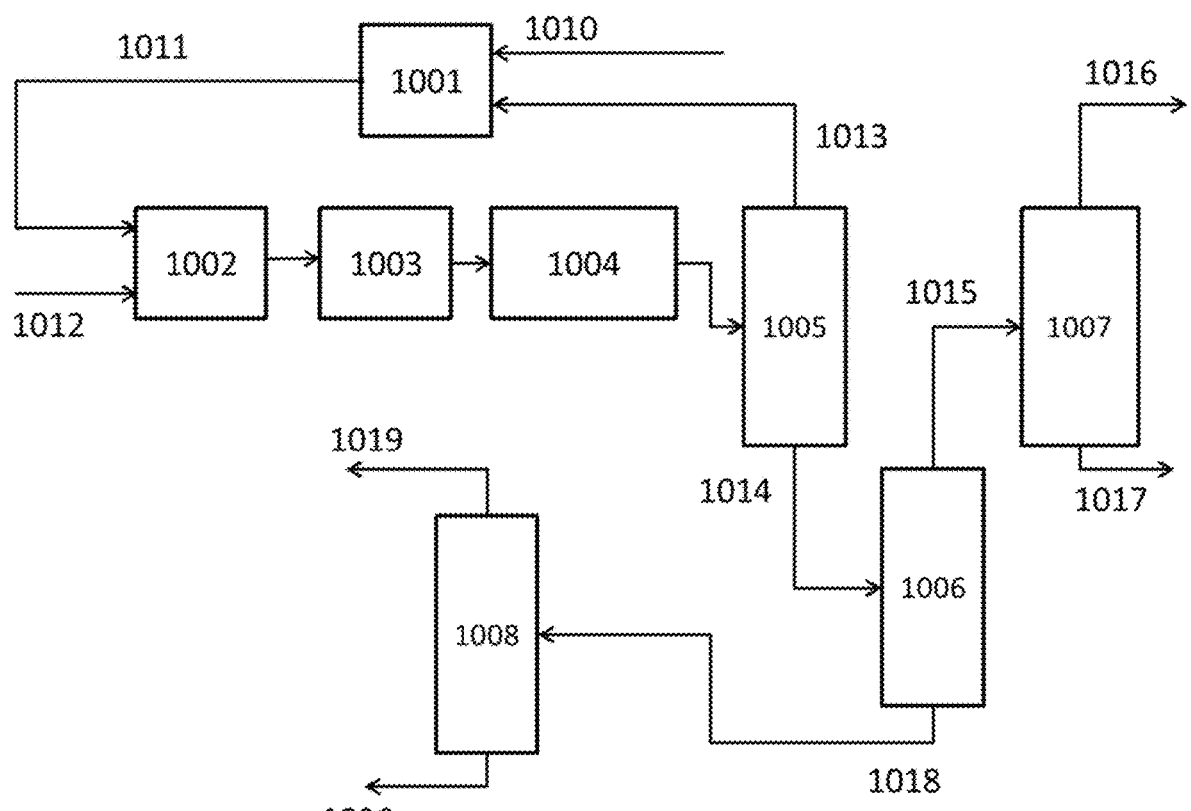
FIG. 10 shows an exemplary typical OCM system.

An OCM system, such as that shown in FIG. 10, can include an OCM or OCM-post-bed-cracking (PBC) reactor 1002, a process gas compression system 1003, a process gas treatment system 1004, a cryogenic separations system, and a methanation system 1001. The feed to the OCM system can be an oxygen feed 1012 and a methane source feed 1011 (such as a natural gas feed stream or other methane source). In some cases, additional ethane feed can be supplied to the PBC section of the OCM reactor, where paraffins such as ethane in the OCM product stream and/or additional ethane can be cracked to olefins such as ethylene. The separations sub-system can comprise a series of fractionation towers, like a demethanizer 1005, deethanizer 1006, $C_2$ splitter 1007, depropanizer 1008, debutanizer, and others. Overhead 1013 from the demethanizer can be directed into the methanation system along with hydrogen or natural gas 1010 to produce additional methane. The bottoms stream 1014 from the demethanizer can be directed to the deethanizer. The overhead stream 1015 from the deethanizer can be directed to the $C_2$ splitter, and there split into ethylene 1016 and ethane 1017 streams. The bottoms stream 1018 from the deethanizer can be directed to the depropanizer, and there split into a $C_3$ product stream 1019 and a $C_{4+}$ product stream 1020. The cryogenic separations system can comprise additional ethylene and propylene refrigeration sub-systems to provide for the chilling requirements of the system.

OCM Process Standalone with Advanced Separations Systems

Figure 11:
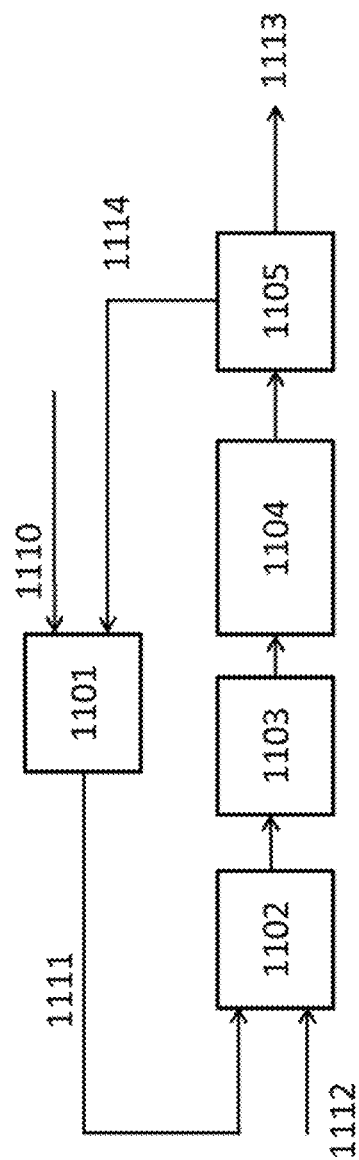
FIG. 11 shows an exemplary OCM system with a single stage PSA unit.

In certain cases, the separations section of the OCM system can be eliminated, or partially eliminated, by utilizing an advanced separations method as discussed in this application. The advanced separation method can be a PSA unit or a membrane based method, or a cryogenic system. FIG. 11 shows an exemplary schematic of OCM with a PSA unit. The PSA unit can separate methane, $CO_2$, CO, and/or $H_2$ from ethane, ethylene, propane, propylene, and/or higher hydrocarbons. Methane 1111 and oxygen 1112 can be directed into an OCM reactor 1102 and reacted to produce higher hydrocarbon products including ethylene. The OCM product can be compressed in a process gas compression system 1103, treated in a process gas treatment system 1104, and separated in the PSA 1105 into a product stream 1113 and a recycle stream 1114. The recycle stream can be directed to a methanation unit 1101, which can also receive a natural gas stream 1110 and produce methane for the OCM reactor. The extent of separation and degree of recovery can depend on the type of adsorbent(s), pressure differential, and number of PSA stages employed. The feed to the PSA unit can have one or more of the following components: $H_2$, $N_2$, $O_2$, CO, $CO_2$, $CH_4$, ethane, ethylene, acetylene, propane, propylene, butanes, butenes, butadiene, water, and higher paraffinic and olefinic components. The PSA product gas can comprise components including but not limited to: $H_2$, $N_2$, CO, $CO_2$, $CH_4$, $O_2$, ethane, ethylene and acetylene. PSA product gas can comprise components from about 0% to about 99.99% recovery. The PSA tail gas can comprise less than or equal to about 99.99%, 90%, 80%, 70%, 60%, 50% or less ethylene. The PSA tail gas can comprise at least or equal to about 50%, 60%, 70%, 80%, 90%, 99.99% or more ethylene. The PSA tail gas can comprise about less than or equal to about 99%, 90%, 80%, 70%, 60%, 50%, 40%, 30%, 20%, 10%, 1% or less ethane. The PSA tail gas can comprise at least about 0.1%, 1%, 10%, 20%, 30%, 40%, 50%, 60%, 70%, 80%, 90%, 99% or more ethane. The PSA tail gas can comprise about less than or equal to about 60%, 50%, 40%, 30%, 20%, 10%, 1% or less methane, hydrogen, acetylene, $N_2$, $O_2$, $H_2O$ and/or $CO_2$. The PSA tail gas can comprise at least about 0.1%, 1%, 10%, 20%, 30%, 40%, 50%, 60% methane, hydrogen, acetylene, $N_2$, $O_2$, $H_2O$ and/or $CO_2$. Based on the process configuration, including the type of adsorbents employed, pressure differential and the operation, various different recoveries are possible.

As discussed above, the PSA unit can comprise one or more adsorbent materials that can be suitable to achieve the component recoveries. The sorbent can be a zeolite/molecular sieve based material, a carbon based sorbent, or a it-complexation sorbent. In some cases the sorbent material can be a polymeric resin, carbon nanotubes, and carbon fibers. The PSA unit can be configured to have layers of different sorbents so as to result in high recoveries from the multi-component feed streams to the desired products.

Figure 12:
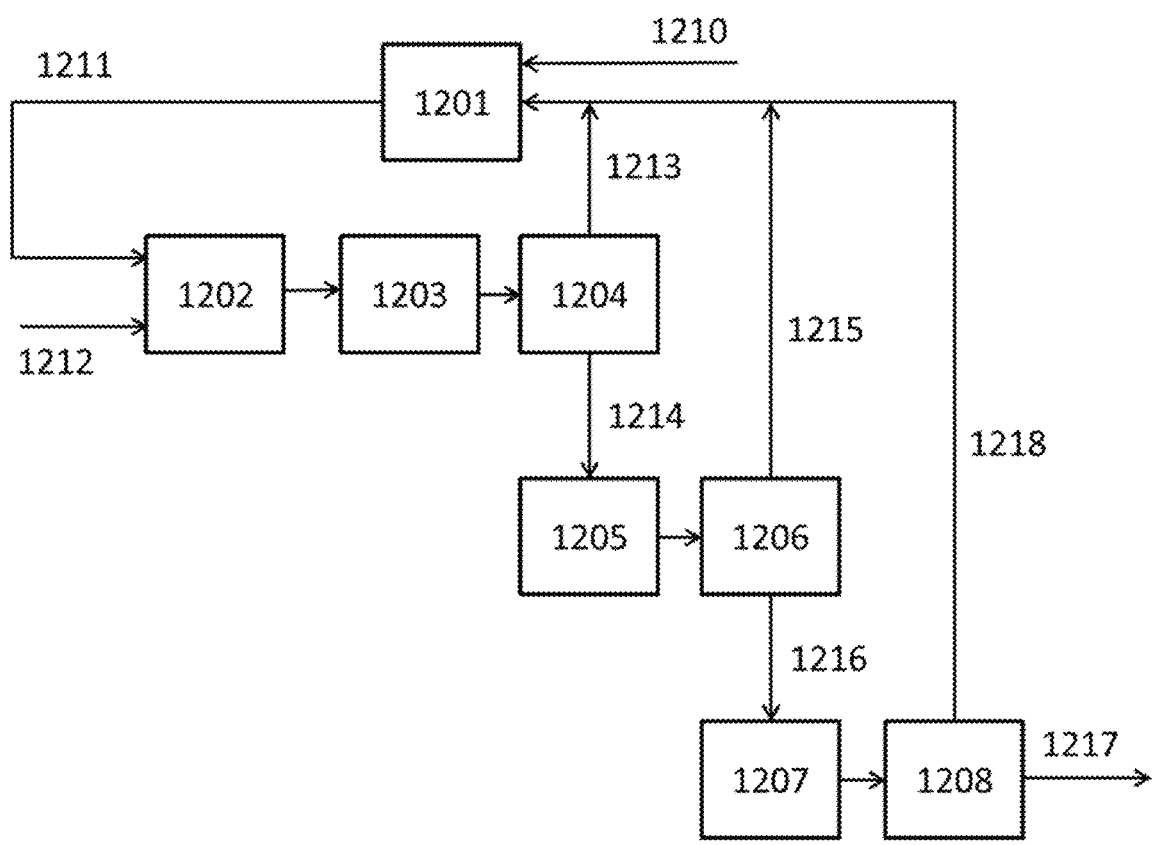
FIG. 12 shows an exemplary OCM system with a multi stage PSA unit.

In certain cases the PSA can be a multi stage unit (see, e.g., FIG. 12). In such a unit, an OCM reactor 1202 can receive a methane stream 1211 and an oxygen stream 1212, and react the methane and oxygen to produce higher hydrocarbon products including ethylene in an OCM product stream. The OCM product stream can be compressed in a first compressor 1203 and directed to a first PSA separation 1204. The tail gas 1214 from the first PSA can be compressed in a second compressor 1205 and fed to a second PSA separation 1206, the tail gas 1216 from which can be compressed in a third compressor 1207 and separated in a third PSA separation 1208. The tail gas from the third PSA can be the final purified stream 1217 containing ethylene up to 99.9% purity. PSA product streams 1213, 1215, and 1218 can be directed to recycle, such as via a methanation unit 1201 along with a natural gas stream 1210. Each PSA stage can be a dual-bed PSA or a multi-bed PSA system.

In certain cases, the process requirements can dictate that only a limited amount of recovery is required in the PSA unit and subsequent recovery and purification is performed in a fractionation column or the gas is a feed for a downstream process unit. The downstream process unit can be an ETL system, an ethylene steam cracker system, a gas processing plant, NGL extraction plant, a refinery off-gas separations system, or other process unit.

Retrofits for OCM

OCM can be employed to convert a feedstock comprising methane to ethylene and other olefins. Historically, ethylene has been produced via steam cracking of gaseous or liquid hydrocarbon feedstocks like ethane, propane, LPG, or naphtha. As in most of the refining and petrochemical operations, a steam cracking operation can involve a cryogenic fractionation or a separations section that consists of a series of fractionation columns to successively recover various components at high product purity.

The present disclosure includes the application of PSA processes to an OCM retrofit of an existing ethylene cracker (e.g., steam cracker).

Figure 13:
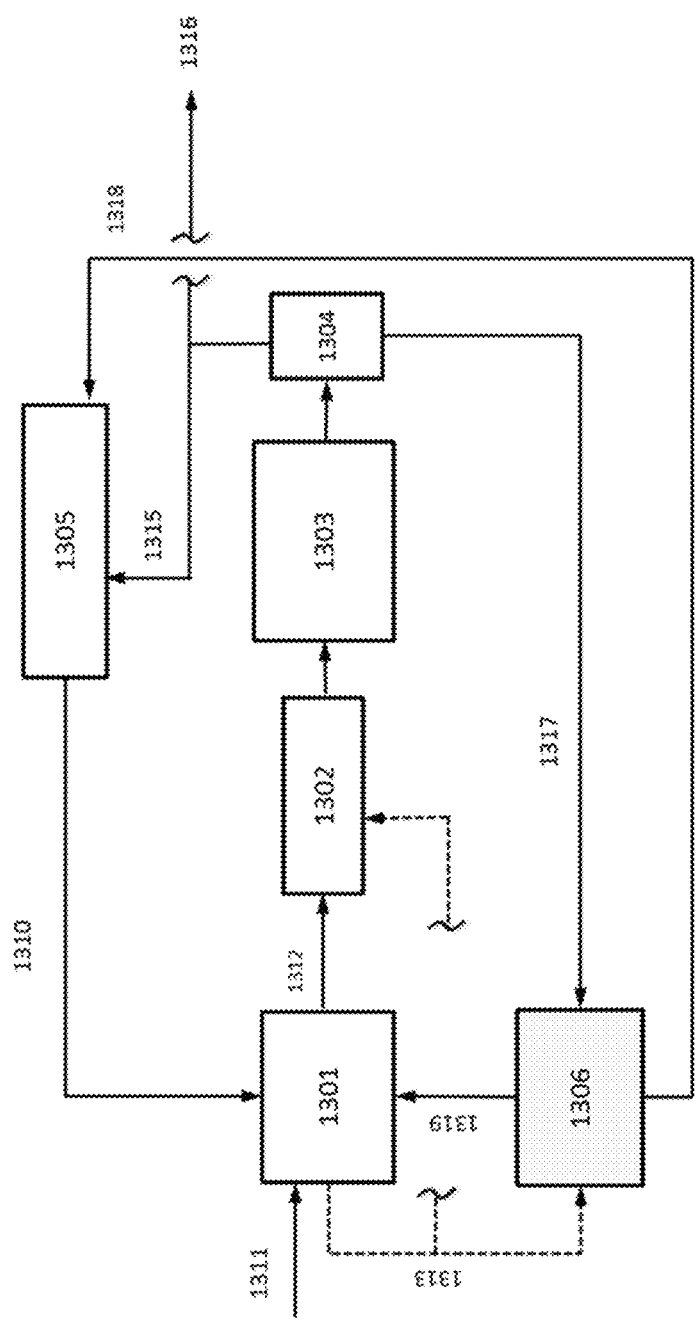
FIG. 13 shows an exemplary retrofit of OCM to a cracker, with a single stage PSA unit.

An example application for OCM combined with a PSA unit involves an existing petrochemical plant such as a steam cracker is considering low cost ways to add ethylene capacity. A typical revamp to add capacity may include addition of, or debottlenecking of, the existing fractionation towers for the entire flow addition for the revamp. However, as shown in FIG. 13, the use of a PSA unit as disclosed herein can provide a low cost alternative to traditional revamps. An OCM unit with a PSA unit retrofitted to an existing steam cracker can be an effective way of adding ethylene capacity at a low marginal cost. The advantages of adding a PSA unit include that no additional cryogenic separation is required for the added capacity. For ethylene revamps, one of the key areas during debottlenecking may be the refrigeration systems and/or the fractionation columns, but utilizing the PSA to separate or pre-separate the additional product stream can result in a simpler and easier debottlenecking. As in shown in FIG. 13, for example, the tail gas from the PSA can be sent to the cracker system where the ethylene is recovered.

FIG. 13 shows an example of an OCM process integrated with an existing ethylene cracker using a PSA system for separations. The OCM reactor 1301 takes in methane 1310 and oxygen 1311 and produces an OCM effluent 1312 having $CO_2$, $CH_4$ and $C_2H_4$, in some cases amongst other components, such as $H_2$ and CO. The OCM reaction can be exothermic and can produce steam 1313. The OCM effluent can be compressed in a compressor 1302 and optionally treated in an acid gas removal system 1303, and fed into a pressure swing adsorption (PSA) unit 1304. In some cases the acid gas removal system may have an additional knock out drum to condense and separate any condensates and water. It also can include a drier to remove water. The PSA unit can produce a product stream that can include $H_2$, $CH_4$, ethane, $CO_2$ and CO. The overhead stream 1315 can be fed into a methanation subsystem 1305 (e.g., methanation reactor) to provide methane for the OCM reactor, and some of the overhead stream can be purged 1316 to a fuel gas system, for example. Additional methane can be provided by way of a natural gas stream or other methane stream. The PSA tail gas 1317 can comprise most of the ethylene, the content of which may range from about 50% to about 99.9% depending on the process configuration and operation of the PSA system. The PSA tail gas can also comprise $H_2$, CO, $CO_2$, $CH_4$, ethane, propane, propylene, butanes, butenes, and other components. The process of FIG. 13 can further include an existing ethylene cracker 1306. The PSA tail gas can be fractionated using existing separations capacity in the ethylene cracker. The heavy components can be processed in the fractionation towers of the ethylene cracker, optionally first being compressed in the existing process gas compressor of the ethylene cracker. In some cases, the heavy components stream can be routed to the $CO_2$ removal unit of the existing ethylene cracker subsystem to meet the $CO_2$ specification. The OCM reactor can receive a $C_2$ recycle stream 1319 from the cracker complex.

The combination of a new OCM unit and an existing ethylene cracker can provide synergistic benefits. It can provide for a low cost alternative to add ethylene capacity to the existing cracker. In some cases, prior to retrofit of an ethylene cracker with OCM, the entire overhead from the existing demethanizer is used as fuel gas, and can now be available as one of the feeds to the methanation unit. In some cases, the demethanizer overhead off-gas comprises up to 95% methane, which can be converted to ethylene in the OCM reactor, hence increasing the total ethylene capacity. In some cases, the hydrogen content in the existing demethanizer overhead is substantial, and may be enough to meet the hydrogen requirement of the methanation unit.

In some cases, retrofitting an ethylene cracker with OCM reduces (or allows for reduction of) the severity of cracking in the existing cracker, enabling value addition by increasing the production of pyrolysis gasoline components in the cracker effluent, as the OCM reactor produces the ethylene that may be needed to achieve the total system capacity. The cracker can then be operated on high propylene mode to produce more propylene and at the same time meeting the ethylene production rate by the new OCM unit. This retrofit can result in greater flexibility for the ethylene producer with respect to the existing cracker operation.

In some instances, the overall carbon efficiency can be increased as the methane and hydrogen from the existing demethanizer off-gases can be utilized to convert the carbon dioxide and carbon monoxide to methane, which is fed to the OCM reactor.

In some instances, ethane and/or propane recycle streams from the existing cracker can be routed to the OCM unit (e.g., instead of the cracking furnaces). These recycle streams are typically routed to the cracking furnaces where they are cracked to extinction. This can provide an advantage over routing the recycle streams to OCM over the cracking furnace, such as higher selectivity to ethylene in the OCM process.

Figure 14:
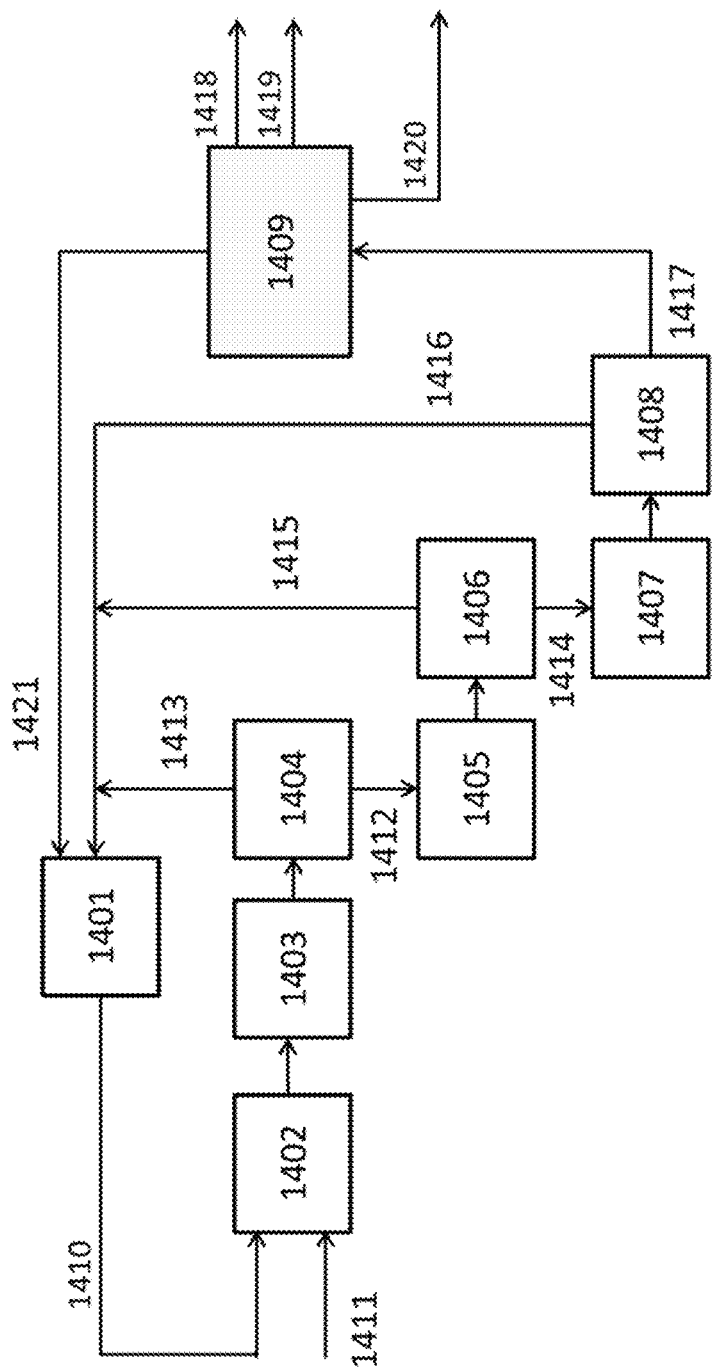
FIG. 14 shows an exemplary retrofit of OCM to a cracker, with a multi stage PSA unit.

In certain cases, more than one stages or PSA columns may be employed to achieve higher recovery and higher product purity. As in shown FIG. 14, for example, up to 99.9% recovery is possible using the multi stage PSA units. An OCM reactor 1402 can receive a methane stream 1410 and an oxygen stream 1411, and react the methane and oxygen to produce higher hydrocarbon products including ethylene in an OCM product stream. The OCM product stream can be compressed in a first compressor 1403 and directed to a first PSA separation 1404. The tail gas 1412 from the first PSA can be compressed in a second compressor 1405 and fed to a second PSA separation 1406, the tail gas 1414 from which can be compressed in a third compressor 1407 and separated in a third PSA separation 1408. The tail gas from the third PSA can be the final purified stream 1417 can be directed to a cracker unit 1409, such as an existing cracker unit, where it can be processed and separated into an ethylene product stream 1418, a propylene product stream 1419, and an additional product stream 1420. PSA product streams 1413, 1415, and 1416 can be directed to recycle, such as via a methanation unit 1401, along with a demethanizer off gas stream 1421 from the cracker unit. Each PSA stage can be a dual-bed PSA or a multi-bed PSA system.

The application of a PSA unit to OCM systems, standalone or retrofits to existing facilities exhibits immense potential in terms of cost savings and ease of integration and retrofit to existing facilities.

ETL Systems

Figure 15:
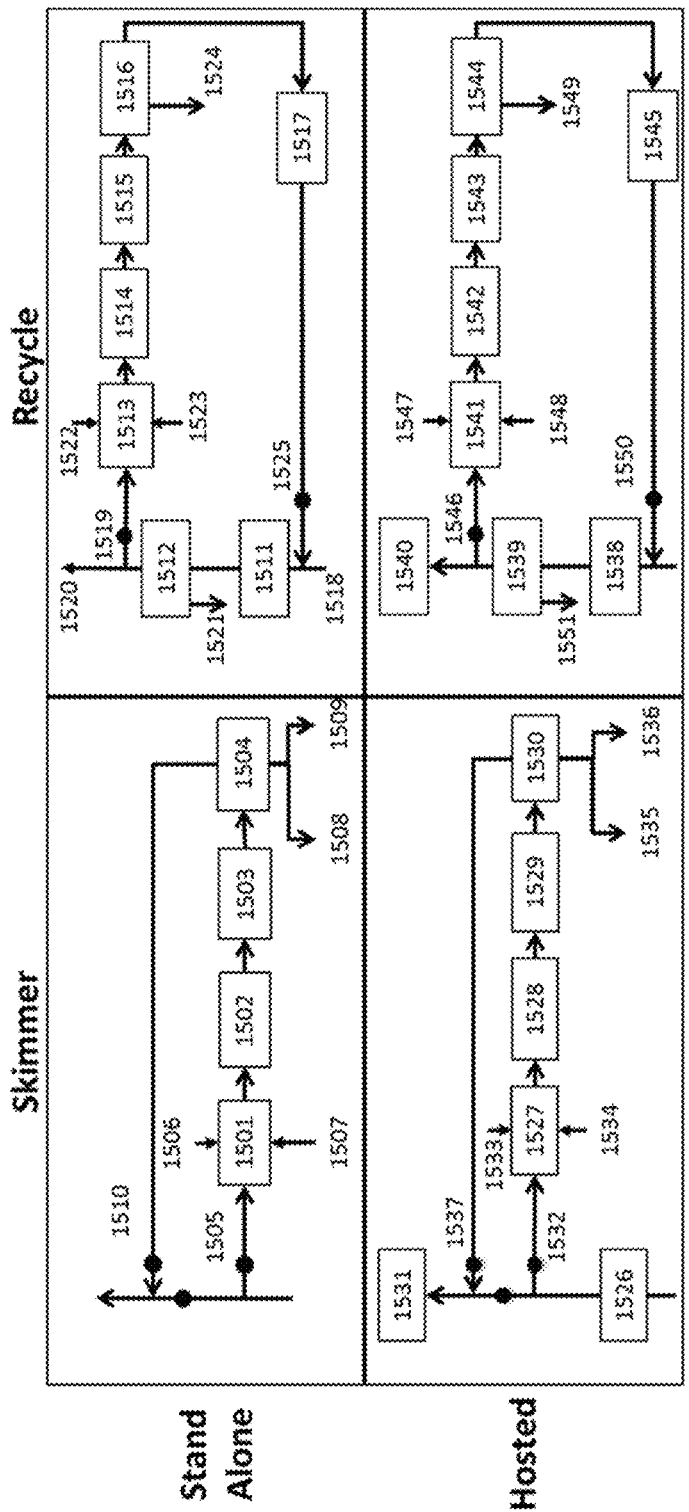
FIG. 15 shows exemplary configurations of ethylene to liquids (ETL) systems without PSA.

FIG. 15 shows various exemplary configurations for an OCM-ETL process. In the upper left, FIG. 15 shows a standalone skimmer configuration, where a methane stream 1505 can be directed into an OCM reactor 1501 with an oxygen feed 1506 and optionally an ethane feed 1507. The OCM reactor product stream can be directed into a compressor 1502 and then into an ETL reactor 1503. The ETL product stream can be directed into a gas separations unit 1504, where it can be separated into a $C_{2+}$ product stream 1508, a $C_{5+}$ product stream 1509, and an overhead stream 1510 comprising methane which can be returned to a pipeline, sold to a consumer, or otherwise used. In the upper right, FIG. 15 shows a standalone recycle configuration, where a methane feed stream 1518 (e.g., from a natural gas pipeline) is directed into a treatment unit 1511 and then into a separations system (e.g., cryogenic) 1512. A methane feed stream 1519 can be directed to an OCM reactor 1513, while another methane stream 1520 can be purged or used for power generation. A $C_{2+}$ stream 1521 can also be recovered from the separations system. An oxygen feed stream 1522 and optionally an ethane stream 1523 can also be directed into the OCM reactor, and the reactor can produce an OCM product stream. The OCM product stream can be directed into a compressor 1514 and then into an ETL reactor 1515. The ETL product stream can be processed in a knockout drum 1516 or other separator to remove a $C_{5+}$ product stream 1524. The remaining ETL product stream can be directed to a compressor 1517 and recycled 1525 to the treatment unit. In the lower left, FIG. 15 shows a hosted skimmer configuration, where a methane stream 1532 can be directed from a separations system 1526 (e.g., cryogenic) into an OCM reactor 1527 with an oxygen feed 1533 and optionally an ethane feed 1534. The OCM reactor product stream can be directed into a compressor 1528 and then into an ETL reactor 1529. The ETL product stream can be directed into a gas separations unit 1530, where it can be separated into a $C_{2+}$ product stream 1535, a $C_{5+}$ product stream 1536, and an overhead stream 1537 comprising methane which can be returned to a recompressor 1531. In the lower right, FIG. 15 shows a hosted recycle configuration, where a methane stream is directed into a treatment unit 1538 and then into a separations system (e.g., cryogenic) 1539. A methane feed stream 1546 can be directed to an OCM reactor 1541, while another methane stream can be directed to a recompressor 1540. A $C_{2+}$ stream 1551 can also be recovered from the separations system. An oxygen feed stream 1547 and optionally an ethane stream 1548 can also be directed into the OCM reactor, and the reactor can produce an OCM product stream. The OCM product stream can be directed into a compressor 1542 and then into an ETL reactor 1543. The ETL product stream can be processed in a knockout drum 1544 or other separator to remove a $C_{5+}$ product stream 1549. The remaining ETL product stream can be directed to a compressor 1545 and recycled 1550 to the treatment unit.

Figure 16:
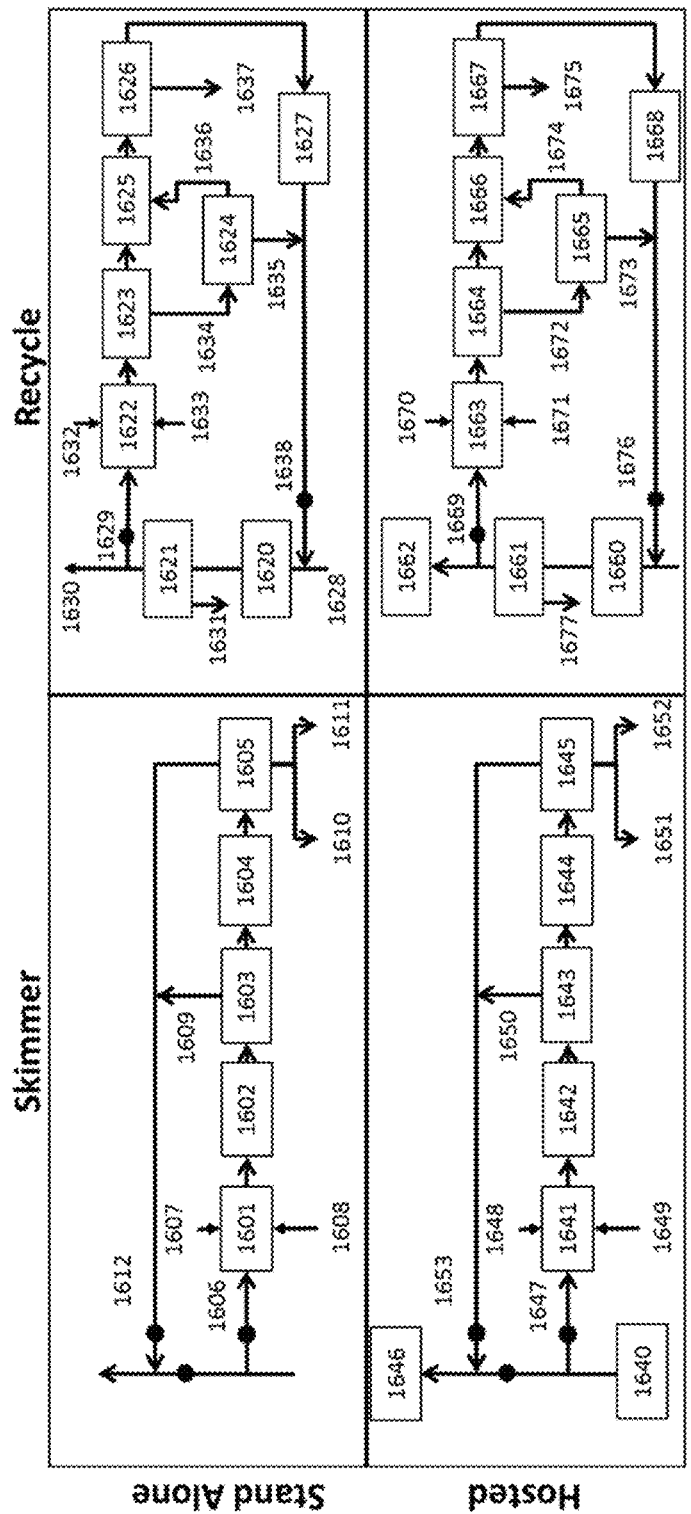
FIG. 16 shows exemplary configurations of ETL systems with PSA.

FIG. 16 shows similar configurations as FIG. 15, with an added pressure swing adsorption (PSA) unit to pre-separate the OCM effluent to remove most of the methane, hydrogen, CO and $CO_2$ from the olefinic stream, which is then fed to the ETL reactor. This can result in a feed to the ETL reactor that is concentrated in olefins. Though the process remains similar, the entire ETL and separations train becomes considerably smaller; that is, larger capacities can be achieved in the same set-up or same footprint. In some cases this can improve the ETL reaction operation. In the upper left, FIG. 16 shows a standalone skimmer configuration, where a methane stream 1606 can be directed into an OCM reactor 1601 with an oxygen feed 1607 and optionally an ethane feed 1608. The OCM reactor product stream can be directed into a compressor 1602 and then into a PSA unit 1603. A light stream 1609 comprising methane, hydrogen, CO and $CO_2$ can be directed from the PSA back to a pipeline, sold to a consumer, or otherwise used. An olefinic stream can be directed from the PSA to an ETL reactor 1604. The ETL product stream can be directed into a gas separations unit 1605, where it can be separated into a $C_{2+}$ product stream 1610, a $C_{5+}$ product stream 1611, and an overhead stream 1612 comprising methane which can be returned to a pipeline, sold to a consumer, or otherwise used. In the upper right, FIG. 16 shows a standalone recycle configuration, where a methane feed stream 1628 (e.g., from a natural gas pipeline) is directed into a treatment unit 1620 and then into a separations system (e.g., cryogenic) 1621. A methane feed stream 1629 can be directed to an OCM reactor 1622, while another methane stream 1630 can be purged or used for power generation. A $C_{2+}$ stream 1631 can also be recovered from the separations system. An oxygen feed stream 1632 and optionally an ethane stream 1633 can also be directed into the OCM reactor, and the reactor can produce an OCM product stream. The OCM product stream can be directed into a compressor 1623, and at least a portion 1634 of the OCM product stream can be directed from the compressor into a PSA unit 1624. A light stream 1635 comprising methane, hydrogen, CO and $CO_2$ can be directed from the PSA back to the treatment unit. An olefinic stream 1636 can be directed from the PSA to an ETL reactor 1625. The ETL product stream can be processed in a knockout drum 1626 or other separator to remove a $C_{5+}$ product stream 1637. The remaining ETL product stream can be directed to a compressor 1627 and recycled 1638 to the treatment unit. In the lower left, FIG. 16 shows a hosted skimmer configuration, where a methane stream 1647 can be directed from a separations system 1640 (e.g., cryogenic) into an OCM reactor 1641 with an oxygen feed 1648 and optionally an ethane feed 1649. The OCM reactor product stream can be directed into a compressor 1642 and then into and then into a PSA unit 1643. A light stream 1650 comprising methane, hydrogen, CO and $CO_2$ can be directed from the PSA to a recompressor 1646. An olefinic stream can be directed from the PSA to an ETL reactor 1644. The ETL product stream can be directed into a gas separations unit 1645, where it can be separated into a $C_{2+}$ product stream 1651, a $C_{5+}$ product stream 1652, and an overhead stream 1653 comprising methane which can be returned to the recompressor. In the lower right, FIG. 16 shows a hosted recycle configuration, where a methane stream is directed into a treatment unit 1660 and then into a separations system (e.g., cryogenic) 1661. A methane feed stream 1669 can be directed to an OCM reactor 1663, while another methane stream can be directed to a recompressor 1662. A $C_{2+}$ stream 1677 can also be recovered from the separations system. An oxygen feed stream 1670 and optionally an ethane stream 1671 can also be directed into the OCM reactor, and the reactor can produce an OCM product stream. The OCM product stream can be directed into a compressor 1664 and at least a portion 1672 of the OCM product stream can be directed from the compressor into a PSA unit 1665. A light stream 1673 comprising methane, hydrogen, CO and $CO_2$ can be directed from the PSA back to the treatment unit. An olefinic stream 1674 can be directed from the PSA to an ETL reactor 1666. The ETL product stream can be processed in a knockout drum 1667 or other separator to remove a $C_{5+}$ product stream 1675. The remaining ETL product stream can be directed to a compressor 1668 and recycled 1676 to the treatment unit.

The ETL reactor can be a tubular, packed bed, moving bed, fluidized bed, or other reactor type. An ETL reactor can be an isothermal or adiabatic reactor. The ETL system can benefit from a feed concentrated in olefins. The ETL reactor system can use a recycle stream to control and moderate the temperature increase in the reactor bed due to the highly exothermic nature of the ETL reactions. ETL systems are described in, for example, U.S. Patent Publication No. 2015/0232395, which is entirely incorporated herein by reference.

In some cases, one or more of the fractionation towers can be deemed redundant if using the PSA, as an example, a demethanizer may not be required and the sales gas or purge gas to fuel can be sent from the PSA itself.

Retrofit Applications for Midstream and Refining

Figure 17:
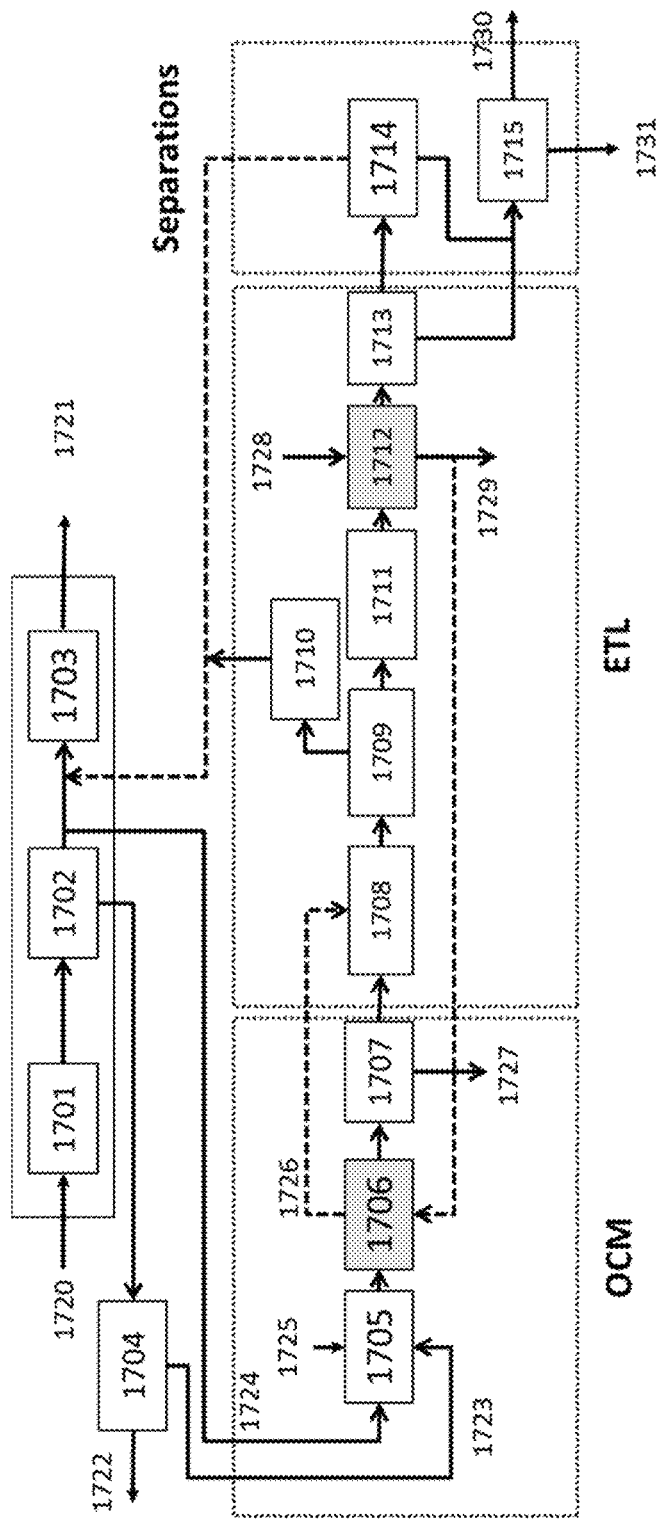
FIG. 17 shows an exemplary PSA unit integrated with an OCM-ETL system for a midstream application.

Systems, such as those of FIG. 17, can be integrated with an existing gas processing plant where one or more of the existing subsystems can be utilized. The utilization may arise from the fact that the existing subsystems are no longer used, or have an additional capacity available to allow for the integration.

FIG. 17 shows an exemplary application of an OCM-ETL system using a PSA system for pre-separations to an existing gas processing plant, where one or more existing sub systems may be utilized. As shown in FIG. 17, the existing separations sub-system can be integrated with the OCM-ETL system to add value by converting natural gas to higher value liquid hydrocarbons. The PSA unit can be used to pre-separate the lighter components like methane, hydrogen, carbon monoxide, carbon dioxide, ethane, and other components, and the olefin rich stream can be sent to the ETL reactor that converts the olefins to higher molecular weight liquid hydrocarbons. One advantage of using a PSA system is the reduction in net additional feed to the existing separation system, which can be de-bottlenecked easily. If the separation system is no longer in use, addition of a PSA can bring about larger total capacities that can be achieved by adding larger OCM-ETL systems. A natural gas stream 1720 can be directed to a treatment unit 1701 and then into a separations system (e.g., cryogenic) 1702. At least portion of a methane stream 1724 from the separations unit can be directed to an OCM reactor 1705, while a portion of the methane stream can be directed to a compressor 1703 and used as sales gas 1721 or other purposes. A higher hydrocarbon stream can be directed from the separations system to a $C_2$ removal unit 1704, which can produce a natural gas liquids stream 1722 and a $C_2$ stream 1723. The $C_2$ stream can be fed into the OCM reactor with the methane stream and an oxygen stream 1725, and reacted to form higher hydrocarbon products including ethylene. The OCM product stream can be directed into a heat recovery system 1706, which can generate a high pressure superheated (HPSH) steam stream 1726. The OCM product stream can then be directed to a knockout drum 1707 to recover a condensate stream 1727. The OCM product stream can then be directed to a compressor 1708, which can operate using the HPSH steam stream. From the compressor, the OCM product stream can be directed to a PSA unit 1709. From the PSA unit, light stream comprising methane, hydrogen, CO and $CO_2$ can be directed to a methanation unit 1710, and an olefinic stream can be directed to an ETL reactor 1711 and reacted to form higher hydrocarbon products. The ETL product stream can be directed to a heat recovery unit 1712, where boiler feed water (BFW) 1728 can be heated, at least a portion of which can be fed 1729 to the heat recovery unit 1706. The ETL product stream can then be directed to another knockout drum 1713. The overhead stream from the knockout drum can be directed to a low temperature separations unit 1714, while the bottoms stream from the knockout drum can be directed to a $C_4$ removal unit 1715, which can produce a $C_4$ stream 1730 and a $C_{5+}$ stream 1731. Overhead from the low temperature separations unit, as well as product from the methanation reactor, can be directed back to the compressor 1703.

Figure 18:
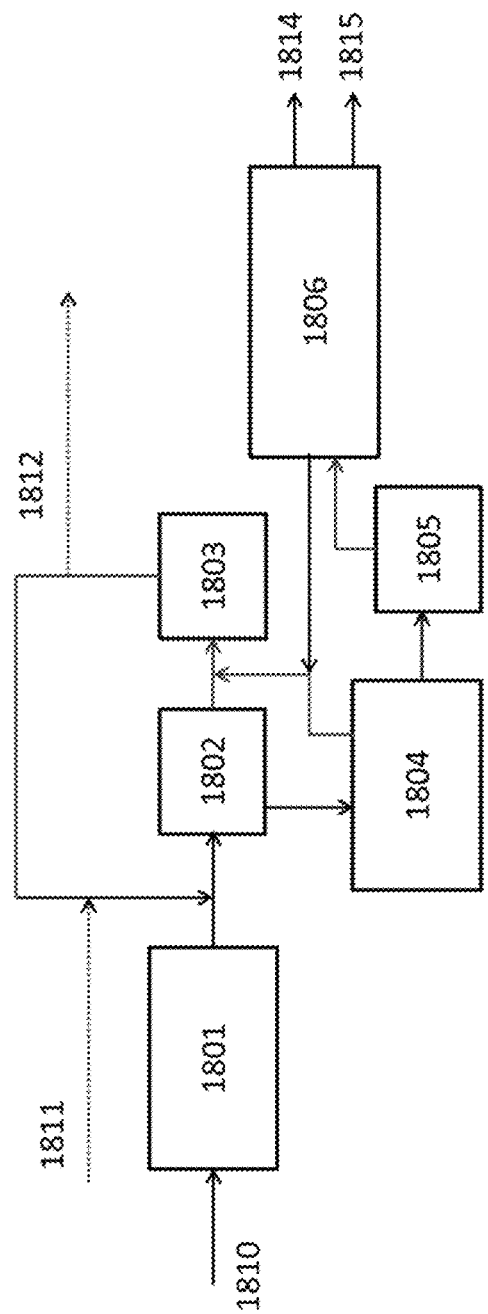
FIG. 18 shows an exemplary PSA unit integrated with an OCM-ETL system in a natural gas liquids (NGL) application.

OCM-ETL systems of the present disclosure can be integrated into and combined into conventional NGL extraction and NGL fractionation sections of a midstream gas plant. Where NGLs in the gas stream are declining (or gas is dry), the deployment of OCM-ETL can utilize an existing facility to produce additional liquid streams. The implementation of OCM-ETL can allow for the generation of on specification "pipeline gas." The products from the facility can be suitable for use (or on specification or "spec") as pipeline gas, gasoline product, hydrocarbon (HC) streams with high aromatic content, and mixed $C_4$ products. The PSA systems discussed above can be employed to separate, pre-separate or purify the hydrocarbon feed streams in the integrated NGL OCM-ETL system. FIG. 18 shows an exemplary NGL extraction facility integrated with an OCM-ETL system. As shown in FIG. 18, for example, the feed to the PSA 1802 can be the net incoming gas from the treatment system 1801, which can treat a methane stream (e.g., natural gas) 1810. The PSA system can separate the feed to the OCM reactor 1803, which is mostly methane and lighter components with some ethane to utilize a PBC section of the OCM reactor, and the feed to the ETL reactor 1805, which can first be processed in a natural gas liquids extraction system 1804. The feed to the ETL system can be the PSA tail gas and OCM effluent comprising ethylene, propylene, ethane, propane, hydrogen, methane, and other components. In some cases, the OCM effluent can be directly fed to the ETL reactor. In some cases the OCM effluent is hydrogenated and fed to the ETL system. In some cases, as shown for example in FIG. 18, the OCM effluent is fed back to the PSA unit for separation; additional natural gas 1811 can be added, and a stream can be recovered 1812 (e.g., for use as pipeline gas). In some examples, the system may have a methanation unit that takes in the effluent from ETL reactor or OCM reactor and converts the CO, $CO_2$ and $H_2$ to methane, thereby further increasing the carbon efficiency of the process. The existing NGL extraction and product fractionation 1806 sub-systems can then be used to fractionate the final products, including into a mixed $C_4$ stream 1814 and a $C_{5+}$ product stream 1815.

Refining

Refinery gas typically contains valuable components like hydrogen, methane, ethane, ethylene, propane, propylene, and butane. Most commonly, refinery off-gases (ROG) are exported to the fuel gas system, thereby losing the value of the components contained therein. The OCM-ETL process can be used to improve the value of products as the OCM converts the methane to ethylene and the ETL converts olefins (e.g., those existing in the ROG and those generated by OCM) to higher value liquids as $C_4$ components, gasoline blends, or aromatic components.

Figure 19:
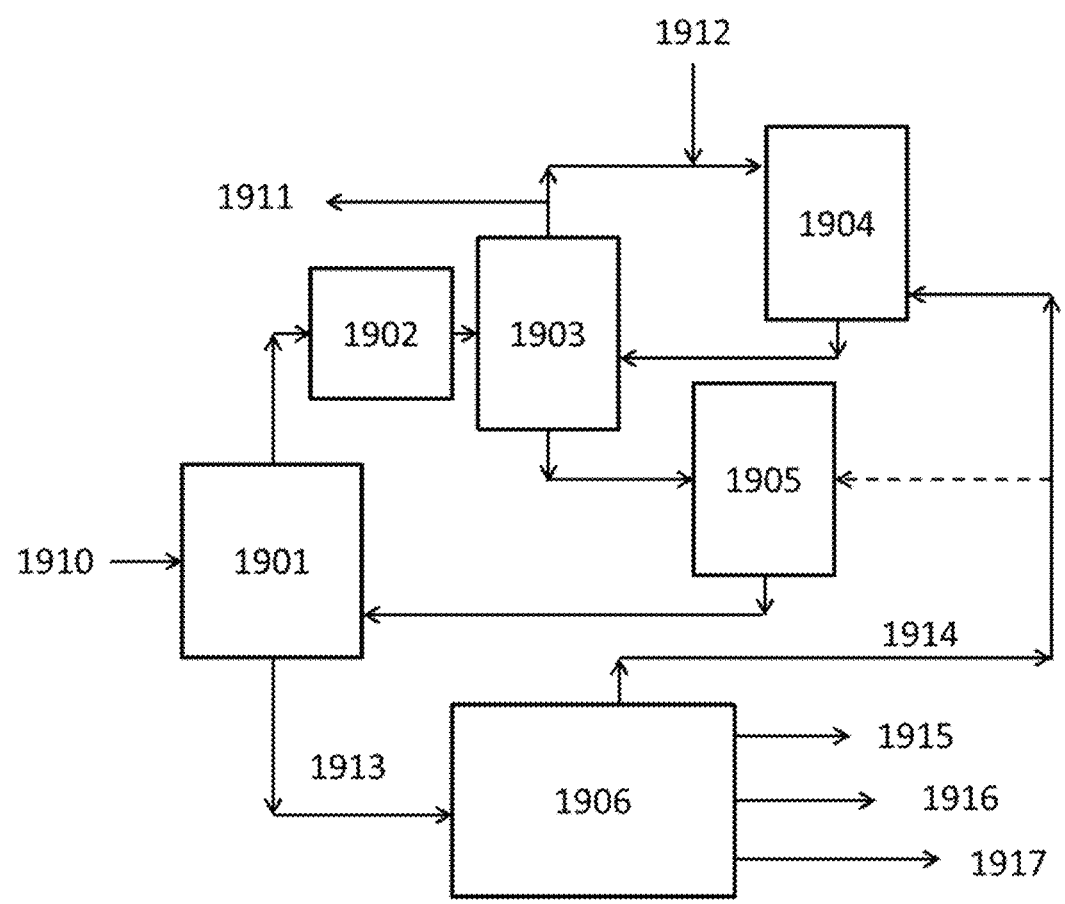
FIG. 19 shows an exemplary PSA unit integrated with an OCM-ETL system for a refining application.

FIG. 19 shows an exemplary PSA unit integrated to a refinery process scheme. A refinery gas plant 1901 can receive gas 1910 from cracking or other units. The PSA unit 1903 (after, for example, treatment of the gas in a treatment unit 1902) can separate components in refinery gas plant off gas to methane and a $C_{2+}$ cut which contains most or all of the olefinic materials. The methane can be used as refinery fuel 1911 and/or directed to an OCM unit 1904 with post-bed cracking. The OCM feed can be supplemented with additional natural gas 1912. The olefinic materials can be directed to an ETL reactor 1905. The OCM effluent can also be routed to the PSA where the olefins produced in the OCM are also sent to the ETL reactor. In some cases, the OCM effluent can be routed to the ETL reactor. In some cases, the OCM effluent may be hydrogenated before being sent to the PSA unit or ETL reactor. Some techniques may dictate the use of a cryogenic demethanizer in place of the PSA, but the application of PSA to pre-separate the refinery off-gas into a product stream and a tail gas stream containing the heavier hydrocarbons which is the feed to ETL reactor can result in significant cost savings. The product stream can contain methane, ethane, CO, $CO_2$, and other components, with of each component from 1 to 99%. A $C_{3+}$ stream 1913 from the refinery gas plant can be directed to a product fractionation system 1906, which can provide a $C_2/C_3$ stream 1914 (which can be directed to the OCM reactor), an $iC_4$ stream 1915, a gasoline blend stream 1916, and/or a kerosene/jet stream 1917.

Figure 20:
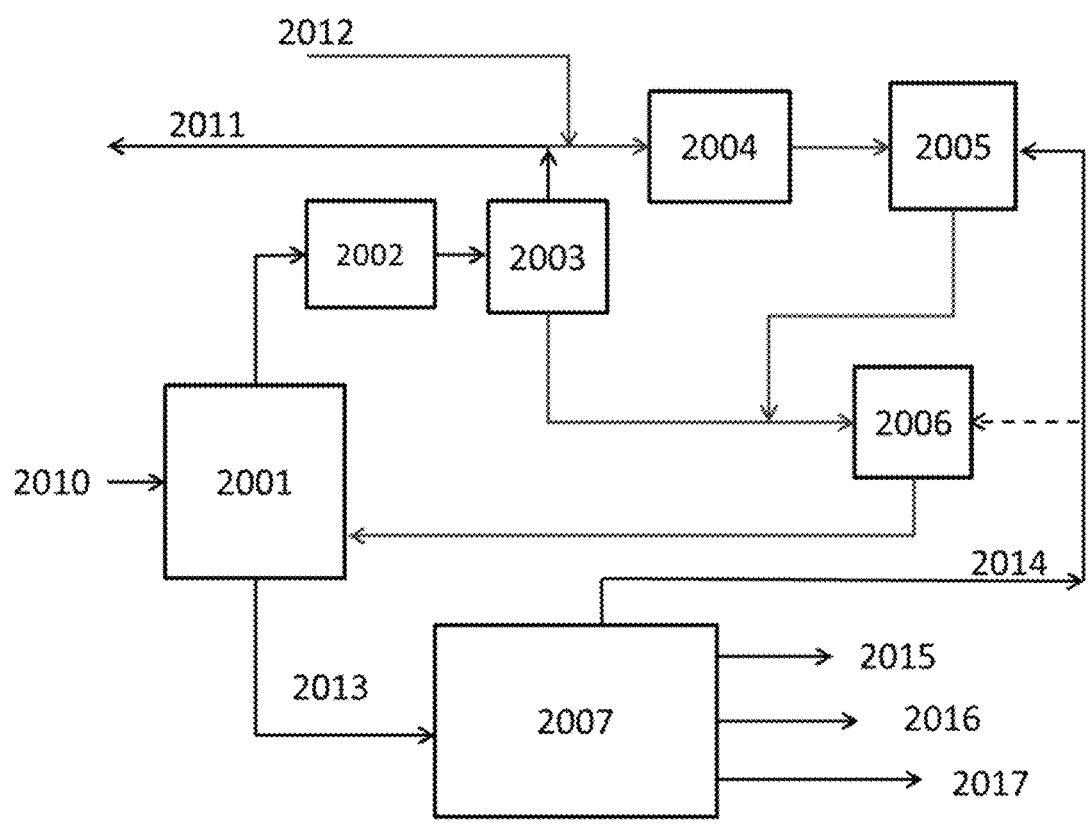
FIG. 20 shows an exemplary alternate scheme for a PSA unit integrated with an OCM-ETL system for a refining application.

As shown in FIG. 20, in some cases the system can have a methanation unit to further improve the carbon efficiency of the process. A refinery gas plant 2001 can receive gas 2010 from cracking or other units. The PSA unit 2003 (after, for example, treatment of the gas in a treatment unit 2002) can separate components in refinery gas plant off gas to methane and a $C_{2+}$ cut which contains most or all of the olefinic materials. The methane can be used as refinery fuel 2011 and/or directed to a methanation unit 2004, and then to an OCM reactor 2005 with post-bed cracking. The methanation feed can be supplemented with additional natural gas 2012. The olefinic materials can be directed to an ETL reactor 2006. The OCM effluent can be routed to the ETL reactor. In some cases, the OCM effluent can also be routed to the PSA where the olefins produced in the OCM are also sent to the ETL reactor. In some cases, the OCM effluent may be hydrogenated before being sent to the PSA unit or ETL reactor. Some techniques may dictate the use of a cryogenic demethanizer in place of the PSA, but the application of PSA to pre-separate the refinery off-gas into a product stream and a tail gas stream containing the heavier hydrocarbons which is the feed to ETL reactor can result in significant cost savings. The product stream can contain methane, ethane, CO, $CO_2$, and other components, with of each component from 1 to 99%. A $C_{3+}$ stream 2013 from the refinery gas plant can be directed to a product fractionation system 2007, which can provide a $C_2/C_3$ stream 2014 (which can be directed to the OCM reactor), an $iC_4$ stream 2015, a gasoline blend stream 2016, and/or a kerosene/jet stream 2017.

Metal-Organic Frameworks (MOFs) for Hydrocarbon Separation

The separation section of OCM unit can employ cryogenic distillation systems. In some cases, the distillation section can be partially or completely replaced by efficient advanced separation technologies that operate at higher/room temperatures, such as membranes or PSA. This can result in energy savings.

Among the materials used for membranes and adsorption beds, metal-organic frameworks (MOFs) can be highly beneficial. MOFs can comprise metal ions and organic linkers. MOFs can be highly porous sponge-like materials. The choice of metal ion and linker can define the structure and hence the properties of MOFs. MOFs can exhibit advantages of both organic and inorganic moieties. They can be more advantageous than zeolites due to higher surface areas and higher flexibility in pore sizes (e.g., based on their synthesis). They can be better than typical membranes for separation since they can be more robust, more mechanically and thermally stable, and can avoid issues such as carrier poisoning or reduction of complexing agents.

The process effluent from OCM can comprise light gases, such as methane, hydrogen, carbon dioxide, ethylene, ethane, acetylene, propane, propene and $C_{4+}$ compounds. MOFs can be used to separate $C_{2+}$ compound streams from the bulk $CH_4$ and $H_2$ in effluent. MOFs can also be used to recover ethylene from a mixed stream of $C_2$ compounds, $C_3$ compounds and $C_{4+}$ compounds, remove $CO_2$, and recover hydrogen for further processing.

Different combinations of MOFs can be synthesized to provide different separation properties. MOFs can be useful in hydrocarbon separation due to their capability of separating component gases by mechanisms such as molecular sieving, characteristic gate opening pressures for different penetrant molecules or other changes in the structure of the MOFs due to adsorbent/adsorbate interactions. Without being limited by theory, adsorption selectivity can arise from interactions using π-complexation between the double bond in ethylene molecules and partial positive charges of co-ordinatively unsaturated metal ions (e.g., Cu(II)). MOFs such as HKUST-1 can be used to separate ethylene from ethane. Other MOFs capable of separating ethylene over ethane include $Ag^+$ based MOFs, $Co_2$(2,5-dihydroxyterephthalate, or "dhtp"), and $Mg_2$(dhtp). MOFs such as ZIF-7, ZIF-8, and ZIF-4 can be used for selective adsorption of paraffins (e.g., ethane) over ethylene due to the gate-opening effect or the breathing behavior of the MOF. ZIF-8 can adsorb alkanes (e.g., methane) over alkenes (e.g., ethylene). The selectivity of this separation can be controlled by adjusting the hydration level of the MOF. MOFs such as ZIF-67, SBMOF-1, SBMOF-2, Cu-TDPAT, USTA-33a, ZJU-61, USTA-33, USTA-10a can be used for selective separation of methane from other hydrocarbons such as $C_2$ compounds. The MOF $M_2$(dobdc) can be used to effectively separate acetylene, ethylene, ethane, and methane collectively or individually from their mixtures. The $M_2$(dobdc) can be in the meta form $M_2$(m-dobdc) or the para form $M_2$(p-dobdc). The metal can be any suitable metal such as iron (Fe), nickel (Ni) or cobalt (Co). Further information on these MOFs can be found in PCT Publication No. WO 2015/066693A1, which is incorporated herein by reference in its entirety. IRMOFs, such as MOF-5, can be used for separation of hydrogen from hydrogen/methane and hydrogen/$C_2$ mixtures. RPM3-Zn can be used to separate $C_1$-$C_4$ paraffins. MOFs such as UTSA-100, SIF SIX, ZJU-5 can be utilized for acetylene removal from the olefins stream where back-end acetylene removal is used rather than acetylene hydrogenation. MOFs such as M-(dobdc) can be modified with amines to selectively remove $CO_2$. Several MOFs such as ZIF-68-70, 78, 79, 81 82, MOF-11, MOF-508b, PCN-60, 61, MIL-100, MIL-101, ZIF-8, SNU-9, MIL-102(Cr), MIL-53(Cr) have been studied for removal of $CO_2$ from methane and nitrogen and can be utilized for, e.g., a front end $CO_2$ removal system. MOFs such as $M_2$(dobpdc) can be used to remove $CO_2$ from other gases and can be used for $CO_2$ removal front or back of the OCM process described herein. MOFs such as Fe-BTTri can be used for CO removal from various components such as $CO_2$, $N_2$, $CH_4$ and can be used for back end CO removal in the OCM unit.

MOFs can be used in the adsorbent beds of PSA/TSA system or as a part of membrane based applications. As part of membrane systems, they can be incorporated in thin film membranes or mixed matrix membranes (MMMs). With MMMs, MOFs have shown improved gas separation qualities, with increased permeability and selectivity using MMMs. Mixed matrix membranes can combine the advantages of easy and cheap fabrication of polymer membranes with the improved gas separation properties of different MOFs.

Figure 21:
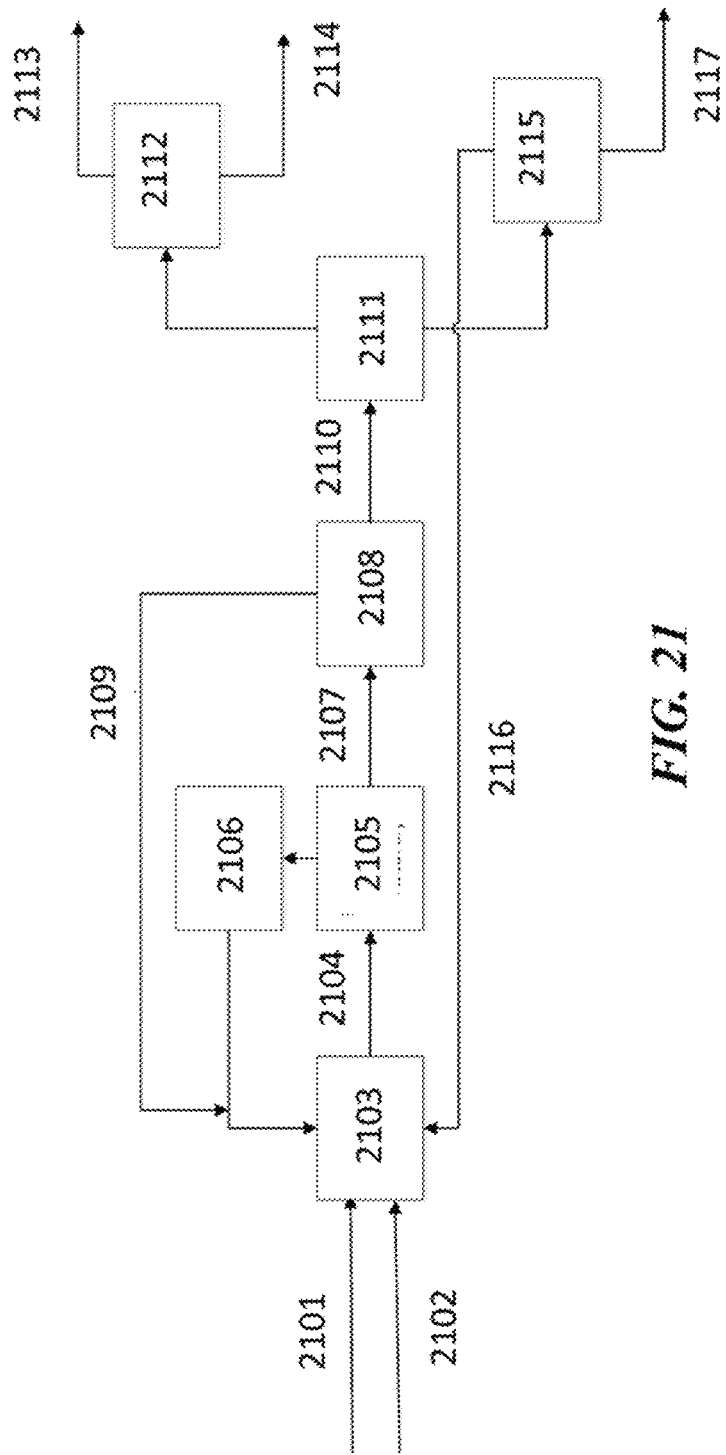
FIG. 21 shows an exemplary OCM process scheme employing metal-organic framework (MOF) separations.

For an OCM process, MOFs can be utilized for separation of various light hydrocarbons. In FIG. 21, for example, oxygen 2101 and methane 2102 feed the OCM reactor 2103. The process effluent 2104 comprising mainly hydrogen, CO, $CO_2$, $CH_4$, $C_2H_4$, $C_2H_6$ and $C_{3+}$ hydrocarbons is first sent to a pretreatment unit 2105. Any potential contaminants to the downstream recovery systems (e.g., contaminants to membranes, adsorbent beds containing zeolites, polymers or MOF membranes or adsorbents) can be removed in this unit. This unit can include a $CO_2$ removal system, acetylene removal bed for diene sensitive beds, sulfur removal bed, or molecular sieve dryer. Hydrogen can also be recovered from this stream, for example by utilizing an MOF bed selective to hydrogen over other light hydrocarbons such as methane. Hydrogen removal can be important for separation systems using adsorbents/membranes that are sensitive to hydrogen in the operations that follow. The hydrogen, $CO_2$ and CO streams can be sent to the methanation unit 2106 for further conversion to methane. The outlet 2107 from the pretreatment unit can then be sent to a $C_1/C_{2+}$ bulk separation unit 2108 capable of separating methane from $C_2$ and higher hydrocarbons. This separation unit can be a PSA, membranes made of zeolites such as CaX, NaX zeolite, microporous titanosilicates such as ETS-4, ETS-10, or selective MOF adsorbents/membrane systems that can perform the same function (for example, MOFs such as SBMOF-1, SBMOF-2, Zn-SIFSIX-Pyrazine, PCN-250, Cu-TDPAT, ZIF-67, ZJU-61, USTA-33, and USTA-10 can be used). These materials can be used for separating the light components including $N_2$ and $H_2$ along with methane and hence may not require any pre-treatment beds prior to a C1/C2+ bulk separation unit. A methane gas stream 2109 separated can be recycled back to the OCM reactor. Alternatively, the outlet from the $C_1/C_2$ separation containing methane can be recycled back to the methanation unit 2106, for example if the stream contains portions of CO, $CO_2$ or $H_2$. The $C_{2+}$ stream 2110 can then be sent into an olefin/paraffin separation unit 2111, for example made of MOFs, zeolites, or polymeric membranes in a PSA or membrane unit. MOFs that can be useful for this operation include HKUST-1, $CO_2$ (dhtp), $Mg_t$ (dhtp), M (dobdc) (M can be Mg, Mn, Fe, Co, Ni, Zn), ZIF-7, ZIF-8, ZIF-4, and other Ag ion based MOFs such as Ag-MIL-101, Silver-Organic Frameworks Constructed with 1,1'-Biphenyl-2,2',6,6'-tetracarboxylic Acid or Silver m-phosphonobenzoate $Ag_6(m-O_3PC_6H_4CO_2)_2$, Ag(I) coordination polymer with 2,5-dimethylpyrazine ligand. Polymeric adsorbents capable of silver complexation such as Ag+ exchanged Amberlyst resin can also be used for such applications. The olefins stream can then be sent into a separator 2112 such as a flash unit operation or distillation column or any other separation system (e.g., PSA/TSA/membranes) that can separate pure ethylene 2113 from the $C_{3+}$ olefins 2114. A combination of the separation techniques can also be used to recover polymer grade ethylene. The paraffin stream can also be sent into a separator 2115 such as flash operation, distillation section, PSA, TSA unit, or membrane system to separate ethane from $C_{3+}$ paraffins. Ethane can be recycled 2116 back to the OCM reactor. Alternatively, the entire paraffin stream 2117 can also be recycled back into the OCM reactor to take advantage of the post bed cracking section of the reactor to convert into further ethylene. Separation of paraffins can also be performed using MOF adsorbent beds of RPM3-Zn.

Figure 22:
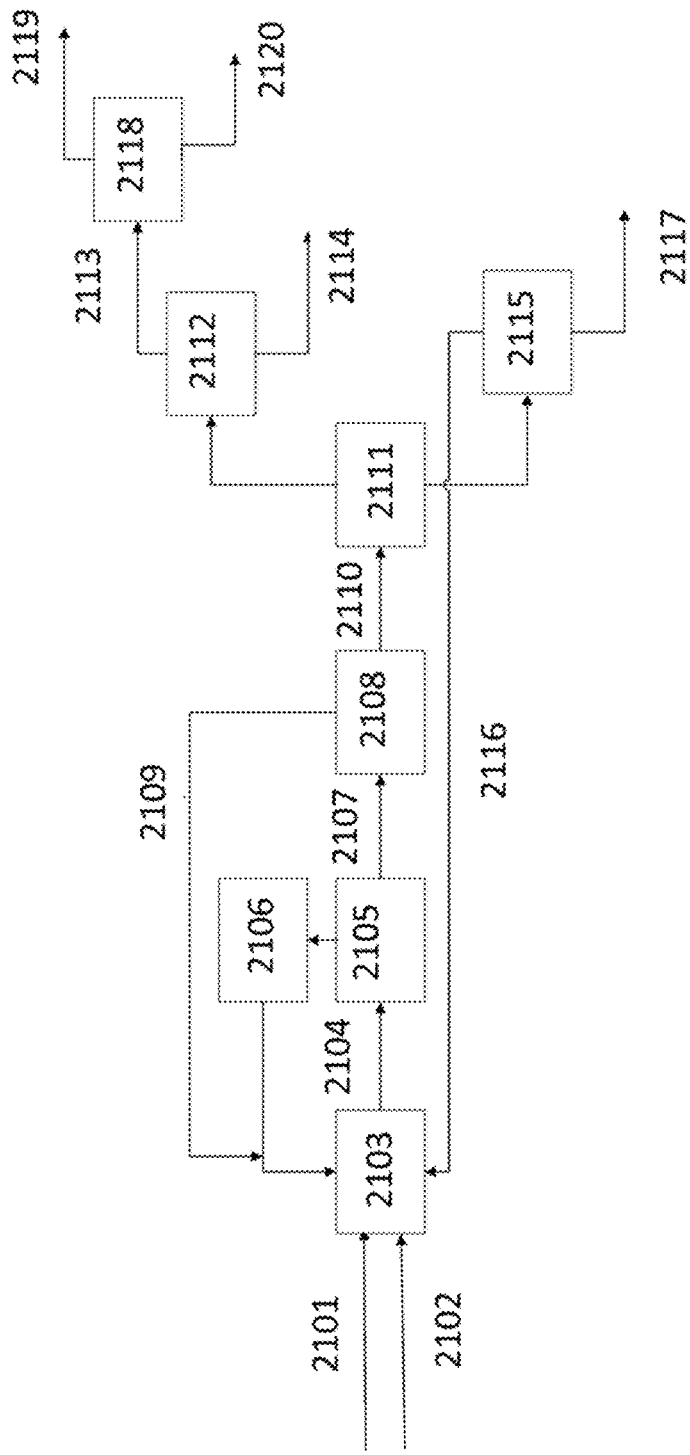
FIG. 22 shows an exemplary OCM process scheme employing MOF separations.

In FIG. 22, a similar process scheme as FIG. 21 is proposed, except for the acetylene removal unit 2118 location, separating acetylene 2119 from ethylene 2120. Here the acetylene removal unit is downstream of the ethylene/propylene+ separation unit. This scheme can be utilized when acetylene is not a contaminant/poison to the olefin/paraffin separation beds or any of the separation systems prior to olefin separation unit (MOF/PSA/membrane systems). This scheme can be utilized if olefin/paraffin separation system is based on non-$Ag^+$ adsorbent beds/membranes such as Fe-MOF-74. In such a system, acetylene removal can be performed on the final product stream using MOF adsorbent beds/membranes selective to acetylene removal, for example, USTA-67a.

Figure 23:
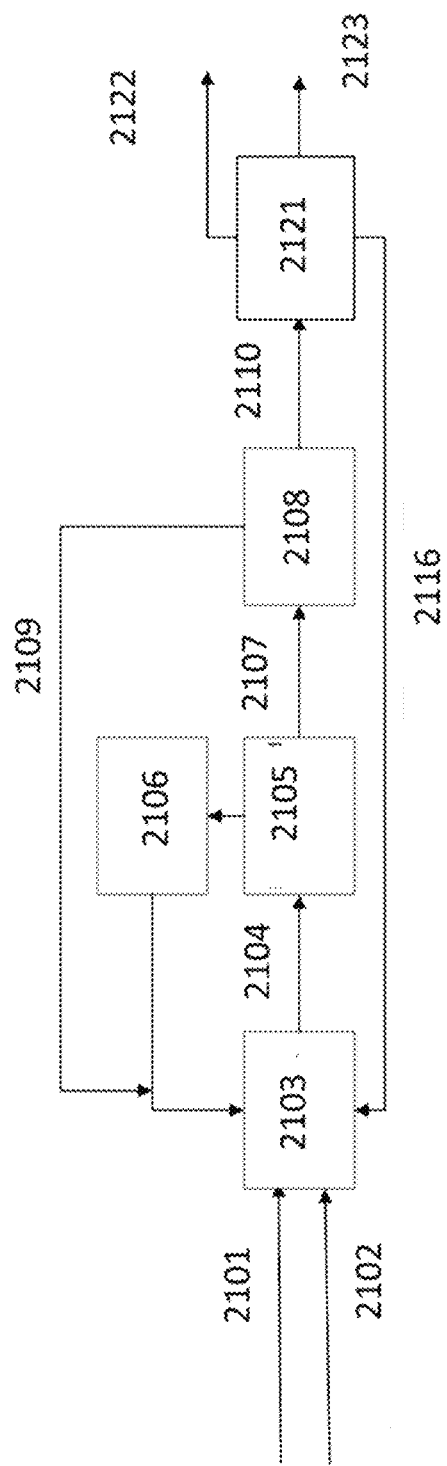
FIG. 23 shows an exemplary OCM process scheme employing MOF separations.

In FIG. 23, the OCM effluent, after pre-treatment and hydrogen recovery (where necessary), is sent to adsorbent beds in a PSA system or to a membrane system containing MOFs such as $M_2$(dobdc) (meta or para form, M can be Mg, Mn, Fe, Co, Ni) 2108, 2121 that are by themselves capable of separating all the lighter hydrocarbons into individual components ($CH_4$, $C_2H_4$, $C_2H_6$, $C_2H_2$). In such a system, the effluent from pre-treatment section can be first sent into an initial methane removal unit (PSA with multiple beds for simultaneous adsorption/desorption to run the process continuously). The desorbed mixture of $C_{2+}$ streams can then be separated into ethylene 2122, ethane 2116 and acetylene 2123 based at least in part on their different elution rates from the adsorbent bed (permeation times if membranes were to be used). Multiple beds operating simultaneously for this unit can help with continuous separation of the $C_2$ streams. Such a scheme can use a $C_{3+}$ removal system (PSA/membrane based on MOFs) for removing the $C_{3+}$ components prior to the methane removal unit.

Figure 24:
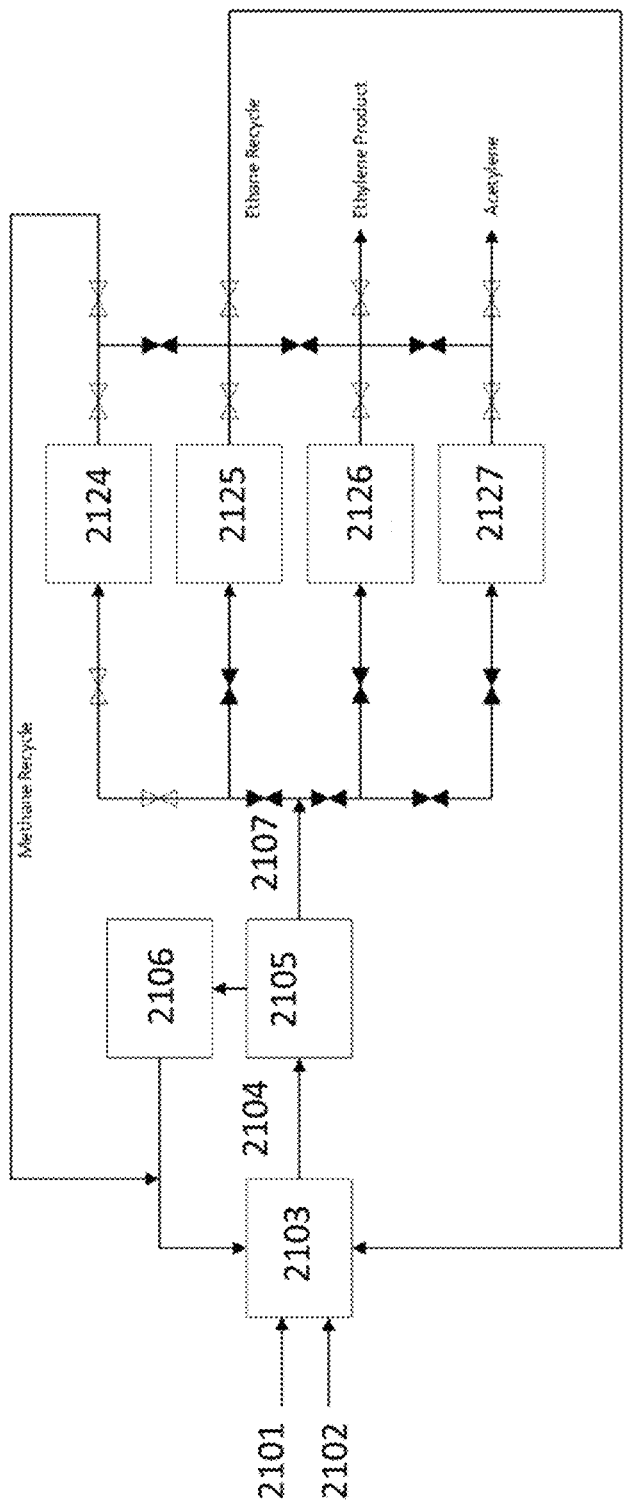
FIG. 24 shows an exemplary OCM process scheme employing MOF separations.

FIG. 24 represents a similar system utilizing MOFs such as $M_2$(dobdc) (meta or para form, M can be Mg, Mn, Fe, Co, Ni) capable of separating individual light hydrocarbons, but each running in a different mode. A system utilizing 4 different adsorption systems (e.g., PSA) 2124, 2125, 2126, and 2127, with each bed operating in different mode is represented. Each bed is either in $CH_4$ removal mode 2124, $C_2H_2$ removal mode 2127, $C_2H_4$ recovery mode 2126 or $C_2H_6$ removal mode 2125. Using different valve-sequencing for the process gas (feed and outlet) between beds, the feed gas can be directed appropriately and effectively separated continuously into individual components thus recovering ethylene without lag times that may be generated in the adsorbent beds.

Figure 25:
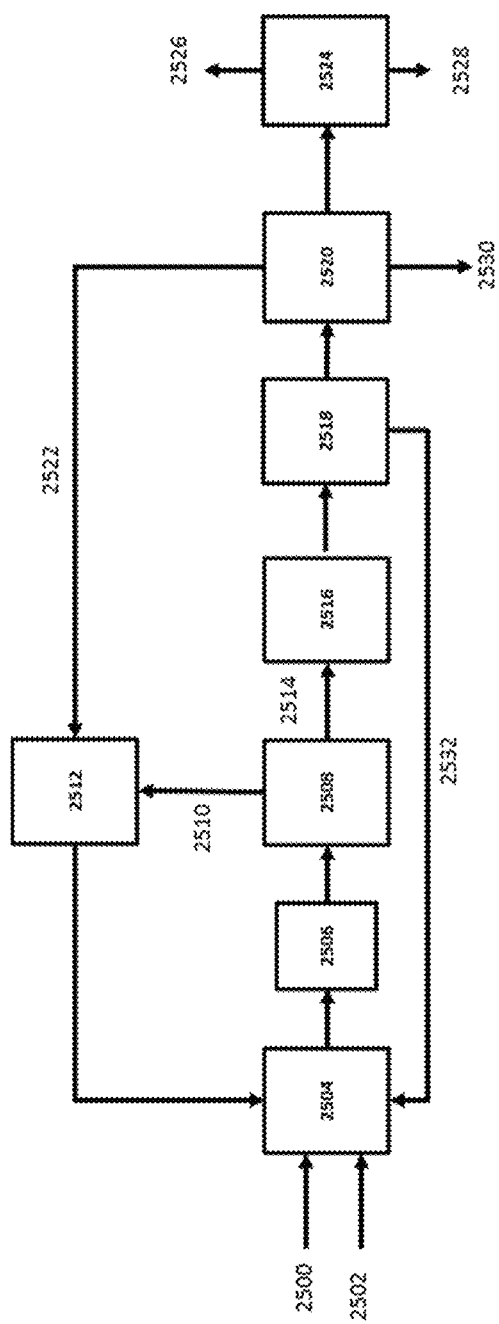
FIG. 25 shows an exemplary OCM process scheme employing MOF separations.

FIG. 25 shows another example of an OCM system. In this case, oxygen 2500 and methane 2502 can be fed into an OCM reactor 2504 to produce an OCM effluent. The OCM effluent can be sent through a pre-treatment unit 2506 (e.g., for water, sulfur removal) followed by a (bulk) separation unit 2508 such as PSA or membranes that utilize adsorbent materials capable of separation $C_1$ compounds from $C_{2+}$ compounds. These materials can be adsorbents that aid in separation using molecular size differences (e.g., CaX Zeolite, ETS-4). This PSA/membrane can separate the quenched OCM reactor effluent into two streams. The methane rich stream with hydrogen 2510 can be recycled back to OCM via methanation 2512. The $C_{2+}$ compounds 2514 can be fed into an optional acetylene hydrogenation unit 2516 that selectively hydrogenates acetylene to ethylene and ethane. This stream can then be fed to the an olefin/paraffin separation module 2518 containing, for example adsorbents or membranes with pi-complexation materials such as silver ion MOFs, resins such as Ag+ exchanged Amberlyst 15 resin or $M_2$(dobdc) (meta or para form, M can be Mg, Mn, Fe, Co, Ni) MOFs, or any material which can selectively separate olefin from paraffins. A post-$CO_2$ removal unit 2520 can follow. A post $CO_2$ removal unit can reduce the cost since the operation can be performed on a stream with much lower flow rate. The $CO_2$ removal unit may use liquid absorption or $CO_2$ removal adsorbents in a PSA or TSA or a membrane system. The $CO_2$ stream 2522 can then be recycled into the methanation reactor for further conversion into methane. The $CO_2$-free stream can then be sent into an acetylene removal unit (if acetylene is not hydrogenated prior to olefin/paraffin separation) utilizing materials and adsorbents capable of removing acetylene from ethylene such as UTSA-100, SIFSIX, or ZJU-5 (not shown). Once free from acetylenes, the product stream can go through a final separation unit 2524 to separate ethylene 2526 and propylene 2528. In some cases, some $CO_2$ can be vented 2530 and/or the $C_{2+}$ paraffin stream 2532 can be recycled to (the cracking section of) the OCM reactor 2504.

Figure 26:
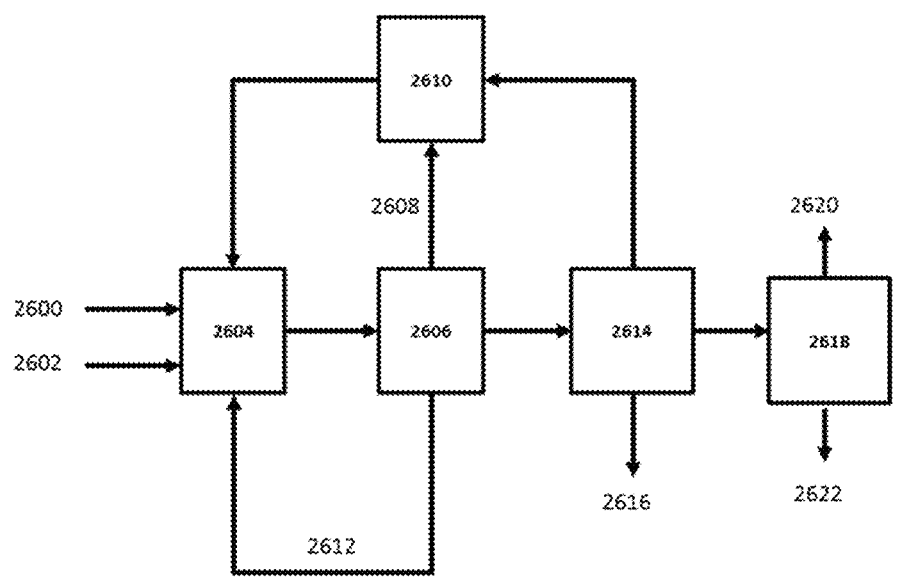
FIG. 26 shows an exemplary OCM process scheme employing MOF separations.

FIG. 26 shows another example of an OCM system. In this case, oxygen 2600 and methane 2602 can be fed into an OCM reactor 2604 to produce an OCM effluent. The OCM effluent can, after pre-treatment where necessary (not shown), can be sent to an olefin recovery module 2606. The olefin recovery module can contain adsorbent beds in a PSA or TSA system and/or can be a membrane system containing MOFs such as $M_2$(dobdc) (meta or para version, M can be Mg, Mn, Fe, Co, Ni for example) that are by themselves capable of separating the lighter hydrocarbons into individual components or groups thereof (e.g., $CH_4$, $C_2H_4$, $C_2H_6$, $C_2H_2$). In such a system, the effluent from pre-treatment section can be sent into an initial bulk lights removal unit (e.g., PSA with multiple beds for simultaneous adsorption/desorption to run the process continuously and remove methane and lighter components). The desorbed mixture of $C_{2+}$ streams (with lower amounts of $C_1$ and lighter components) can then be separated into ethylene, ethane and acetylene based at least in part on their different elution rates from the adsorbent bed (permeation times if membranes were to be used). Such a configuration can use a $C_{3+}$ removal system (e.g., PSA/membrane based on MOFs) for removing the $C_{3+}$ components prior to the methane removal unit. The separations module can send a stream of $C_1$ molecules and hydrogen 2608 to a methanation unit 2610 and/or can send $C_{2+}$ paraffins 2612 to (the cracking section of) the OCM reactor 2604. A back-end $CO_2$ and acetylene removal unit 2614 can then be utilized to purify olefins stream from $CO_2$ and acetylenes. The $CO_2$ removal unit can include typical $CO_2$ removal liquid absorption columns or PSA/TSA/membranes systems that incorporate $CO_2$ removal adsorbents. Acetylene removal may be performed by adding additional acetylene selective MOF beds such as UTSA-100, SIF SIX, ZJU-5. A back-end purification system can greatly reduce the operating and capital cost of removal units. The $CO_2$ removal unit can send $CO_2$ to methanation 2610 and/or to vent 2616. An olefin separation module 2618 can produce an ethylene stream 2620 and a propylene stream 2622.

In summary, different MOFs can be utilized for their specific selectivities and adsorption capabilities, for example in MMMs or adsorbent beds as PSA systems for hydrocarbon separation of the OCM effluent. MOFs can be very advantageous for their on-purpose synthesis and high surface areas (highest surface area/gram compared to any other material). MOFs in combination with other separation systems (such as polymeric membranes, zeolites, and cryogenic distillation) can be used in novel process schemes to produce OCM product (e.g., ethylene).

Separations Systems Using an Oil Absorption Tower

Another aspect of the present disclosure provides a method and system for separating the OCM reactor product mixture using an oil absorption system along with distillation. The oil absorption system may include (a) an oil absorption and stripper system and/or (b) an oil absorption system preceded by a pre-separation column to do a bulk separation between $C_1$ and $C_2$ compounds. This system can eliminate the need of a demethanizer, thereby reducing the overall energy consumption and capex by eliminating the need for $C_2$ or $C_1$ refrigeration.

Figure 27A:
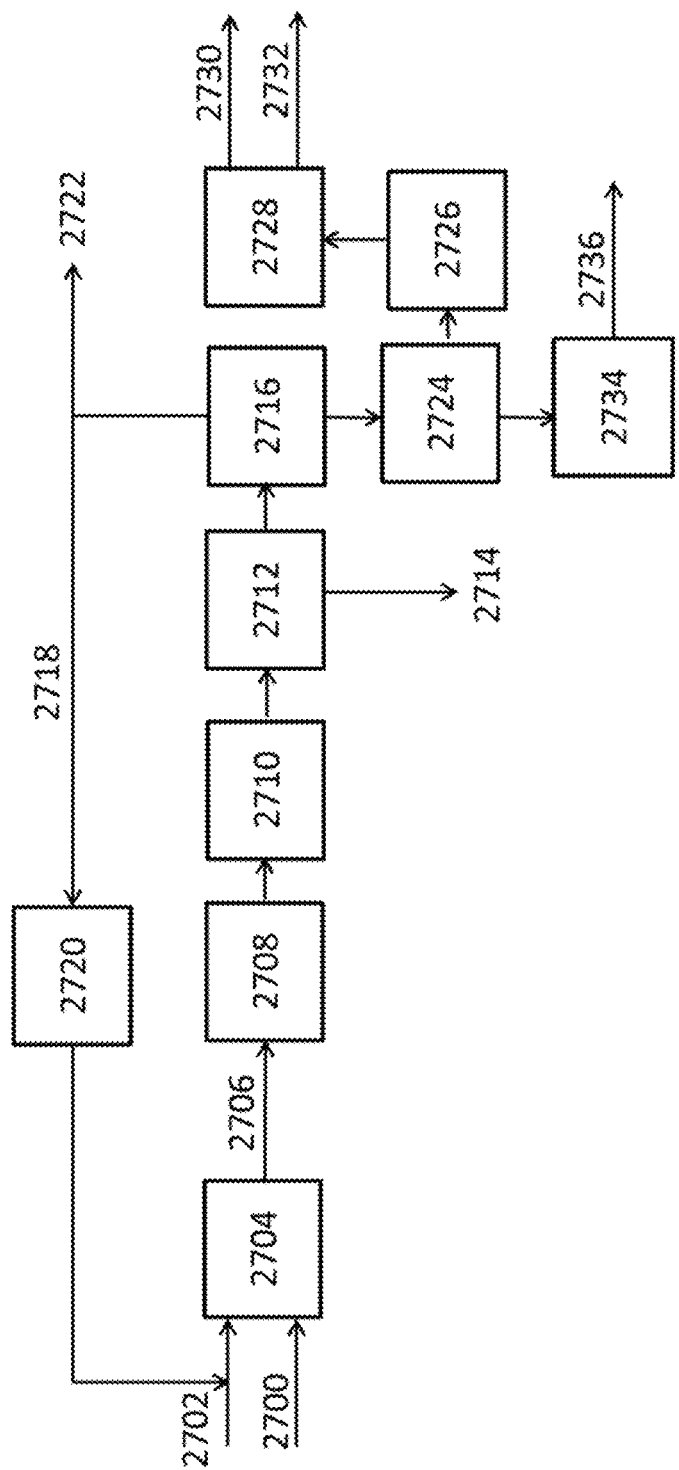
FIG. 27A shows an example of OCM separations using an oil absorption tower.

As shown in FIG. 27A, oxygen 2700 and methane 2702 can be fed to an OCM reactor 2704 and reacted to produce an OCM effluent 2706. The OCM effluent can be compressed 2708, and the compressed stream can be sent to a treatment unit 2710. The treatment unit can include a $CO_2$ removal system, drying and/or removal of oxygenates. The treatment unit can be followed by a heavies removal system 2712. The heavies removal system can remove $C_{4+}$ compounds 2714. The overhead from the heavies removal system can be fed to a pre-separation and absorption system 2716. The overhead 2718 from the pre-separation and oil absorption system can consist mainly of the $C_1$ and lighter components. The majority of the methane rich overhead product can be recycled to the OCM reactor via a methanation reactor system 2720. A small fraction can be purged 2722 to remove any inerts building up in the system, alternately, the $C_1$ fraction can be sent to the fuel gas. The $C_{2+}$ components (e.g., propane, propylene, ethane, ethylene, methane, and lights such as $H_2$) can be sent to a de-ethanizer 2724 followed by acetylene hydrogenation 2726 and a $C_2$ splitter 2728 to produce high purity polymer grade ethylene 2730. Ethane 2732 can be recycled to OCM (not shown). A $C_3$ splitter 2734 can be used to produce a propylene product 2736.

Figure 27B:
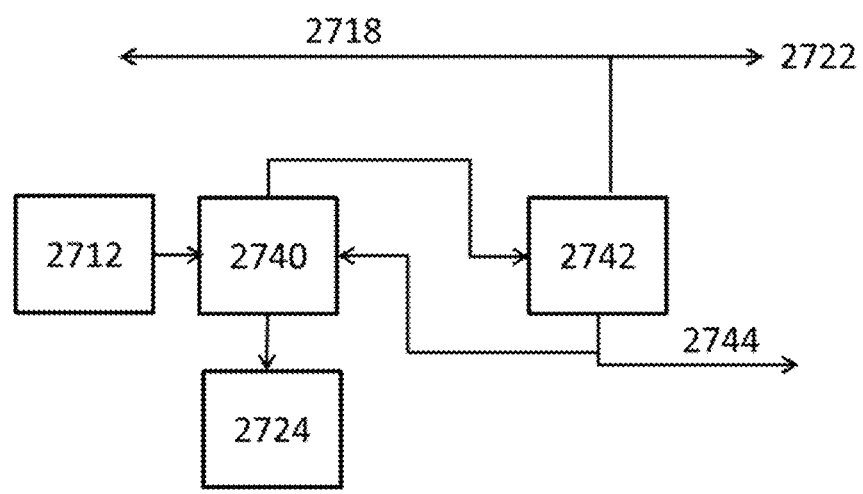
FIG. 27B shows an example of a pre-cut and absorption system.

FIG. 27B shows an example of the pre-separation and absorption system 2716 comprising a pre-separation column 2740 and an oil absorption unit 2742. The pre-separation column can be a distillation column which performs a bulk separation between $C_1$ and lighter components and $C_2$ and heavier components. In this instance, bulk separation implies that the distillation doesn't necessarily achieve high purity streams (non-sharp distillation). The overhead from the pre-separation column, which consists of $C_1$ and lighter components can be sent to an oil absorber where the circulating lean oil absorbs $C_2$ and heavier components to complete separation of $C_1$ from $C_{2+}$ components. The heavy oil can be regenerated in the first pre-separation column. Alternatively, the oil can be regenerated in a separate system 2744. One advantage of using a pre-separation column and an oil absorption system is the reduction in the energy consumption that is incurred in a conventional cryogenic demethanizer.

In some cases, the feed to the separation system can be the product from either an OCM reactor as discussed above, an OCM process integrated with a Methanol to Olefins (MTO) unit, an OCM process integrated with a steam cracker, or an OCM process integrated with a dimerization and metathesis unit for example.

Methods and systems of the present disclosure can be combined with or modified by other methods and systems, such as those described in U.S. patent application Ser. No. 14/591,850, filed Jan. 7, 2015, now published as U.S. Patent Pub. No 2015/0232395; U.S. patent application Ser. No. 13/936,783, filed Jul. 8, 2013, now published as U.S. Patent Pub. No. 2014/0012053; U.S. patent application Ser. No. 13/936,870, filed Jul. 8, 2013, now published as U.S. Patent Pub. No. 2014/0018589; U.S. patent application Ser. No. 13/900,898, filed May 23, 2013, now published as U.S. Patent Pub. No 2014/0107385; U.S. patent application Ser. No. 14/553,795, filed Nov. 25, 2014, now published as U.S. Patent Pub. No. 2015/0152025; U.S. patent application Ser. No. 14/592,668, filed Jan. 8, 2015, now published as U.S. Patent Pub. No. 2015/0210610; and U.S. patent application Ser. No. 14/789,953, filed Jul. 1, 2015, now U.S. Pat. No. 9,334,204, each of which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for generating compounds with two or more carbon atoms ($C_{2+}$ compounds), comprising:
   (a) directing oxygen ($O_2$) and methane ($CH_4$) into an oxidative coupling of methane (OCM) reactor having a first section and a second section downstream of said first section, to produce a product stream, which first section reacts said $O_2$ and $CH_4$ in an OCM process to yield ethylene ($C_2H_4$), ethane ($C_2H_6$), and heat, which second section uses said heat to convert said $C_2H_6$ from said first section into $C_2H_4$ in a non-OCM process, and which product stream comprises (i) $C_{2+}$ compounds including $C_2H_4$ and $C_2H_6$ and (ii) $C_1$ compounds including unreacted $CH_4$;
   (b) directing said product stream into a first separations unit containing a metal organic framework (MOF) which separates $C_1$ compounds from $C_{2+}$ compounds to produce (i) a first stream comprising $CH_4$ and hydrogen and (ii) a second stream comprising $C_{2+}$ compounds;
   (c) directing said second stream into a second separations unit containing a second MOF which separates $C_{2+}$ olefins from $C_{2+}$ paraffins to produce (i) a third stream comprising $C_{2+}$ olefins and (ii) a fourth stream comprising $C_{2+}$ paraffins;
   (d) directing said third stream into a third separations unit comprising a $CO_2$ removal unit to produce (i) a fifth stream comprising $CO_2$ and (ii) a sixth stream comprising $C_{2+}$ olefins, which $CO_2$ removal unit employs sorbent or solvent separation of $CO_2$;
   (e) directing said sixth stream into a fourth separations unit which separates $C_2H_4$ from $C_{3+}$ olefins to produce an $C_2H_4$ stream;
   (f) directing the first stream into the first section of the OCM reactor; and
   (g) directing the fourth stream into the second section of the OCM reactor.

2. The method of claim 1, wherein the product stream is directed into said first separations unit through one or more additional units.

3. The method of claim 2, wherein the one or more additional units comprises a compressor.

4. The method of claim 2, wherein the one or more additional units comprises a molecular sieve dryer.

5. The method of claim 1, wherein said sorbent or solvent separation of $CO_2$ employs an amine based absorption unit.

6. The method of claim 1, wherein said sorbent or solvent separation of $CO_2$ employs a Benfield process.

7. The method of claim 1, wherein said sorbent or solvent separation of $CO_2$ employs diethanolamine.

8. The method of claim 1, wherein said sorbent or solvent separation of $CO_2$ employs a solvent comprising glycol dimethylethers.

9. The method of claim 1, wherein said sorbent or solvent separation of $CO_2$ employs a carbonate.

10. The method of claim 1, wherein said sorbent or solvent separation of $CO_2$ employs active carbon.

11. The method of claim 1, further comprising directing at least a portion of the first stream to a methanation unit prior to directing to the first section of the OCM reactor;
   directing at least a portion of the fifth stream to the methanation unit; and
   wherein the methanation unit converts carbon dioxide ($CO_2$) and/or carbon monoxide (CO) into methane ($CH_4$) that is directed to the first section of the OCM reactor.

12. The method of claim 1, wherein the first separations unit comprises a pressure swing absorber (PSA) that contains the MOF.

13. The method of claim 1, wherein the first separations unit comprises a temperature swing absorber (TSA) that contains the MOF.

14. The method of claim 1, further comprising directing the sixth stream into an acetylene removal unit comprising an adsorbent capable removing acetylene prior to directing the sixth stream into the fourth separations unit.

* * * * *